United States Patent [19]
Bihovsky et al.

[11] Patent Number: 5,952,328
[45] Date of Patent: Sep. 14, 1999

[54] BENZOTHIAZO AND RELATED HETEROCYCLIC GROUP-CONTAINING CYSTEINE AND SERINE PROTEASE INHIBITORS

[75] Inventors: Ron Bihovsky, Wynnewood; Gregory J. Wells, West Chester; Ming Tao, Maple Glen, all of Pa.

[73] Assignee: Cephalon, Inc., West Chester, Pa.

[21] Appl. No.: 08/968,035

[22] Filed: Nov. 12, 1997

[51] Int. Cl.$^6$ .................................................. A61K 31/54
[52] U.S. Cl. ..................... 514/223.2; 514/19; 514/224.2; 546/146; 544/105; 544/283; 534/136; 534/788
[58] Field of Search .............................. 514/223.2, 224.2, 514/19; 546/146; 544/105, 283

[56] References Cited

U.S. PATENT DOCUMENTS

| | | | |
|---|---|---|---|
| 3,591,584 | 7/1971 | Lombardino et al. | 260/243 |
| 3,960,854 | 6/1976 | Novello | 260/243 D |
| 4,585,793 | 4/1986 | Powers | 514/513 |
| 4,889,851 | 12/1989 | Oku et al. | 514/223.2 |
| 5,004,742 | 4/1991 | Satoh et al. | 514/226.5 |
| 5,384,411 | 1/1995 | Robotti et al. | 549/31 |
| 5,416,094 | 5/1995 | Lal et al. | 514/307 |
| 5,563,127 | 10/1996 | Amparo et al. | 514/64 |

FOREIGN PATENT DOCUMENTS 1 238 159   3/1970   United Kingdom .

OTHER PUBLICATIONS

Zenno, Chem. Abstr. 72, 111525f, 1970.
Close, W.J. et al., "Synthesis of Potential Diuretic Agents. III. Derivatives of 6–Chloro–3, 4–dihydro–2–methyl–7–sulfamyl–2H–1,2,4–bendothiadiazine 1,1–Dioxide", *J. Org. Chem.*, 1961, 26, 3423–3427.
Short, J.H. et al. Synthesis of Potential Diuretic Agents. IV. Bromo Derivatives of 1,2,4–Benzothiadizine 1,1–Dioxide, *J. Org. Chem.* 1961, 26, 3428–3431.
Swett, L. et al., Synthesis of Potential Diuretic Agents. V. Dreivatives of New Tricyclic System, Benzo[1,2–3,5,4–e'] bis[2–methyl–3,4–dihydro–1,2,4–thiadiazine1,1–Dioxide], *J. Org. Chem.*, 1961, 26, 3431–3433.
Biressi, M.G. et al., "Derivati della Diidrobenzotiadianzina e del Tetraidro–4–Chinazolinone e loro Prodotti di Idrogenolisi", *Farmeco. Ed. Sci. (Italy).*, 1969, 24, 199–220.
Catsoulacos, P. et al., "Synthesis of Some N–Substituted 4,5–Dihydro–7,8–dimethoxybenzothiazepin–3–one 1,1–Dioxides", *J. Heterocyclic Chem.*, 1976, 13, 1309–1314.
Essien, H. et al., "Synthesis of Diethylenetriaminepentaacetic Acid Conjugated Inulin and Utility for Cellular Uptake of Liposomes", *J. Med. Chem.*, 1988, 31, 898–901.

Girard, Y. et al., "A New Synthesis of 1,2,4–Benzothiadiazines and a Selective Preparation of o–Aminobenzenesulphonamides", *J. Chem. Soc. Perkin I*, 1979, 1043–1047.
Harbeson, S.L. et al., "Stereospecific Synthesis of Peptidyl α–Keto Amides as Inhibitors of Calpain", *J. Med. Chem.*, 1994, 37, 2918–2929.
Hashizume, H. et al., "Synthesis and Biological Activity of New 3–Hydroxy–3–methylglutaryl Coenzyme–A (HMG––CoA) Synthase Inhibitors: 2–Oxetanones with a Side Chain Mimicking the Folded Structure of 1233A", *Chem. Pharm. Bull.*, 1994, 42, 512–520.
Hein,G.E. et al., "Steric Course and Specificity of α–Chymotrypsin–catalyzed Reactions. I.", *J. Am. Chem.Soc.*, 1962, 84, 4487–4494.
Lee, W.J. et al., "Factors Influencing the Binding of Calpain I", *Biochem. Internat.*, 1990, 22, 163–171.
Lehninger, *Biochemistry*, 1975, 2nd Ed., Worth Publishers, Inc., 73–75.
Lombardino, J.G. et al., "Synthesis and Antiinflammatory Activity of Some 3–Caboxamides of 2–Alkyl–4–hydroxy–2H–1,2–benzothiazine 1,1–Dioxide", *J. Med. Chem.*, 1971, 14, 1171–1177.
Lombardino, J.G. et al., "Potent Antiinflammatory N–Heterocyclic 3–Caboxamides of 4–Hydroxy–2–methyl–2H–1, 2–benzothiazine 1,1–Dioxide", *J. Med. Chem.*, 1973, 16, 493–496.
Maeda, H. et al., "Synthesis and Central Nervous System Actions of Thyrotropin–Releasing Hormone Analogs Containing a 1–Oxo–1,2,3,4–tetrahydroisoquinoline Moiety", *Chem.Pharm. Bull.*, 1988, 36, 190–201.
Ocain, T.D. et al., "α–Keto Amide Inhibitors of Aminopeptidases", *J. Med. Chem.*, 1992, 35, 451–456.
Pöpel, W. et al., "Derivate von 6,7–Dimethoxy–1 thiaisochroman–1,1–dioxid und 3,4–Dihydro–6, 7–Dimethoxy–2H–1,2–benzothiazin–1,1–dioxid", *Pharmazie*, 1980, 35, 266–278.
Wrobel, J. et al., "Synthesis of Spiro(Oxazolidinediones): Spiro [1H–Isoin–Dole–1,5'–Oxazolidine]–2',3(2H),4'–Triones and Spiro [1,2–Benz–Isothiazole–3(2H),5'–Oxazolidine]–2',4'–Dione 1,1–Dioxides", *Heterocycles*, 1994, 38, 1823–1838.

*Primary Examiner*—Cecilia J. Tsang
*Assistant Examiner*—David Lukton
*Attorney, Agent, or Firm*—Woodcock Washburn Kurtz Mackiewicz & Norris LLP

[57] ABSTRACT

The present invention is directed to novel benzothiazo and related heterocyclic group-containing inhibitors of cysteine or serine proteases. Methods for using the same are also described.

53 Claims, No Drawings

BENZOTHIAZO AND RELATED HETEROCYCLIC GROUP-CONTAINING CYSTEINE AND SERINE PROTEASE INHIBITORS

CROSS REFERENCE TO RELATED APPLICATIONS

This application claims benefit of U.S. Provisional Application Ser. No. 60/030,526, filed Nov. 13, 1996, the disclosure of which is hereby incorporated by reference in its entirety.

FIELD OF THE INVENTION

Novel benzothiazo and related heterocyclic group-containing inhibitors of cysteine or serine proteases, methods for making these novel compounds, and methods for using the same are disclosed.

BACKGROUND OF THE INVENTION

Numerous cysteine and serine proteases have been identified in human tissues. A "protease" is an enzyme which degrades proteins into smaller components (peptides). The terms "cysteine protease" and "serine protease" refer to proteases which are distinguished by the presence therein of a cysteine or serine residue which plays a critical role in the catalytic process. Mammalian systems, including humans, normally degrade and process proteins via a variety of enzymes including cysteine and serine proteases. However, when present at elevated levels or when abnormally activated, cysteine and serine proteases may be involved in pathophysiological processes.

For example, calcium-activated neutral proteases ("calpains") comprise a family of intracellular cysteine proteases which are ubiquitously expressed in mammalian tissues. Two major calpains have been identified; calpain I and calpain II. While calpain II is the predominant form in many tissues, calpain I is thought to be the predominant form in pathological conditions of nerve tissues. The calpain family of cysteine proteases has been implicated in many diseases and disorders, including neurodegeneration, stroke, Alzheimer's, amyotrophy, motor neuron damage, acute central nervous system injury, muscular dystrophy, bone resorption, platelet aggregation, cataracts and inflammation. Calpain I has been implicated in excitatory amino-acid induced neurotoxicity disorders including ischemia, hypoglycemia, Huntington's Disease, and epilepsy. The lysosomal cysteine protease cathepsin B has been implicated in the following disorders: arthritis, inflammation, myocardial infarction, tumor metastasis, and muscular dystrophy. Other lysosomal cysteine proteases include cathepsins C, H, L and S. Interleukin-1β converting enzyme ("ICE") is a cysteine protease which catalyzes the formation of interleukin-1β. Interleukin-1β is an immunoregulatory protein implicated in the following disorders: inflammation, diabetes, septic shock, rheumatoid arthritis, and Alzheimer's disease. ICE has also been linked to apoptotic cell death of neurons, which is implicated in a variety of neurodegenerative disorders including Parkinson's disease, ischemia, and amyotrophic lateral sclerosis (ALS).

Cysteine proteases are also produced by various pathogens. The cysteine protease clostripain is produced by *Clostridium histolyticum*. Other proteases are produced by *Trypanosoma cruzi*, malaria parasites *Plasmodium falciparum* and *P. vinckei* and Streptococcus. Hepatitis A viral protease HAV C3 is a cysteine protease essential for processing of picornavirus structural proteins and enzymes.

Exemplary serine proteases implicated in degenerative disorders include thrombin, human leukocyte elastase, pancreatic elastase, chymase and cathepsin G. Specifically, thrombin is produced in the blood coagulation cascade, cleaves fibrinogen to form fibrin and activates Factor VIII; thrombin is implicated in thrombophlebitis, thrombosis and asthma. Human leukocyte elastase is implicated in tissue degenerative disorders such as rheumatoid arthritis, osteoarthritis, atherosclerosis, bronchitis, cystic fibrosis, and emphysema. Pancreatic elastase is implicated in pancreatitis. Chymase, an enzyme important in angiotensin synthesis, is implicated in hypertension, myocardial infarction, and coronary heart disease. Cathepsin G is implicated in abnormal connective tissue degradation, particularly in the lung.

Given the link between cysteine and serine proteases and various debilitating disorders, compounds which inhibit these proteases would be useful and would provide an advance in both research and clinical medicine. The present invention is directed to these, as well as other, important ends.

SUMMARY OF THE INVENTION

The present invention is directed to novel cysteine and serine protease inhibitors which contain a benzoheterocyclic group. Exemplary compounds are represented by the following Formula I:

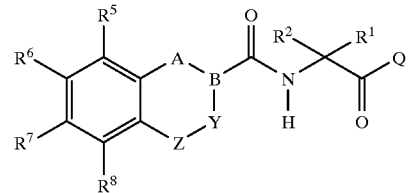

wherein:

A—B represents one, two, or three carbon atoms or nitrogen atoms, optionally connected by single bonds or one double bond, optionally substituted with one or more groups selected from $R^3$, $R^4$, $OR^3$, $OR^4$, $R^{4a}$, and $OR^{4a}$, with the proviso that the number of nitrogen atoms is 0, 1 or 2;

$R^1$ and $R^2$ are each independently hydrogen, alkyl having from one to about 14 carbons, cycloalkyl having from 3 to about 10 carbons, aryl having from about 6 to about 14 carbons, heteroaryl having from about 6 to about 14 ring atoms, aralkyl having from about 7 to about 15 carbons, heteroaralkyl, or an optionally protected natural or unnatural side chain of an amino acid, said alkyl, cycloalkyl, aryl, and heteroaryl groups being optionally substituted with one or more K groups;

$R^3$, $R^4$ and $R^{4a}$ are each independently hydrogen, lower alkyl, or a natural or unnatural side chain of an optionally protected amino acid, said alkyl groups being optionally substituted with an aryl or heteroaryl group;

$R^5$, $R^6$, $R^7$ and $R^8$ are each independently hydrogen, alkyl having from one to about 14 carbons wherein said alkyl groups are optionally substituted with one or more K groups, alkoxy having from one to about 10 carbons, halogen, alkoxycarbonyl, carboxyl, hydroxyl, heterocyclic, or amino optionally substituted with 1 to 3 aryl or lower alkyl groups;

or any two adjacent $R^5$, $R^6$, $R^7$ and $R^8$ groups taken together with any intervening atoms of the benzene ring to which they are attached form an alicyclic, aromatic, heterocyclic, or heteroaryl ring having 5 to 8 ring atoms;

K is halogen, lower alkyl, lower alkenyl, aryl, heterocyclic, guanidino, nitro, alkoxycarbonyl, alkoxy, hydroxyl, carboxyl, arylaminosulfonyl, heteroarylaminosulfonyl, alkylaminosulfonyl, or amino optionally substituted with an alkylsulfonyl, arylsulfonyl, or heteroarylsulfonyl group, or with 1 to 3 aryl or lower alkyl groups, said alkyl, aryl, and heteroaryl groups being optionally substituted with one or more G groups;

G is the same as K;

Y is O, NH, $NR^9$ or $CHR^9$;

Z is $S(=O)_3$, $S(=O)$, S, or $C(=O)$ j is 0, 1 or 2;

Q is hydrogen, $C(=O)$ $NHR^9$, $C(=O)OR^9$, $CH=N_2$, or $CH_2R^{10}$;

$R^9$ is hydrogen, alkyl having from one to about 10 carbons, said alkyl groups being optionally substituted with one or more K groups, aryl having from about 6 to about 14 carbons, or aralkyl having from about 7 to about 15 carbons;

$R^{10}$ is aryloxy, heteroaryloxy, L, halogen, or has the formula O—M, wherein M has the structure:

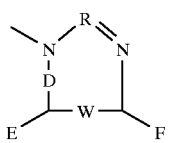

wherein:

R is N or $CR^{11}$;

W is a double bond or a single bond;

D is C=O or a single bond;

E and F are independently $R^{12}$, $R^{13}$, or J;

or E and F taken together comprise a joined moiety, said joined moiety being an aliphatic carbocyclic ring optionally substituted with J and having from 5 to 7 carbons, an aromatic carbocyclic ring optionally substituted with J and having from 5 to 7 carbons, an aliphatic heterocyclic ring optionally substituted with J and having from 5 to 7 atoms, or an aromatic heterocyclic ring optionally substituted with J and having from 5 to 7 atoms, said aliphatic heterocyclic ring or said aromatic heterocyclic ring each having from 1 to 4 heteroatoms;

$R^{11}$, $R^{12}$, and $R^{13}$ are independently H, alkyl having from 1 to 10 carbons, heteroaryl having from 1 to 10 carbons, alkanoyl having from 1 to 10 carbons, or aroyl, wherein said alkyl, heteroaryl, alkanoyl and aroyl groups are optionally substituted with J;

J is halogen, $C(=O)OR^{14}$, $R^4OC(=O)$, $R^{14}OC(=O)NH$, OH, CN, $NO_2$, $NR^{14}R^{15}$, $N=C(R^4)R^{15}$, $N=C(NR^{14}R^{15})_2$, $SR^{14}$ $OR^{14}$, phenyl, napthyl, heteroaryl, or a cycloalkyl group having from 3 to 8 carbons;

$R^{14}$ and $R^{15}$ are independently H, alkyl having from 1 to 10 carbons, aryl, or heteroaryl, wherein said alkyl, aryl and heteroaryl groups are optionally substituted with K;

L is a phosphorus-containing enzyme reactive group having the formula:

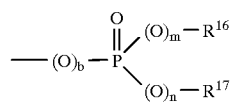

wherein:

m, n, and b are each independently 0 or 1;

$R^{16}$ and $R^{17}$ are each independently hydrogen, lower alkyl optionally substituted with K, aryl optionally substituted with K, or heteroaryl optionally substituted with K;

or $R^{16}$ and $R^{17}$ taken together with —(O)$_n$—P(=O)—(O)$_m$— can form a 5–8 membered ring containing up to 3 hetero atoms;

or $R^{16}$ and $R^{17}$ taken together with —(O)$_n$—P(=O)—(O)$_m$— can form a 5–8 membered ring optionally substituted with K;

or a pharmaceutically acceptable salt or bisulfite addition product thereof.

The compounds of the invention are useful for the inhibition of cysteine and serine proteases. Beneficially, the compounds find utility in a variety of settings. For example, in a research arena, the claimed compounds can be used, for example, as standards to screen for natural and synthetic cysteine protease and serine protease inhibitors which have the same or similar functional characteristics as the disclosed compounds. In a clinical arena, the compounds of the present invention can be used to alleviate, mediate, reduce and/or prevent disorders which are associated with abnormal and/or aberrant activity of cysteine proteases and/or serine proteases. Accordingly, methods for using the subject compounds, such as methods for inhibiting serine proteases or cysteine proteases comprising contacting said proteases with an inhibitory amount of a compound of the invention are disclosed. Methodologies for making the benzothiazine group-containing inhibitors are also disclosed. These and other features of the compounds of the subject invention are set forth in more detail below.

DETAILED DESCRIPTION

Novel cysteine and serine protease inhibitors have been discovered which are represented by the general Formula I:

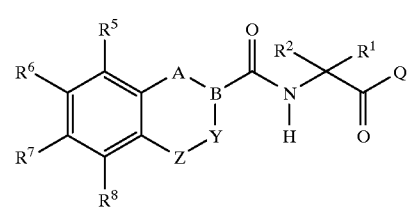

wherein:

A—B represents one, two, or three carbon atoms or nitrogen atoms, optionally connected by single bonds or one double bond, optionally substituted with one or more groups selected from $R^3$, $R^4$, $OR^3$, $OR^4$, $R^{4a}$, and $OR^{4a}$, with the proviso that the number of nitrogen atoms is 0, 1 or 2;

$R^1$ and $R^2$ are each independently hydrogen, alkyl having from one to about 14 carbons, cycloalkyl having from 3 to about 10 carbons, aryl having from about 6 to about 14 carbons, heteroaryl having from about 6 to about 14 ring atoms, aralkyl having from about 7 to about 15 carbons, heteroaralkyl, or an optionally protected natural or unnatural side chain of an amino acid, said alkyl, cycloalkyl, aryl, and heteroaryl groups being optionally substituted with one or more K groups;

$R^3$, $R^4$ and $R^{4a}$ are each independently hydrogen, lower alkyl, or a natural or unnatural side chain of an optionally protected amino acid, said alkyl groups being optionally substituted with an aryl or heteroaryl group;

$R^5$, $R^6$, $R^7$ and $R^8$ are each independently hydrogen, alkyl having from one to about 14 carbons wherein said alkyl groups are optionally substituted with one or more K groups, alkoxy having from one to about 10 carbons, halogen, alkoxycarbonyl, carboxyl, hydroxyl, heterocyclic, or amino optionally substituted with 1 to 3 aryl or lower alkyl groups;

or any two adjacent $R^5$, $R^6$, $R^7$ and $R^8$ groups taken together with any intervening atoms of the benzene ring to which they are attached form an alicyclic, aromatic, heterocyclic, or heteroaryl ring having 5 to 8 ring atoms;

K is halogen, lower alkyl, lower alkenyl, aryl, heterocyclic, guanidino, nitro, alkoxycarbonyl, alkoxy, hydroxyl, carboxyl, arylaminosulfonyl, heteroarylaminosulfonyl, alkylaminosulfonyl, or amino optionally substituted with an alkylsulfonyl, arylsulfonyl, or heteroarylsulfonyl group, or with 1 to 3 aryl or lower alkyl groups, said alkyl, aryl, and heteroaryl groups being optionally substituted with one or more G groups;

G is the same as K;

Y is O, NH, $NR^9$ or $CHR^9$;

Z is $S(=O)_2$, $S(=O)$, S, or $C(=O)$;

j is 0, 1 or 2;

Q is hydrogen, $C(=O)NHR^9$, $C(=O)OR^9$, $CH=N_2$, or $CH_2R^{10}$;

$R^9$ is hydrogen, alkyl having from one to about 10 carbons, said alkyl groups being optionally substituted with one or more K groups, aryl having from about 6 to about 14 carbons, or aralkyl having from about 7 to about 15 carbons;

$R^{10}$ is aryloxy, heteroaryloxy, L, halogen, or has the formula O—M, wherein M has the structure:

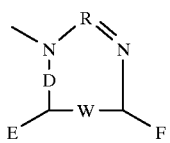

wherein:

R is N or $CR^{11}$;

W is a double bond or a single bond;

D is C=O or a single bond;

E and F are independently $R^{12}$, $R^{13}$, or J;

or E and F taken together comprise a joined moiety, said joined moiety being an aliphatic carbocyclic ring optionally substituted with J and having from 5 to 7 carbons, an aromatic carbocyclic ring optionally substituted with J and having from 5 to 7 carbons, an aliphatic heterocyclic ring optionally substituted with J and having from 5 to 7 atoms, or an aromatic heterocyclic ring optionally substituted with J and having from 5 to 7 atoms, said aliphatic heterocyclic ring or said aromatic heterocyclic ring each having from 1 to 4 heteroatoms;

$R^{11}$, $R^{12}$, and $R^{13}$ are independently H, alkyl having from 1 to 10 carbons, heteroaryl having from 1 to 10 carbons, alkanoyl having from 1 to 10 carbons, or aroyl, wherein said alkyl, heteroaryl, alkanoyl and aroyl groups are optionally substituted with J;

J is halogen, $C(=O)OR^{14}$, $R^{14}OC(=O)$, $R^{14}OC(=O)NH$, OH, CN, $NO_2$, $NR^{14}R^{15}$, $N=C(R^{14})R^{15}$, $N=C(NR^{14}R^{15})_2$, $SR^{14}$, $OR^{14}$, phenyl, naphthyl, heteroaryl, or a cycloalkyl group having from 3 to 8 carbons;

$R^{14}$ and $R^{15}$ are independently H, alkyl having from 1 to 10 carbons, aryl, or heteroaryl, wherein said alkyl, aryl and heteroaryl groups are optionally substituted with K;

L is a phosphorus-containing enzyme reactive group having the formula:

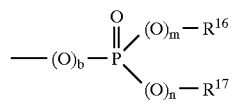

wherein:

m, n, and b are each independently 0 or 1;

$R^{16}$ and $R^{17}$ are each independently hydrogen, lower alkyl optionally substituted with K, aryl optionally substituted with K, or heteroaryl optionally substituted with K;

or $R^{16}$ and $R^{17}$ taken together with —$(O)_n$—P(=O)—$(O)_m$— can form a 5–8 membered ring containing up to 3 hetero atoms;

or $R^{16}$ and $R^{17}$ taken together with —$(O)_n$—P(=O)—$(O)_m$— can form a 5–8 membered ring optionally substituted with K;

or a pharmaceutically acceptable salt or bisulfite addition product thereof.

It is recognized that various stereoisomeric forms of the compounds of Formula I may exist. All such racemates, diastereomers, individual enantiomers, and mixtures thereof form part of the present invention. In some preferred embodiments of the compounds of the invention where $R^2$ is H, it is preferred that the carbon to which the substituent $R^1$ is attached have the L-configuration.

In some preferred embodiments of the compounds of Formula I, A—B is —[CH($R^4$)]$_j$—C($R^3$)—, —C($R^4$)=C—, —CH(O$R^4$) —C($R^3$)—, —C(O$R^4$)=C—, —N($R^4$)—C($R^3$)—, —N=C—, —C($R^{4a}$)=C($R^4$)—C($R^3$)—, or —CH($R^{4a}$)—C($R^4$)=C— where j is 0, 1, or 2. In more preferred embodiments A—B is —[CH($R^4$)]$_j$—C($R^3$)— where j is 1, —C($R^4$)=C—, —N($R^4$)—C($R^3$)—, or —N=C—, preferably where $R^3$ and $R^4$ are each H.

In some preferred embodiments of the compounds of Formula I, Z is $SO_2$ or C(=O), with $SO_2$ being preferred.

In further preferred embodiments of the compounds of Formula I, $R^2$, $R^5$ and $R^8$ are each H. In still further preferred embodiments $R^1$ is alkyl or aralkyl, preferably i-butyl or benzyl.

In preferred embodiments of the compounds of formula I, $R^6$ and $R^7$ are independently H, alkoxy, halogen, or heterocyclic, or $R^6$ and $R^7$ taken together form —O—$CH_2$—$CH_2$—O—. In more preferred embodiments $R^6$ and $R^7$ are independently H, —$OCH_3$, F, Cl, or morpholin-4-yl, or $R^6$ and $R^7$ taken together form —O—$CH_2$—$CH_2$—O—.

In some preferred embodiments of the compounds of Formula I, Q is H, $C(=O)NHR^9$, or $C(=O)OR^9$, where $R^9$ is alkyl or alkyl substituted with K. In further preferred embodiments of the compounds of Formula I, Y is O, NH, NR$^9$ or CHR$^9$, where R$^9$ is alkyl or aralkyl. Preferably, Y is NR$^9$ or CHR$^9$, where R$^9$ is methyl ethyl, i-propyl, i-butyl or benzyl.

In particularly preferred embodiments of the compounds of Formula I, A—B is —[CH(R$^4$)]$_j$—C(R$^3$)— with —CH$_2$—CH— being preferred, —C(R$^4$)=C—, —N(R$^4$)—C(R$^3$)—, or —N=C—; Z is SO$_2$ or C(=O) with SO$_2$ being preferred; R$^2$, R$^5$ and R$^8$ are each H; R$^1$ is alkyl or aralkyl, with i-butyl or benzyl being preferred; R$^6$ and R$^7$ are independently H, alkoxy, halogen, or heterocyclic, or R$^6$ and R$^7$ taken together form —O—CH$_2$—CH$_2$—O—; Q is H, C(=O)NHR$^9$, or C(=O)OR$^9$, where R$^9$ is alkyl or alkyl substituted with K; and Y is O, NH, NR$^9$ or CHR$^9$, where R$^9$ is alkyl or aralkyl. In these preferred embodiments R$^6$ and R$^7$ are preferably independently H, —OCH$_3$, F, Cl, or morpholin-4-yl, or R$^6$ and R$^7$ taken together form —O—CH$_2$—CH$_2$—O—, and Y is preferably NR$^9$ or CHR$^9$, where R$^9$ is methyl ethyl, i-propyl, i-butyl or benzyl.

In some preferred embodiments of the compounds of Formula I, A—B is —CH$_2$—CH—; Z is SO$_2$; R$^2$, R$^5$ and R$^8$ are each H; and
- R$^1$ is alkyl, alkyl substituted with K, or aralkyl, with i-butyl, benzyl, or alkyl substituted with phenylsulfonyl-amino being preferred;
- R$^6$ and R$^7$ are independently H, alkoxy, halogen, or heterocyclic, with H, OCH$_3$, F, Cl, or morpholin-4-yl being preferred, or preferably R$^6$ and R$^7$ taken together form —O—CH$_2$—CH$_2$—O—;
- Q is H, C(=O)NHR$^9$, or C(=O)OR$^9$, where R$^9$ is alkyl, preferably methyl, ethyl, or butyl; and Y is O, NH or NR$^9$ where R$^9$ is alkyl or aralkyl, with methyl, ethyl, propyl, butyl or benzyl being preferred.

In especially preferred embodiments, A—B is —CH$_2$—CH—; Z is SO$_2$; R$^2$, R$^5$ and R$^8$ are each H; and R$^1$, R$^6$, R$^7$, Y and Q have the values shown in Table II, infra.

In further preferred embodiments of the compounds of Formula I, A—B is —CH$_2$—CH—; Z is SO$_2$; R$^2$, R$^5$ and R$^8$ are each H; R$^6$ and R$^7$ taken together form —O—CH$_2$—CH$_2$—O—; R$^1$ is benzyl; Y is N—H or N-ethyl; and Q is C(=O)NHR$^9$ where R$^9$ is alkyl or alkyl substituted with K, preferably CONHEt, CONHBu, CONHCH$_2$CH$_2$OCH$_3$, CONHCH(CH$_3$)$_2$, CONH(CH$_2$)$_4$CH$_3$, CONHCH$_2$Ph, CONHCH$_2$CH$_2$Ph, CONHCH$_2$CH=CH$_2$, CONH(CH$_2$)$_3$-(imidazol-1-yl), CONH(CH$_2$)$_3$-(2-ketopyrrolidin-1-yl), CONH(CH$_2$)$_3$(morpholin-4-yl), CONHCH$_2$(pyridin-2-yl), CONHCH$_2$-cyclopropane, CONHCH$_2$CH$_2$NHSO$_2$CH$_3$, CONHCH$_2$CH$_2$NHSO$_2$(4-NO$_2$-Ph), CONH(CH$_2$)$_3$NHSO$_2$(4-NO$_2$-Ph), CONHCH$_2$CH$_2$NHSO$_2$(3,4-Cl$_2$-Ph) CONH(CH$_2$)$_3$NHSO$_2$(3,4-Cl$_2$-Ph), CONHCH$_2$CH$_2$NHSO$_2$Ph, CONHCH$_2$CH$_2$NHSO$_2$(5-(2-pyridinyl)-thiophen-2-yl), CONH(CH$_2$)$_3$NHSO$_2$(4-F-Ph), CONH(CH$_2$)$_3$NHSO$_2$Ph, CONHCH$_2$-(pyridin-4-yl), or CONHCH$_2$CH$_2$NHSO$_2$(4-F-Ph).

In especially preferred embodiments, A—B is —CH$_2$—CH—; Z is SO$_2$; R$^2$, R$^5$ and R$^8$ are each H; R$^6$ and R$^7$ taken together form —O—CH$_2$—CH$_2$—O—; R$^1$ is benzyl; and Y and Q have the values shown in Table III, infra.

In further preferred embodiments of the compounds of Formula I, A—B is —C(R$^4$)=C—; Z is SO$_2$; R$^2$, R$^5$ and R$^8$ are each H; R$^1$ is benzyl; R$^6$ and R$^7$ are independently H or halogen, or R$^6$ and R$^7$ taken together form —O—CH$_2$—CH$_2$—O—; R$^4$ is H, alkoxy with methoxy being preferred, or hydroxy; Y is NR$^9$ wherein R$^9$ is alkyl with methyl and ethyl being preferred; and Q is H or C(=O)NHR$^9$ where R$^9$ is alkyl, preferably butyl.

In especially preferred embodiments, A—B is —C(R$^4$)=C—; Z is SO$_2$; R$^2$, R$^5$ and R$^8$ are each H; and R$^1$, R$^6$, R$^7$, R$^4$, Y and Q have the values shown in Table IV, infra.

In further preferred embodiments of the compounds of Formula I, A—B is —N(R$^4$)—CH— where R$^4$ is preferably H, propyl, or benzyl; Z is SO$_2$; R$^2$, R$^5$ and R$^8$ are each H; R$^1$ is benzyl; R$^6$ and R$^7$ are each H; Y is N—R$^9$ where R$^9$ is alkyl, preferably methyl or ethyl; and Q is H or C(=O)NHR$^9$ where R$^9$ is alkyl, preferably butyl.

In especially preferred embodiments, A—B is —N(R$^4$)—CH—; Z is SO$_2$; R$^2$, R$^5$ and R$^8$ are each H; R$^1$ is benzyl; R$^6$ and R$^7$ are each H; Y is N—R$^9$; and R$^4$, R$^9$ and Q have the values shown in Table V, infra.

In further preferred embodiments of the compounds of Formula I, A—B is —N=C—; Z is SO$_2$; Y is NH; R$^2$, R$^5$ and R$^8$ are each H; R$^1$ is benzyl and R$^6$ and R$^7$ are each H, or R$^6$ and R$^7$ taken together form —O—CH$_2$—CH$_2$—O—; and Q is H or C(=O)NHR$^9$ where R$^9$ is alkyl, preferably butyl.

In especially preferred embodiments, A—B is —N=C—; Z is SO$_2$; Y is NH; R$^2$, R$^5$ and R$^8$ are each H; R$^1$ is benzyl and R$^6$, R$^7$ and Q have the values shown in Table VI, infra.

In further preferred embodiments of the compounds of Formula I, A—B is —CH$_2$—CH—; Z is C(=O); R$^2$, R$^5$ and R$^8$ are each H; R$^1$ is benzyl; R$^6$ and R$^7$ are each H; Q is H; Y is N—R$^9$ where R$^9$ is H or alkyl, preferably methyl.

In some preferred embodiments, compounds of the invention have the formula:

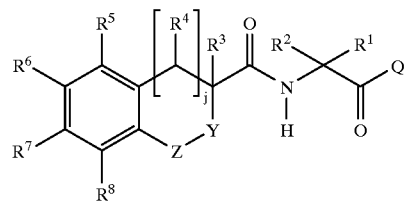

wherein the constituent variables are as defined above.

When Q is hydrogen, the invention includes the bisulfite addition products of the aldehydes of Formula I, as exemplified in Example 187, infra.

As used herein, the term "alkyl" is meant to include straight-chain, branched and cyclic hydrocarbon groups such as, for example, ethyl, isopropyl and cyclopropyl groups. Preferred alkyl groups have 1 to about 10 carbon atoms. "Cycloalkyl" groups are cyclic alkyl groups. "Aryl" groups are aromatic cyclic compounds including but not limited to phenyl, naphthyl, anthracyl, phenanthryl, and pyrenyl. Also included within the definition of "aryl" are ring systems having two aromatic rings connected by a bond, such as biphenyl. Preferred aryl groups include phenyl and naphthyl. The term "carbocyclic", as used herein, refers to cyclic groups in which the ring portion is composed solely of carbon atoms. The term "hetero" denotes the presence of one or more noncarbon atoms. Thus, the term "heterocyclic" refers to cyclic groups in which the ring portion includes at least one heteroatom such as O, N or S. "Heteroalkyl" groups are heterocycles containing solely single bonds within their ring portions, i.e. saturated heteroatomic ring systems. The term "lower alkyl" refers to alkyl groups of 1–4 carbon atoms. The term "halogen" refers to F, Cl, Br, and I atoms.

The term "aralkyl" denotes alkyl groups which bear aryl groups, for example, benzyl groups. The term "heteroaryl" denotes aryl groups having one or more heteroatoms (e.g., O, N, or S) contained within an aromatic ring. "Heteroaralkyl" groups are aralkyl groups which have one or more heteroatoms in their aromatic ring portion. Also included within the definition of "heteroaryl" are ring systems having two aromatic rings connected by a bond, where at least one of the rings contains a hetero atom.

As used herein, "alkoxy" groups are alkyl groups linked through an oxygen atom. Examples of alkoxy groups include methoxy (—OCH$_3$) and ethoxy (—OCH$_2$CH$_3$) groups. Alkoxycarbonyl groups are carbonyl groups which contain an alkoxy substituent, i.e., groups of general formula —C(=O)—O—R, where R is alkyl. As used herein the term "alkanoyl" denotes an alkyl group attached through a carbonyl group, i.e., —C(=O)—R where R is alkyl. The term "aroyl" analogously denotes an aryl group attached through a carbonyl group.

As used herein, the term "alkenyl" is intended to include straight-chain or branched hydrocarbon chains having at least one carbon—carbon double bond. Examples of alkenyl groups include ethenyl groups and propenyl groups.

As used herein, the term "amino acid" denotes a molecule containing both an amino group and a carboxyl group. As used herein the term "L-amino acid" denotes an α-amino acid having the L configuration around the α-carbon, that is, a carboxylic acid of general formula CH(COOH) (NH$_2$)—(sidechain), having the L-configuration. Sidechains of L-amino acids include naturally occurring and non-naturally occurring moieties. Nonnaturally occurring amino acid sidechains are moieties that are used in place of naturally occurring amino acid sidechains in, for example, amino acid analogs. See, for example, Lehninger, *Biochemistry*, Second Edition, Worth Publishers, Inc, 1975, pages 73–75. Representative α-amino acid sidechains are shown below in Table 1.

TABLE 1

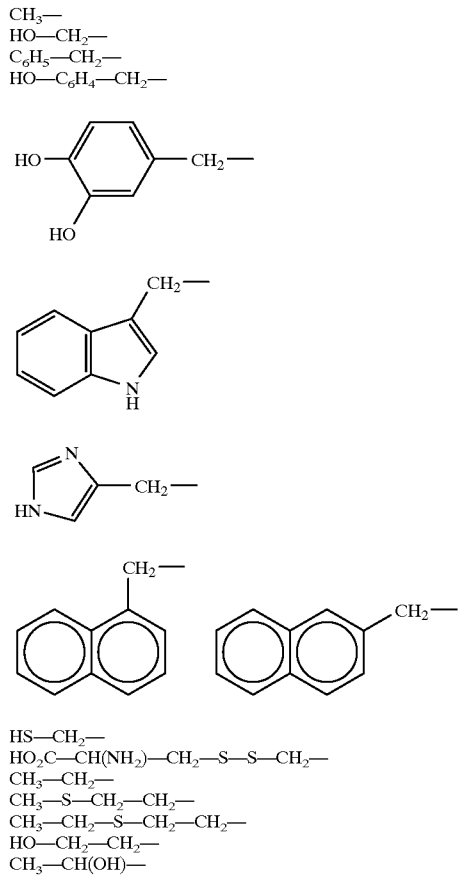

CH$_3$—
HO—CH$_2$—
C$_6$H$_5$—CH$_2$—
HO—C$_6$H$_4$—CH$_2$—

HS—CH$_2$—
HO$_2$C—CH(NH$_2$)—CH$_2$—S—S—CH$_2$—
CH$_3$—CH$_2$—
CH$_3$—S—CH$_2$—CH$_2$—
CH$_3$—CH$_2$—S—CH$_2$—CH$_2$—
HO—CH$_2$—CH$_2$—
CH$_3$—CH(OH)—

TABLE 1-continued

HO$_2$C—CH$_2$—NHC(=O)—CH$_2$—

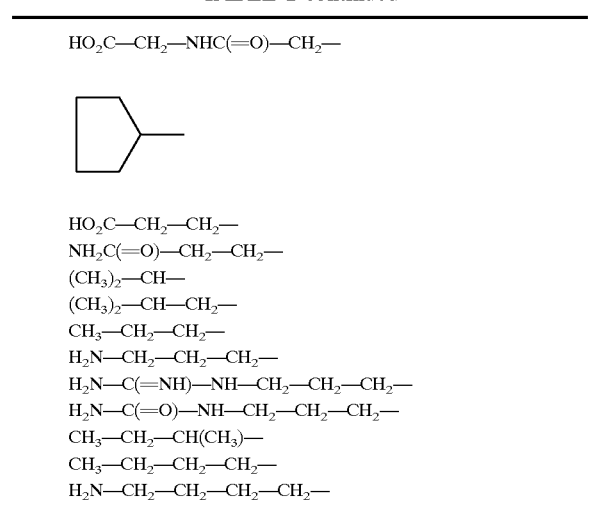

HO$_2$C—CH$_2$—CH$_2$—
NH$_2$C(=O)—CH$_2$—CH$_2$—
(CH$_3$)$_2$—CH—
(CH$_3$)$_2$—CH—CH$_2$—
CH$_3$—CH$_2$—CH$_2$—
H$_2$N—CH$_2$—CH$_2$—CH$_2$—
H$_2$N—C(=NH)—NH—CH$_2$—CH$_2$—CH$_2$—
H$_2$N—C(=O)—NH—CH$_2$—CH$_2$—CH$_2$—
CH$_3$—CH$_2$—CH(CH$_3$)—
CH$_3$—CH$_2$—CH$_2$—CH$_2$—
H$_2$N—CH$_2$—CH$_2$—CH$_2$—CH$_2$—

Functional groups present on the compounds of Formula I may contain blocking groups. Blocking groups are known per se as chemical functional groups that can be selectively appended to functionalities, such as hydroxyl groups, amino groups, thio groups and carboxyl groups. Protecting groups are blocking groups that can be readily removed from functionalities. These groups are present in a chemical compound to render such functionality inert to chemical reaction conditions to which the compound is exposed. Any of a variety of protecting groups may be employed with the present invention. One such protecting group is the benzyloxycarbonyl (Cbz; Z) group. Other protecting groups include toluenesulfonyl, t-butoxycarbonyl, methyl ester and benzyl ether groups. Other preferred protecting groups according to the invention may be found in Greene, T. W. and Wuts, P. G. M., "Protective Groups in Organic Synthesis" 2d. Ed., Wiley & Sons, 1991, which is incorporated herein by reference. Further blocking groups useful in the compounds of the present invention include the phthalimido group, arylcarbonyls, alkylcarbonyls, alkoxycarbonyls, aryloxycarbonyls, aralkyloxycarbonyls, alkyl- and aralkylsulfonyls, and arylsulfonyl groups such as those which have the following formulas:

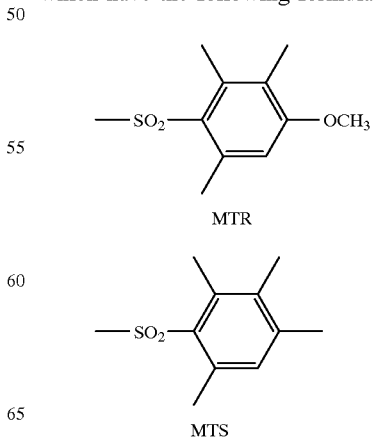

MTR

MTS

-continued

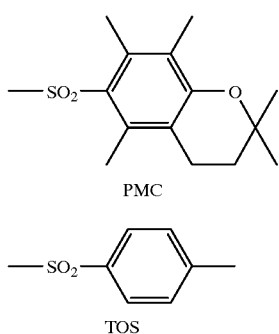

PMC

—SO₂—⟨benzene⟩—

TOS

Because the benzothiazo and related heterocyclic group-containing components of the invention inhibit cysteine proteases and serine proteases, they can be used in both research and therapeutic settings.

In a research environment, preferred compounds having defined attributes can be used to screen for natural and synthetic compounds which evidence similar characteristics in inhibiting protease activity. The compounds can also be used in the refinement of in vitro and in vivo models for determining the effects of inhibition of particular proteases on particular cell types or biological conditions. In a therapeutic setting, given the connection between cysteine proteases and certain defined disorders, and serine proteases and certain defined disorders, compounds of the invention can be utilized to alleviate, mediate, reduce and/or prevent disorders which are associated with abnormal and/or aberrant activity of cysteine proteases and/or serine proteases.

In preferred embodiments, compositions are provided for inhibiting a serine protease or a cysteine protease comprising a compound of the invention. In other preferred embodiments, methods are provided for inhibiting serine proteases or cysteine proteases comprising contacting a protease selected from the group consisting of serine proteases and cysteine proteases with an inhibitory amount of a compound of the invention.

The disclosed compounds of the invention are useful for the inhibition of cysteine proteases and serine proteases. As used herein, the terms "inhibit" and "inhibition" mean having an adverse effect on enzymatic activity. An inhibitory amount is an amount of a compound of the invention effective to inhibit a cysteine and/or serine protease.

Pharmaceutically acceptable salts of the cysteine and serine protease inhibitors also fall within the scope of the compounds as disclosed herein. The term "pharmaceutically acceptable salts" as used herein means an inorganic acid addition salt such as hydrochloride, sulfate, and phosphate, or an organic acid addition salt such as acetate, maleate, fumarate, tartrate, and citrate. Examples of pharmaceutically acceptable metal salts are alkali metal salts such as sodium salt and potassium salt, alkaline earth metal salts such as magnesium salt and calcium salt, aluminum salt, and zinc salt. Examples of pharmaceutically acceptable organic amine addition salts are salts with morpholine and piperidine. Examples of pharmaceutically acceptable amino acid addition salts are salts with lysine, glycine, and phenylalanine.

Compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, transdermal patches; or prepared in other suitable fashions for these and other forms of administration as will be apparent to those skilled in the art.

The composition may conveniently be administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for transdermal patches are preferably lipophilic emulsions.

The materials for this invention can be employed as the sole active agent in a pharmaceutical or can be used in combination with other active ingredients which could facilitate inhibition of cysteine and serine proteases in diseases or disorders.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in effective inhibitory amounts in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day. Such formulations typically provide inhibitory amounts of the compound of the invention. The preferred dosage of drug to be administered is likely, however, to depend on such variables as the type or extent of progression of the disease or disorder, the overall health status of the particular patient, the relative biological efficacy of the compound selected, and formulation of the compound excipient, and its route of administration.

As used herein, the term "contacting" means directly or indirectly causing at least two moieties to come into physical association with each other. Contacting thus includes physical acts such as placing the moieties together in a container, or administering moieties to a patient. Thus, for example administering a compound of the invention to a human patient evidencing a disease or disorder associated with abnormal and/or aberrant activity of such proteases falls within the scope of the definition of the term "contacting".

The invention is further illustrated by way of the following examples which are intended to elucidate the invention. These examples are not intended, nor are they to be construed, as limiting the scope of the disclosure.

EXAMPLES

Compounds of the invention were prepared according to the following procedures.

The synthesis of these compounds are summarized in Schemes 1–7:

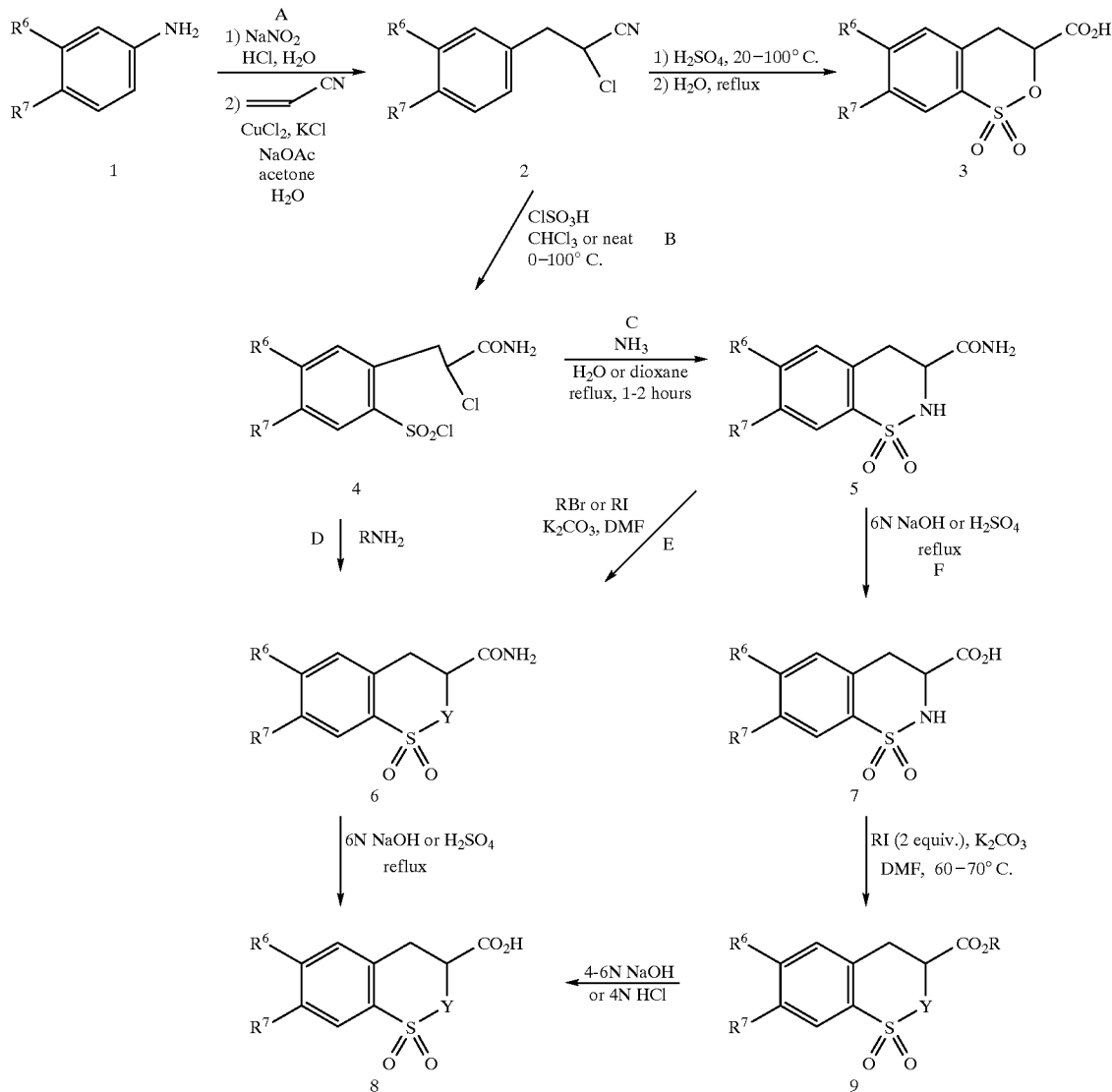

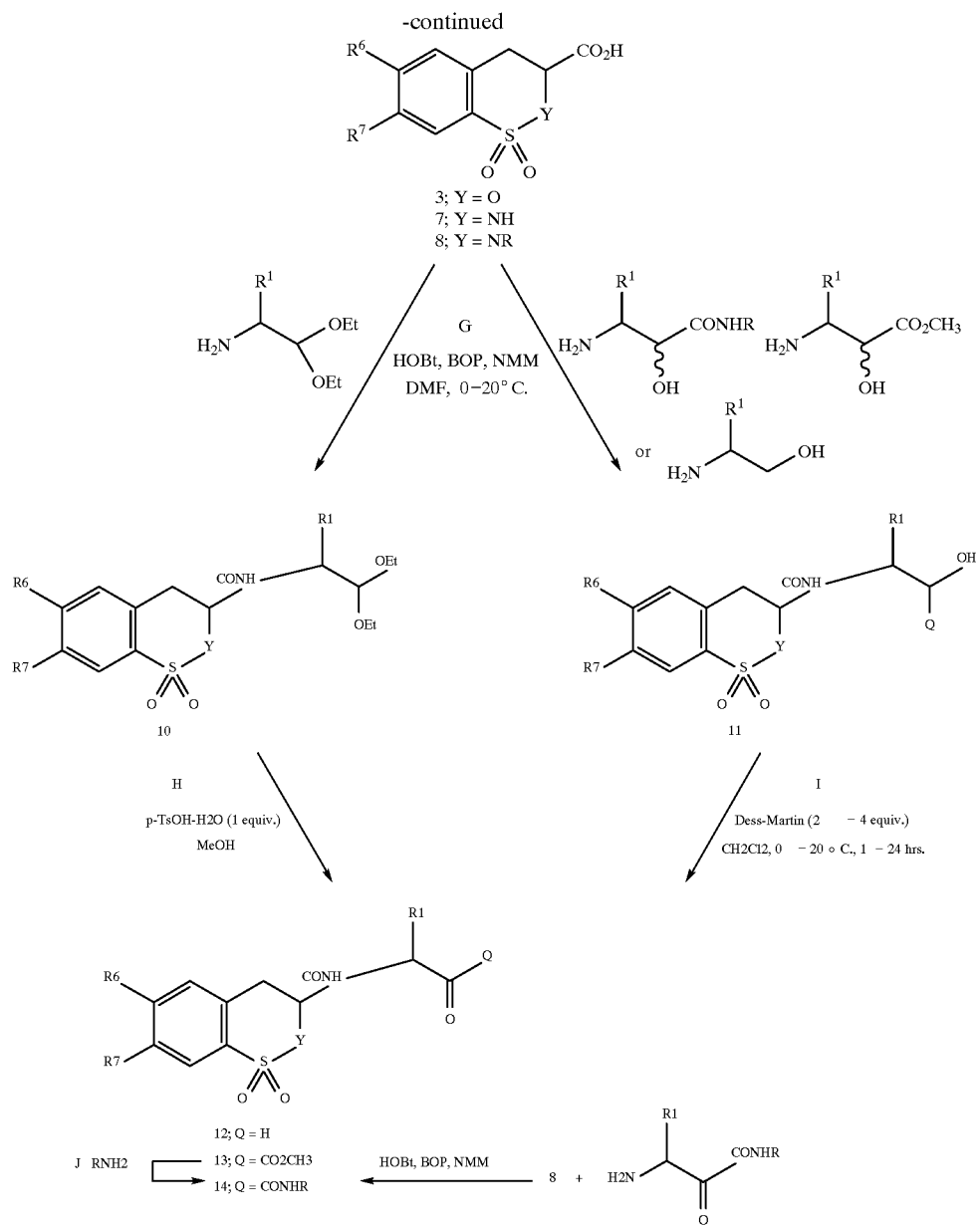
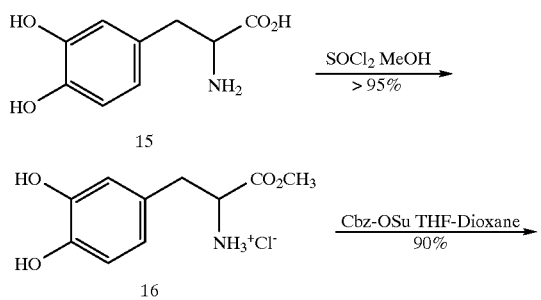
Scheme 2
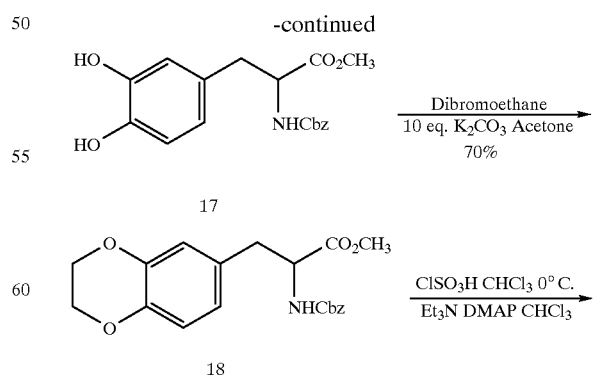

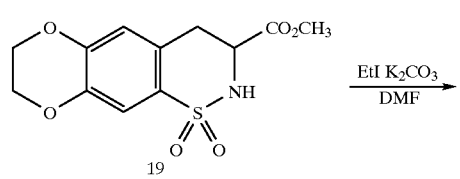
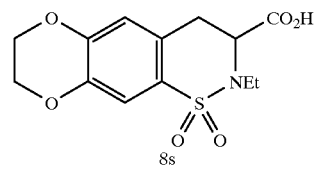
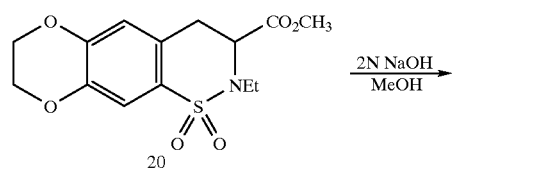
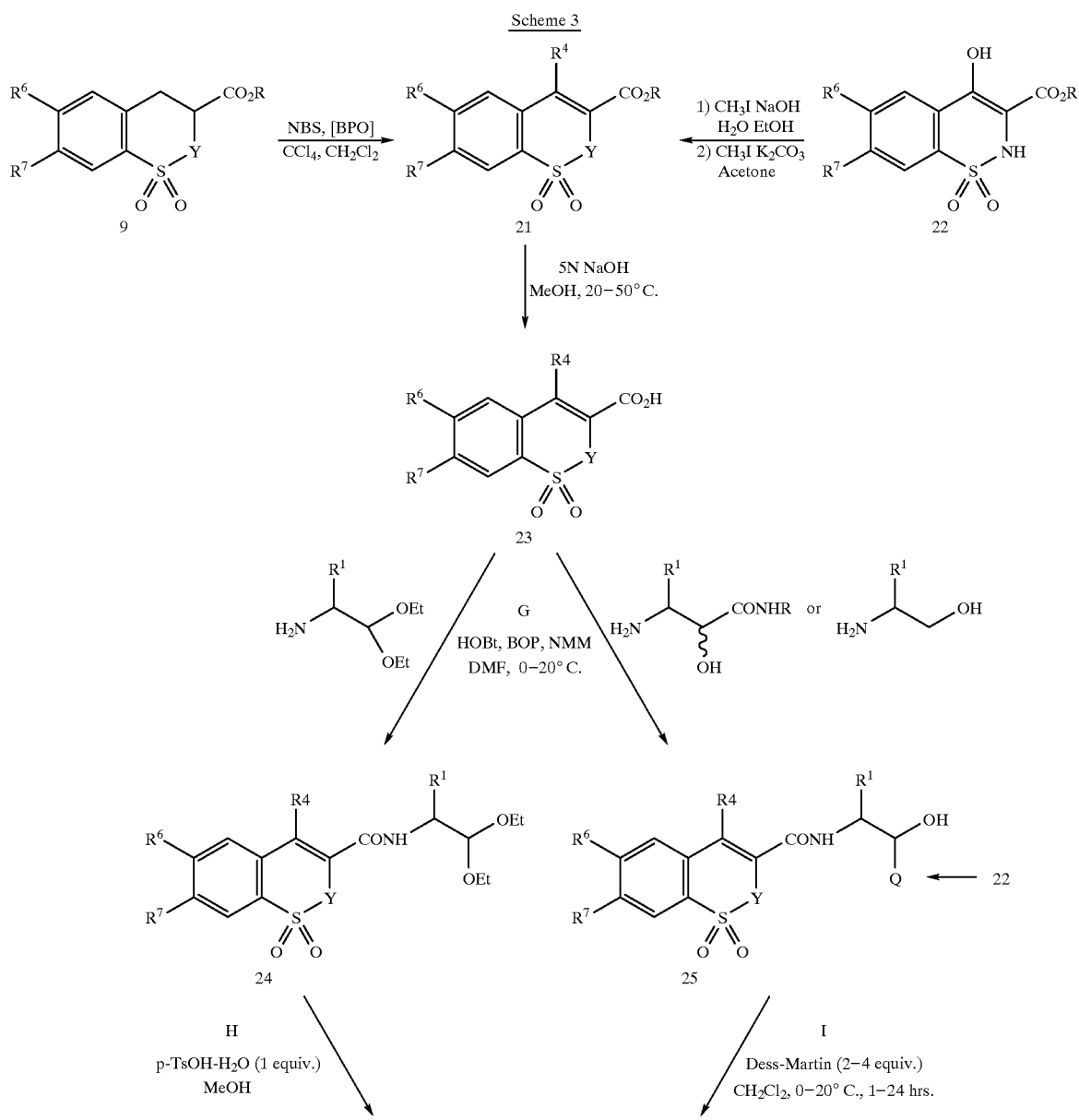

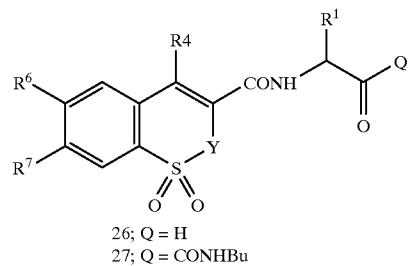
26; Q = H
27; Q = CONHBu
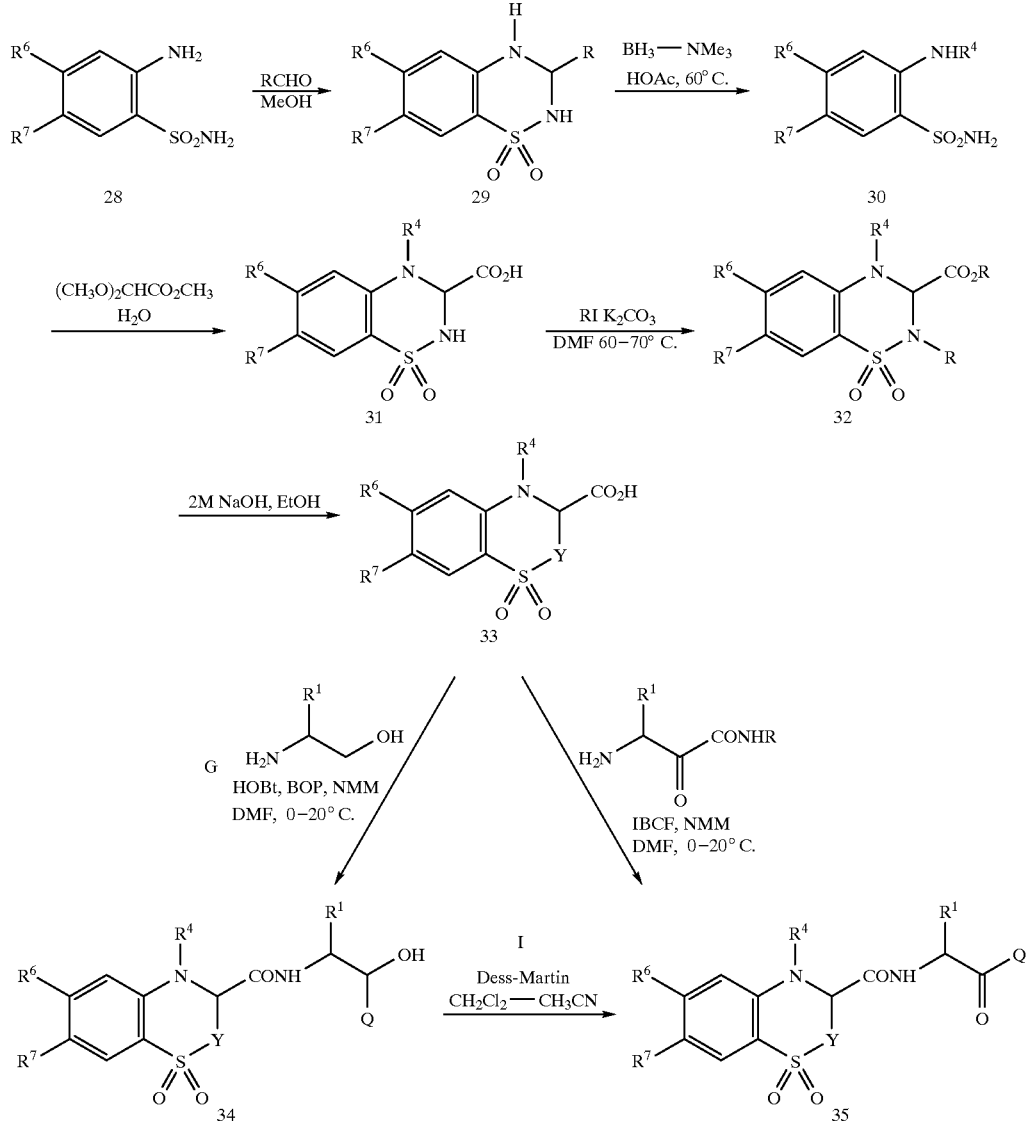
Scheme 4

SCHEME 5
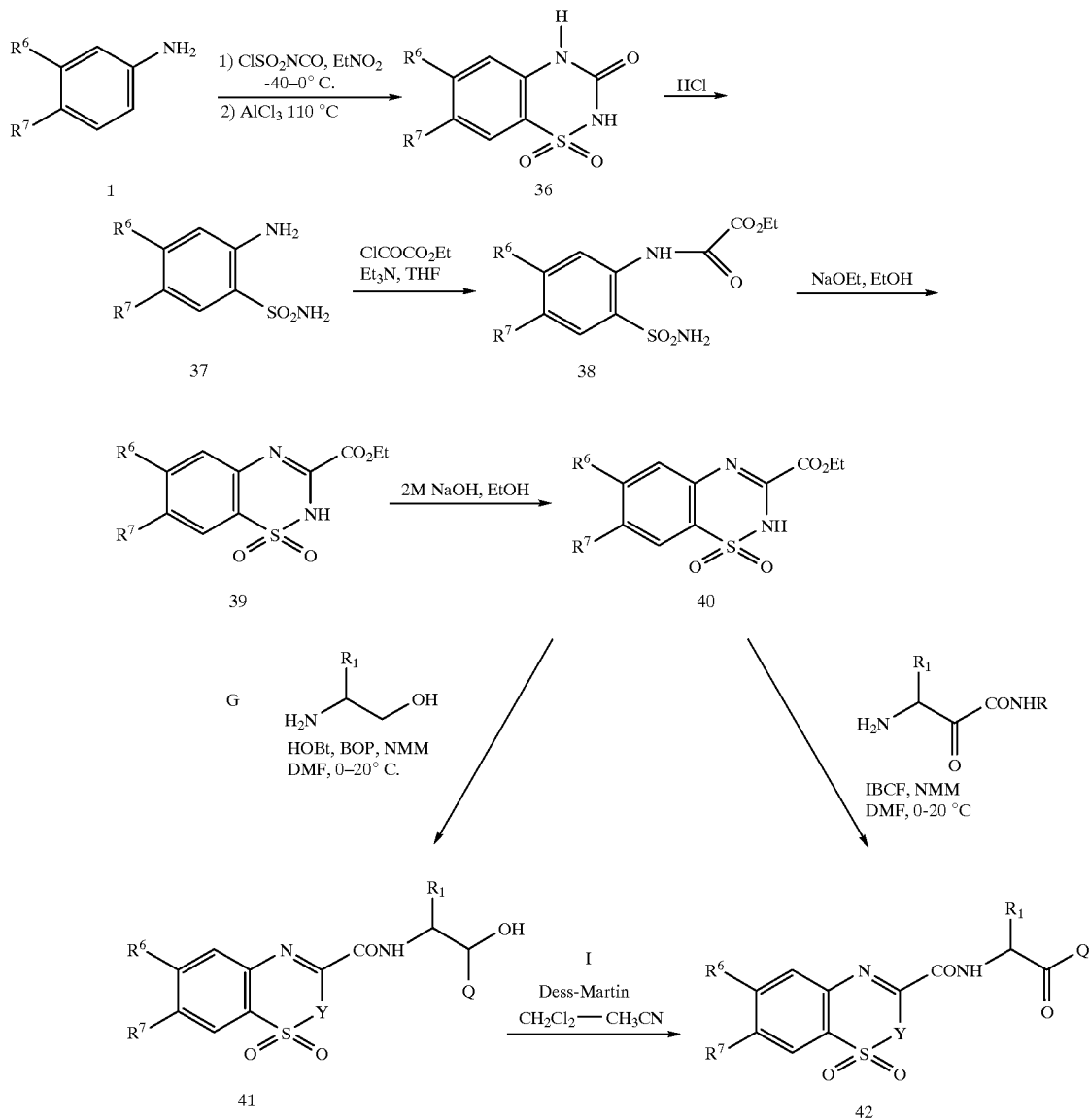

23  24
Scheme 6
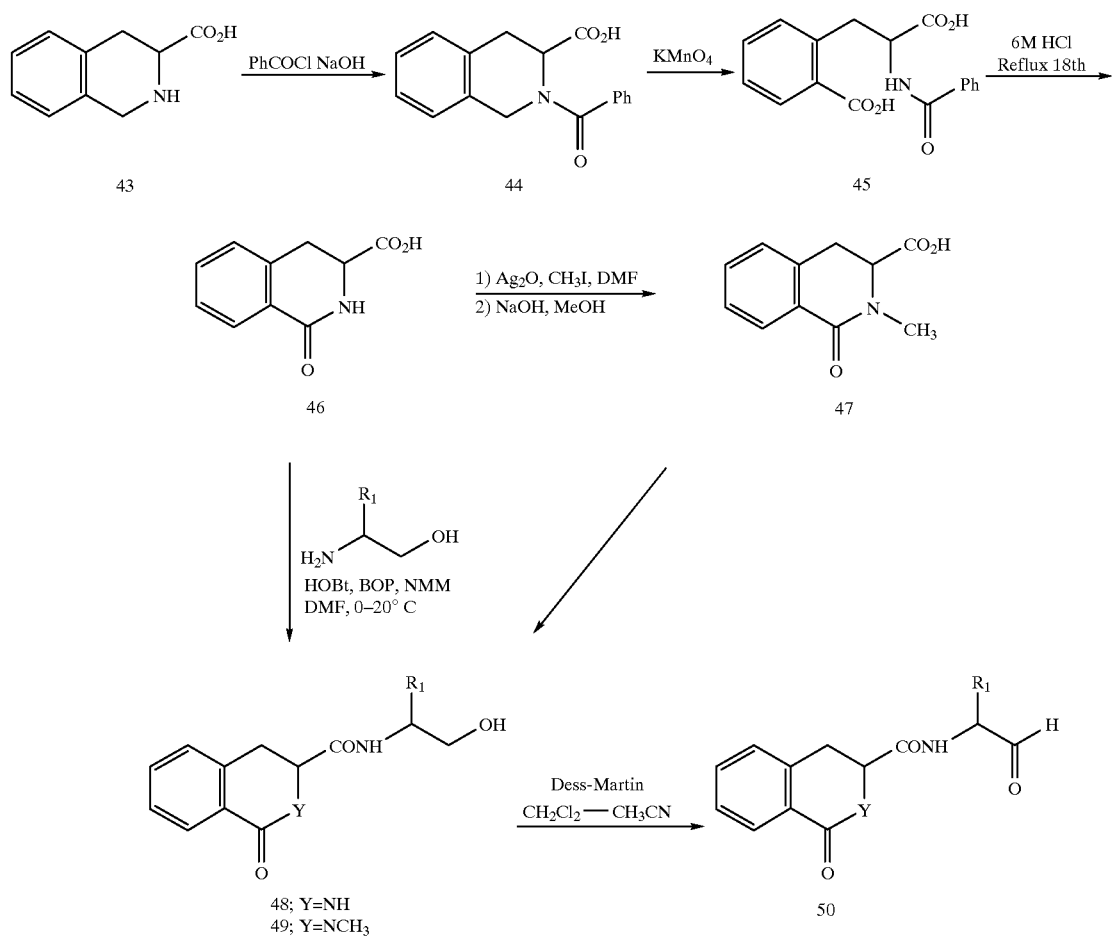
Scheme 7
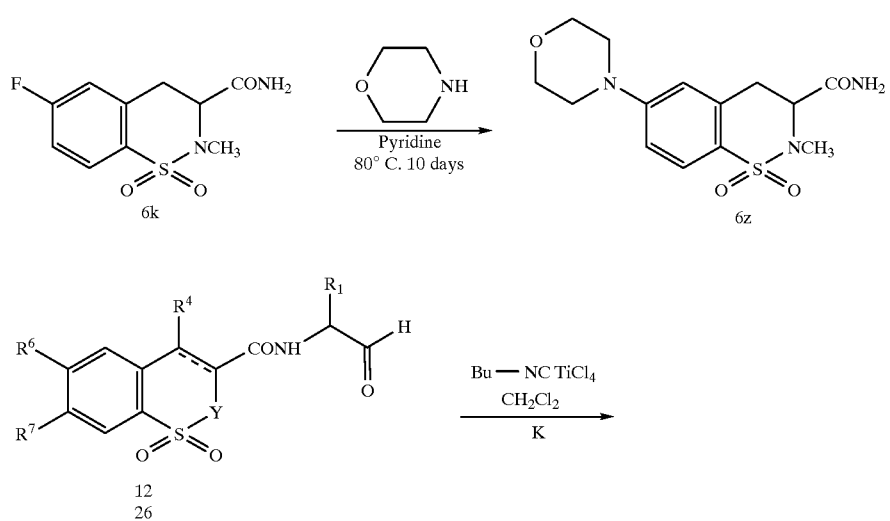

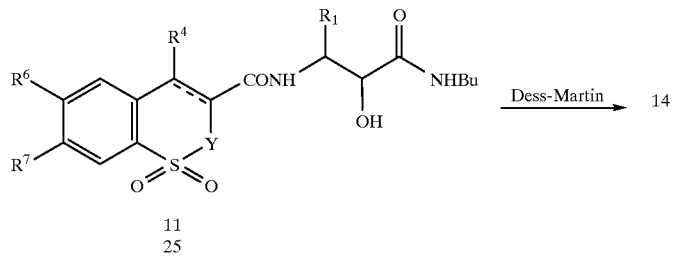

Example 1

General Procedure A: Condensation of Anilines with Acrylonitrile

Synthesis of Intermediate 2a ($R^6=R^7=OCH_3$)2-Chloro-3-(3,4-dimethoxyphenyl)propanenitrile The synthesis of intermediate 2a was performed according to the procedure of W. Pöpel et al., *Pharmazie*, 1980, 35, 266–278, which is herein incorporated by reference.

To a vigorously stirred solution of 4-aminoveratrole (17.8 g, 116 mmol) in water (150 ml) and 12N HCl (29 ml, 349 mmol) chilled in an ice-water bath was added dropwise a solution of sodium nitrite (9.2 g, 133 mmol) in water (15 ml) over 10–15 minutes. The mixture was stirred for an additional 15 minutes at the same temperature. This solution was added dropwise over 20 minutes to a vigorously stirred solution of acrylonitrile (18.6 g, 23 ml, 349 mmol), $CuCl_2 \cdot 2H_2O$ (3 g, 17.4 mmol), KCl (10 g, 134 mmol) and NaoAc (13.1 g, 160 mmol) in water (150 ml) and acetone (350 ml) chilled in an ice-water bath. The resulting mixture was allowed to stir while slowly warming to ambient temperature over 24–48 hours or until evolution of nitrogen gas had ceased. The acetone was removed on a rotary evaporator and the residue was extracted with ethyl acetate (2×250 ml). The combined organic phase was washed with water and brine, dried over anhydrous magnesium sulfate, filtered and concentrated. The dark residue was purified by flash chromatography (silica gel, dichloromethane) to give 6.0 g (23%) of the title compound as a pale yellow mobile oil. NMR ($CDCl_3$) δ 3.25 (2H, d, J=7 Hz), 3.88 (3H, s), 3.89 (3H, s), 4.53 (1H, t, J=7 Hz), 6.79 (1H, s), 6.85 (2H, s); Anal. Calc'd for $C_{11}H_{12}ClNO_2$: C, 58.54; H, 5.37; N, 6.21; Cl, 15.71; Found: C, 58.67; H, 5.42; N, 6.52; Cl, 15.98.

Example 2

Synthesis of Intermediate 2k ($R^6=F$; $R^7=H$)

2-Chloro-3-(3-fluorophenyl)propanenitrile

This compound was prepared according to General Procedure A. From 3-fluoroaniline (25 g, 0.23 mol) crude title compound (42 g) was obtained which was purified by flash chromatography on silica gel (10% $CH_2Cl_2$:hexanes) followed by further purification by distillation on a Kugelrohr apparatus (oven T=125° C., 0.3 mm Hg) to give 22 g (53%); NMR ($CDCl_3$) δ 3.30 (m, 2H), 4.56 (t, J=7 Hz, 1H), 7.04 (m, 3H), 7.35 (m, 1H).

Example 3

Synthesis of Intermediate 2 l ($R^6=R^7=Cl$)

2-Chloro-3-(3,4-dichlorophenyl)propanenitrile

This compound was prepared according to General Procedure A. From 3,4-dichloroaniline (35 g, 0.22 mol) crude title compound (41 g) was obtained which was purified by triple distillation on a Kugelrohr apparatus (oven T=160° C., 0.5 mm Hg) followed by treatment with decolorizing carbon in refluxing methanol to give 17.3 g (34%) of a yellow-orange mobile oil after filtration and concentration to constant weight; NMR ($CDCl_3$) δ 3.26 (m, 2H), 4.56 (t, J=7 Hz, 1H), 7.13 (m, 1H), 7.40 (m, 2H).

Example 4

Synthesis of Intermediate 2n ($R^6=Cl$; $R^7=H$)

2-Chloro-3-(3-chlorophenyl)propanenitrile

This compound was prepared according to General Procedure A. From 3-chloroaniline (25 g, 196 mmol) a crude product (19.6 g) was obtained which was further purified by distillation on a Kugelrohr apparatus (oven temp. 140° C., 0.2 mm Hg) to afford 17.1 g (44%) of the title compound as a yellow mobile oil; NMR ($CDCl_3$) δ 3.28 (2H, m), 4.57 (1H, t, J=7 Hz), 7.20 (1H, m), 7.28–7.33 (3H, m).

Example 5

Synthesis of Intermediate 2r ($R^6+R^7=OCH_2CH_2O$)

2-Chloro-3-(3,4-ethylenedioxyphenyl)propanenitrile

This compound was prepared according to General Procedure A. From 1,4-benzodioxan-6-amine (25 g, 165 mmol) the title compound (9.8 g, 26%) was obtained as a yellow solid; NMR ($CDCl_3$) δ 3.2 (2H, d, J=7 Hz), 4.25 (4H, s), 4.50 (1H, t, J=7 Hz), 6.73–6.86 (3H, m).

Example 6

Synthesis of Intermediate 2,3-Dihydrobenzothiazole 1,1-dioxide Derivatives 2,3-Dihydrobenzothiazole 1,1-dioxide derivatives (compounds of Formula I, where A—B=$CR^3$) can be prepared from 2,3-dihydrobenzothiazole-3-carboxylates according to the methods specified in Scheme I and General Procedures G–J. These intermediates can be formed by reduction of 3-hydroxy-2,3-dihydrobenzothiazole-3-carboxylates, described by J. Wrobel and A. Dietrich [*Heterocycles* 1994, 38, 1823–1838, incorporated by reference herein in its entirety] with reagents including sodium cyanoborohydride, sodium borohydride, zinc-acetic acid, or catalytic hydrogenation by methods known to those skilled in the art. Alternatively, 2,3-dihydrobenzothiazole-3-carboxylates may be prepared by treating N-alkylbenzenesulfonamides with a strong base such as butyllithium followed by glyoxylic ester by a modification of the method of Wrobel and Dietrich, supra.

Example 7

Synthesis of Intermediate 4,5-Dihydrobenzothiazepine 1,1-dioxide Derivatives 4,5-Dihydrobenzothiazepine 1,1-dioxide derivatives (compounds of Formula I, where A—B=$CHR^{4a}$-$CR^3$) can be prepared from 4,5-dihydrobenzothiazepine-3-carboxylates according to the methods specified in Scheme I and General Procedures G–J. These intermediates can be synthesized by modification of previously reported methods. For example, 3-(m-chlorophenyl)propionaldehyde (prepared according to the method of H. Hashizume et al., *Chem. Pharm. Bull.* 1994, 42, 512–520, incorporated by reference herein in its entirety), can be transformed into m-chlorohomophenylalanine by reaction with sodium cyanide and ammonium carbonate followed by hydrolysis. Treatment of m-chlorohomophenylalanine with chlorosulfonic acid by a modification of the procedure described by H. Zenno and T. Mizutani (Japanese patent application No. 7004990, 1966; Chem. Abstr. 72, 111525, incorporated by reference herein in its entirety) affords 7-chloro-4,5-dihydrobenzothiazepine-3-carboxylate. Alternatively, 2-(aminosulfonyl)phenyl-propanoic acid, described by P. Catsoulacos and C. Camoutsis (*J. Heterocycl. Chem.* 1976, 13, 1309–1314, incorporated by reference herein in its entirety), may be reduced to the corresponding aldehyde, treated with cyanide, hydrolyzed with acid or base, and cyclized by the procedure of Catsoulacos and Camoutsis to give 4,5-dihydrobenzothiazepine-3-carboxylate.

Example 8

Synthesis of Intermediate 3a ($R^6=R^7=OCH3$)3,4-Dihydro-6,7-dimethoxy-2,1-benzoxathiin-3-carboxylic acid To a flask containing 1.0 g (4.4 mmol) of compound 2a was added 1 ml of 98% $H_2SO_4$ with stirring. The viscous dark mixture was stirred overnight at ambient temperature, diluted with water (5 ml) and was held at reflux for four hours. The mixture was cooled to ambient temperature, water (25 ml) was added, and stirring was continued for an additional 15 minutes. The resulting precipitate was filtered and washed to neutrality with water before being allowed to air dry. The dark crude product was purified by recrystallization from 1,4-dioxane (activated carbon) to give 290 mg (22%) of the title compound as a tan powder, mp 273–275° C. (dec.); NMR (CDCl$_3$-DMSO-d$_6$) δ 3.16–3.29 (2H, m), 3.81 (6H, s), 5.34 (1H, dd, J=4 Hz, 12 Hz), 6.63 (1H, s), 7.11 (1H, s); MS: 311 m/z (M+Na)$^+$; Anal. Calc'd for $C_{11}H_{12}O_7S$: C, 45.83; H, 4.20; S, 11.10; Found: C, 45.26; H, 4.04; S, 11.98.

Example 9

General Procedure B: Aromatic Chlorosulfonylation
Synthesis of Intermediate 4c ($R^6=R^7=OCH_3$)
2-Chloro-3-(2-chlorosulfonyl-4,5-dimethoxyphenyl) propanamide To a solution of compound 2a (4.07 g, 18.0 mmol) in anhydrous chloroform (50 ml) chilled in an ice-water bath was added chlorosulfonic acid (4.2 g, 2.4 ml, 36.0 mmol) dropwise over 10–15 minutes. The mixture was stirred at this temperature for 5 hours and poured into a separatory funnel containing chloroform (50 ml) and water (50 ml). The organic phase was washed further with water and brine, dried (MgSO$_4$), filtered and concentrated. The brown sticky residue (2.8 g) was slurried with benzene (5 ml) for fifteen minutes, decanted and dried in-vacuo to constant weight to give 2.5 g (41%) of the title compound as a red-brown solid. The intermediate was used without further purification; MS: 342 m/z (M+H)$^+$, Cl$_2$ pattern.

Example 10
Synthesis of Intermediate 41 ($R^6=R^7=Cl$)
2-Chloro-3-(2-chlorosulfonyl-4,5-dichlorophenyl) propanamide This compound was prepared according to General Procedure B. From 2 1 (2.5 g, 10.7 mmol) in neat chlorosulfonic acid (~10 ml) at 150° C. for 1.5 hours, 3.3 g (89%) of the title compound was obtained as a yellow powder which was isolated by dropwise addition of the dark reaction mixture (cooled to ambient temperature) to a vigorously stirred slurry of ice-water (~100 g), suction filtration of the precipitate and washing with cold water and drying to constant weight in vacuo to give analytically pure material; Anal. Calc'd for $C_9H_7Cl_4NO_3S$: C, 30.80; H, 2.01; N, 3.99; S, 9.12; Found: C, 30.47; H, 1.92; N, 3.38; S, 9.29.

Example 11
Synthesis of Intermediate 4n ($R^6=Cl$; $R^7=H$)
2-Chloro-3-(2-chlorosulfonyl-5-chlorophenyl) propanamide This compound was prepared according to General Procedure B. To a dry flask equipped with a magnetic stirrer, rubber septum and drying tube was added compound 2n (5.0 g, 25.0 mmol). Chlorosulfonic acid (17 ml) was added with stirring over 5–10 minutes at ambient temperature. An appreciable exotherm was observed along with gas evolution (HCl) that persisted for 10–15 minutes following completion of the addition. After being allowed to stir for an additional one hour, the mixture was heated to 100° C. for one hour, cooled to ambient temperature, and added dropwise with vigorous stirring to an ice-water slurry (~500 g). The resulting precipitate was collected by suction filtration, washed with water several times, and dried in-vacuo to constant weight to afford 8.9 g of crude title compound as a pale yellow solid; NMR analysis suggested the presence of the desired product as well as an unidentified regioisomer: NMR (DMSO-d$_6$) δ 3.37 (1H, ABq), 3.60 (1H, ABq), (J=7 Hz, 14 Hz), 4.59 & 4.80 (1H, 2t, J=7 Hz), 7.18–7.26 (2H, m), 7.65–7.80 (1H, m). The product was used without further purification.

Example 12
Synthesis of Intermediate 4r ($R^6+R^7=OCH_2CH_2O$)
2-Chloro-3-(2-chlorosulfonyl-4,5-ethylenedioxyphenyl) propanamide This compound was prepared according to General Procedure B. From compound 2r (3.0 g, 13.4 mmol) the title compound (2.4 g, 51%) was obtained as a tan powder, which was used without further purification.

Example 13

General Procedure C: Reaction of Sulfonyl Chloride with Ammonia

Synthesis of Intermediate 5c ($R_6=R_7=OCH_3$)
3,4-Dihydro-6,7-dimethoxy-2H-1,2-benzothiazine-3-carboxamide 1,1-dioxide To a flask containing a solution of NH$_3$ in 1,4-dioxane (0.5M, 30 ml) was added compound 4c (1.0 g, 2.9 mmol). The mixture was held at reflux for 2 hours, cooled to room temperature and concentrated in-vacuo. The residue was slurried in water and the solid was collected by vacuum filtration, washed to neutrality with water and dried in-vacuo to constant weight to give 0.31 g (37%) of the title compound as an off-white powder; MS: 287 m/z (M+H)$^+$, 309 m/z (M+Na)$^+$.

Example 14
Synthesis of Intermediate 5r ($R^6+R^7=OCH_2CH_2O$)
3,4-Dihydro-6,7-ethylenedioxy-2H-1,2-benzothiazine-3-carboxamide 1,1-dioxide This compound was prepared according to General Procedure C. However, the reaction was performed using concentrated aqueous ammonium hydroxide. From compound 4r (2.4 g, 7.1 mmol) and conc. NH$_4$OH (50 ml) the title compound (0.87 g, 44%) was obtained following flash chromatography on silica gel (25% ethyl acetate/hexane to ethyl acetate); MS: 283 (M–H)$^-$.

Example 15

General Procedure D: Reaction of Sulfonyl Chlorides with Primary Amines
Synthesis of Intermediate 6e (R$^6$=R$^7$=OCH$_3$; Y=NCH$_3$)
3,4-Dihydro-6,7-dimethoxy-2-methyl-2H-1,2-benzothiazine-3-carboxamide 1,1-dioxide A mixture of compound 4c (1.1 g, 3.2 mmol) in 40% aqueous methylamine (10 ml) was stirred while being warmed to reflux. Small amounts of water (1–2 ml) were added after 30 and 45 minutes to facilitate stirring. After a total reflux period of 1.5 hours, the mixture was cooled in an ice-water bath and the solid was collected by suction filtration and washed to neutrality with water before being dried to constant weight in-vacuo. The title compound (0.57 g, 59%) was obtained as an off-white powder; mp 215–222° C.; NMR (DMSO-d$_6$) δ 2.58 (3H, s), 2.97–3.28 (2H, m), 4.51 (3H, s), 4,52 (3H, s), 4.53 (1H, dd, J=5 Hz, 12 Hz), 7.02 (1H, s), 7.12 (1H, s), 7.44 (1H, br; absent in D$_2$O), 7.64 (1H, br; absent in D$_2$O); MS: 301 m/z (M+H)$^+$, 323 m/z (M+Na)$^+$; Anal. Calc'd for C$_{12}$H$_{16}$N$_2$O$_7$S: C, 47.99; H, 5.38; N, 9.42; S, 10.66; Found: C, 48.22; H, 5.37; N, 9.25; S, 10.93.

Example 16

General Procedure E: Alkylation of Sulfonamides
Synthesis of Intermediate 6g (R$^6$=R$^7$=OCH$_3$; Y=NBn)
3,4-Dihydro-6,7-dimethoxy-2-benzyl-2H-1,2-benzothiazine-3-carboxamide 1,1-dioxide A mixture of compound 5c (250 mg, 0.87 mmol) and anhydrous potassium carbonate (300 mg, 2.2 mmol) in DMF (3 ml) was treated with benzyl bromide (0.11 ml, 0.96 mmol). The mixture was stirred while being warmed to 95–100° C. After five hours an additional 0.05 ml of benzyl bromide was added and the mixture was allowed to stir overnight at 95–100° C. The mixture was cooled to ambient temperature, the solvent was evaporated in-vacuo and the residue was partitioned between ethyl acetate and 5% aqueous citric acid solution. The organic phase was washed further with saturated aqueous sodium bicarbonate solution, brine, dried over anhydrous magnesium sulfate, filtered and concentrated to afford 310 mg (94%) of the title compound as a pale yellow solid which was used without further purification; MS: 377 m/z (M+H)$^+$, 399 m/z (M+Na)$^+$.

Example 17
Synthesis of Intermediate 6k (R$^6$=F; R$^7$=H; Y=NCH$_3$)
3,4-Dihydro-6-fluoro-2-methyl-2H-1,2-benzothiazine-3-carboxamide 1,1-dioxide This compound was prepared according to General Procedure D. From 4k (14.1 g, 52.6 mmol) the title compound (7.2 g, 53%) was obtained following flash chromatography on silica gel (30% to 80% ethyl acetate/hexanes); NMR (CDCl$_3$) δ 2.59 (s, 3H), 3.08–3.21 (m, 2H), 4.49–4.55 (m, 1H), 7.27–7.40 (m, 2H), 7.47 (br, 1H, CONH), 7.68 (br, 1H, CONH), 7.77–7.81 (m, 1H); MS: 259 m/z (M+H)$^+$; Anal. Calc'd for C$_{10}$H$_{11}$FN$_2$O$_3$S: C, 46.51; H, 4.30; N, 10.85; S, 12.39; F, 7.36; Found: C, 47.11; H, 4.49; N, 10.91; S, 12.02; F, 7.19.

Example 18
Synthesis of Intermediate 6 l (R$^6$=R$^7$=Cl; Y=NCH$_3$)
3,4-Dihydro-6,7-dichloro-2-methyl-2H-1,2-benzothiazine-3-carboxamide 1,1-dioxide This compound was prepared according to General Procedure D. From 4 (3.0 g, 8.5 mmol) the title compound (0.94 g, 36%) was obtained following flash chromatography on silica gel (25% ethyl acetate/hexanes); MS: 307, 309, 311 m/z (M+H)$^+$ (Cl$_2$ pattern).

Example 19
Synthesis of Intermediate 6p (R$^6$=Cl; R$^7$=H; Y=NCH$_3$)
3,4-Dihydro-5-chloro-2-methyl-2H-1,2-benzothiazine-3-carboxamide 1,1-dioxide This compound was prepared according to General Procedure D. From compound 4n (8.0 g, 25.3 mmol) the title compound (3.4 g, 49%) was obtained following flash chromatography on silica gel (25% ethyl acetate/hexane to ethyl acetate); NMR (DMSO-d$_6$) δ 2.60 (3H, s), 3.11–3.19 (2H, m), 4.48 (1H, dd, J=6 Hz), 7.47–7.74 (5H, m; 3Ar+2NH$_2$); MS: 275, 277 m/z, chloride isotope pattern.

Example 20
Synthesis of Intermediate 6r (R$^6$+R$^7$=OCH$_2$CH$_2$O; Y=NCH$_3$)
3,4-Dihydro-6,7-ethylenedioxy-2-methyl-2H-1,2-benzothiazine-3-carboxamide 1,1-dioxide This compound was prepared according to General Procedure D. From compound 4r (1.0 g, 2.9 mmol) the title compound (0.77 g, 88%) was obtained as an off-white solid; NMR (DMSO-d$_6$) δ 2.56 (3H, s), 2.95–3.04 (2H, m), 4.25 & 4.26 (4H, 2s), 4.40–4.46 (1H, ABq, J=6 Hz), 6.95 (1H, s), 7.12 (1H, s), 7.43 (1H, br; absent in D$_2$O), 7.63 (1H, br; absent in D$_2$O).

Example 21
Synthesis of Intermediate 6z (R$^6$=4-morpholino; R$^7$=H; Y=NCH$_3$)
3,4-Dihydro-6-(4-morpholino)-2-methyl-2H-1,2-benzothiazine-3-carboxamide 1,1-dioxide A solution of 6k (2.0 g, 7.75 mmol) in pyridine (30 ml) was treated with morpholine (6.75 g, 77.5 mmol) and warmed to 80–85° C. with stirring. After 10 days the mixture was concentrated in vacuo and the residue was partitioned between ethyl acetate and water. The organic phase was washed twice more with water and then brine, dried over anhydrous magnesium sulfate, filtered and concentrated to give 2.6 g of the crude product which was further purified by recrystallization (ethyl acetate/hexanes) to afford 1.7 g (71%) of the title compound as an off-white solid; NMR (DMSO-d$_6$) δ 2.70 (s, 3H), 3.18–3.33 (m, 6H), 3.82–3.85 (m, 4H), 4.12–4.18 (m, 1H), 6.75 (s, 1H), 6.84 (dd, J=2 Hz, 8 Hz, 1H), 7.65 (d, J=8 Hz, 1H); MS: 326 m/z (M+H)$^+$.

Example 22

General Procedure F: Amide Hydrolysis—Alkaline Conditions
Synthesis of Intermediate 7c (R$^6$=R$^7$=OCH$_3$)
3,4-Dihydro-6,7-dimethoxy-2H-1,2-benzothiazine-3-carboxylic acid 1,1-dioxide A slurry of compound 5c (300 mg, 1.05 mmol) in 6N NaOH (7 ml) was heated to reflux. After about 10 minutes the mixture became homogeneous. Reflux was continued for an additional 30–40 minutes at which time tlc analysis revealed complete consumption of starting material. The mixture was cooled to room temperature, a small amount of water was added to dissolve precipitated solids, and the pH was adjusted to ~3 with 6N HCl. The resulting precipitate was collected by suction filtration, washed to neutrality with water, and dried to constant weight in-vacuo to give 250 mg (84%) of the title compound as a white solid; NMR (DMSO-$d_6$) δ 2.97–3.18 (2H, m), 3.76 (6H, 2s), 4.33 (1H, m; dd in $D_2O$), 7.10 (1H, s), 7.57 (1H, s), 7.58 (1H, d, J=11 Hz; absent in $D_2O$); MS: 286 m/z (M–H)$^-$; Anal. Calc'd for $C_{11}H_{13}NO_6S$: C, 45.99; H, 4.57; N, 4.88; S, 11.14; Found: C, 46.16; H, 4.52; N, 4.86; S, 10.85.

Example 23
Synthesis of Intermediate 7r ($R^6+R^7$=OCH$_2$CH$_2$O)
3,4-Dihydro-6,7-ethylenedioxy-2H-1,2-benzothiazine-3-carboxylic acid 1,1-dioxide This compound was prepared according to General Procedure F (alkaline conditions). From compound 5r (250 mg, 0.88 mmol) the title compound (228 mg, 91%) was obtained as a tan solid; NMR (DMSO-$d_6$) δ 2.86–3.08 (2H, m), 4.25–4.33 (5H, m+s), 6.90 (1H, s), 7.08 (1H, s), 7.60 (1H, d, J=11 Hz; NH, absent in $D_2O$); MS: 284 (M–H)$^-$.

Example 24
Synthesis of Intermediate 8e ($R^6=R^7$=OCH$_3$; Y=NCH$_3$)
3,4-Dihydro-6,7-dimethoxy-2-methyl-2H-1,2-benzothiazine-3-carboxylic acid 1,1-dioxide This compound was prepared according to General Procedure F (alkaline conditions). From compound 6e (500 mg, 1.7 mmol) the title compound (480 mg, 96%) was obtained as a buff white solid; mp 196–200° C.; MS: 300 m/z (M–H)$^-$.

Example 25
Synthesis of Intermediate 8g ($R^6=R^7$=OCH$_3$; Y=NBn)
3,4-Dihydro-6,7-dimethoxy-2-benzyl-2H-1,2-benzothiazine-3-carboxylic acid 1,1-dioxide This compound was prepared according to General Procedure F (alkaline conditions). From compound 6g (290 mg, 0.77 mmol) the title compound (183 mg, 63%) was obtained as a white solid; NMR (DMSO-$d_6$) δ 3.13–3.27 (2H, m), 3.78 (6H, s), 4.19 (2H, ABq, J=16 Hz, 41 Hz), 4.54–4.59 (1H, dd, J=6 Hz), 7.04 (1H, s), 7.14 (1H, s), 7.18–7.33 (5H, m), 13.2 (1H, br; absent in $D_2O$); MS: 378 m/z (M+H)$^+$, 400 m/z (M+Na)$^+$.

Example 26
Synthesis of Intermediate 8i ($R^6$=H; $R^7$=H; Y=NCH$_3$)
3,4-Dihydro-2-methyl-2H-1,2-benzothiazine-3-carboxylic acid 1,1-dioxide A solution of 8p (550 mg, 2.0 mmol) in ethanol (25 ml) was shaken on a Paar apparatus with Raney nickel (~1 g, 50% aqueous, pH 9) under 50 psi hydrogen at room temperature for 18 hours. The mixture was filtered through a bed of Celite® filter aid and the filtrate was concentrated on a rotary evaporator. The residue was dissolved in water (10 ml), acidified to pH 3, and extracted with ethyl acetate. The organic phase was washed with brine, dried over magnesium sulfate, filtered and concentrated to give 378 mg (79%) of the title compound as a white solid; NMR (CDCl$_3$) δ 2.63 (s, 3H), 3.01–3.35 (m, 2H), 4.70–4.76 (m, 1H), 7.42–7.71 (m, 4H); MS: 240 m/z (M–H)$^-$; Anal. Calc'd for $C_{10}H_{11}NO_4S$: C, 49.79; H, 4.61; N, 5.81; S, 13.27; Found: C, 49.51; H, 4.62; N, 5.65; S, 13.05.

Example 27
Synthesis of Intermediate 8k ($R^6$=F; $R^7$=H; Y=NCH$_3$)
3,4-Dihydro-6-fluoro-2-methyl-2H-1,2-benzothiazine-3-carboxylic acid 1,1-dioxide This compound was prepared according to General Procedure F using acidic conditions (refluxing 4 N aqueous HCl in 1,4-dioxane) rather than basic conditions. From 6k (1.0 g, 3.87 mmol) the title compound (0.43 g, 43%) was obtained following recrystallization (ether/hexanes); MS: 258 m/z (M–H)$^-$; Anal. Calc'd for $C_{10}H_{10}FNO_4S$: C, 47.57; H, 4.55; N, 5.04; S, 11.52; F, 6.84; Found: C, 47.81; H, 4.28; N, 5.36; S, 11.62; F, 7.29.

Example 28
Synthesis of Intermediate 8l ($R^6=R^7$=Cl; Y=NCH$_3$)
3,4-Dihydro-6,7-dichloro-2-methyl-2H-1,2-benzothiazine-3-carboxylic acid 1,1-dioxide This compound was prepared according to General Procedure F (acidic conditions using refluxing 4N aqueous HCl in 1,4-dioxane). From 6l (200 mg, 0.65 mmol) the title compound (200 mg, 100%) was obtained following lyophillization of the reaction mixture; NMR (DMSO-$d_6$) δ 2.64 (s, 3H), 3.13–3.37 (m, 2H), 4.72–4.77 (m, 1H), 7.87 (s, 1H), 7.98 (s, 1H). MS: 308, 310, 312 m/z (M+H)$^+$ (Cl$_2$ pattern).

Example 29
Synthesis of Intermediate 8n ($R^6$=Cl; $R^7$=H; Y=N-i-Bu)
3,4-Dihydro-6-chloro-2-isobutyl-2H-1,2-benzothiazine-3-carboxylic acid 1,1-dioxide A solution of compound 9n (175 mg, 0.47 mmol) in 1,4-dioxane (7 ml) was treated with 4N HCl (10 ml) and refluxed for 1.5 hours. Upon cooling to ambient temperature a white precipitate formed. The 1,4-dioxane was removed on the rotary evaporator, the solid was collected by suction filtration, washed with water and air-dried to constant weight to give 148 mg (100%) of the title compound; MS: 316, 318 m/z (M–H)$^-$ (chloride isotope pattern).

Example 30
Synthesis of Intermediate 8p ($R^6$=Cl; $R^7$=H; Y=NCH$_3$)
3,4-Dihydro-6-chloro-2-methyl-2H-1,2-benzothiazine-3-carboxylic acid 1,1-dioxide A slurry of compound 6p (500 mg, 1.8 mmol) in 6N sulfuric acid (15 ml) was heated to reflux and stirred for 1.5 hours. The mixture was cooled to ambient temperature, extracted with ethyl acetate (50 ml) and the organic phase was washed twice with water, brine, dried over anhydrous magnesium sulfate, filtered and concentrated to afford 430 mg (86%) of the title compound; MS: 274, 276 m/z (M+H)$^+$, chlorine isotope pattern.

Example 31
Synthesis of Intermediate 8r ($R^6+R^7$=OCH$_2$CH$_2$O; Y=NCH$_3$)
3,4-Dihydro-6,7-ethylenedioxy-2-methyl-2H-1,2-benzothiazine-3-carboxylic acid 1,1-dioxide This compound was prepared according to General Procedure F (alkaline conditions). From compound 6r (600 mg, 2.0 mmol) the title compound (550 mg, 92%) was obtained as a pale yellow solid; NMR (DMSO-$_6$) δ 2.59 (3H, s), 3.01–3.24 (2H, m), 4.25, 4.26 (4H, 2s), 4.64–4.70 (1H, ABq, J=6 Hz), 6.95 (1H, s), 7.11 (1H, s), 13.40 (1H, br; absent in $D_2O$); MS: 298 m/z (M–H)$^-$.

Example 32
Synthesis of Intermediate 8s ($R^6+R^7$=OCH$_2$CH$_2$O; Y=NEt)
2-Ethyl-3,4-dihydro-6,7-ethylenedioxy-2H-1,2-benzothiazine-3-carboxylic acid 1,1-dioxide A mixture of compound 9s (200 mg, 0.59 mmol) in ethanol (1.5 ml) and 4N NaOH (3 ml) was stirred at room temperature for two hours. A small amount of solid separated from the initially homogeneous solution, and the mixture was warmed to ~50° C. to reestablish homogeneity. This process was repeated over the next four hours, where-upon the mixture was acidified to pH 2 (4N HCl), and the resulting oily precipitate was extracted into ethyl acetate. The organic phase was washed with water and brine, dried over anhydrous magnesium sulfate, filtered and concentrated to afford 153 mg (83%) of the title compound as a white solid which was used without further purification; NMR (CDCl$_3$) δ 0.99 (3H, t, J=7 Hz), 2.96–3.09 (4H, m), 4.25 (4H, br), 4.47 (1H, t, J=8 Hz), 6.97 (1H, s), 7.10 (1H, s); MS: 312 m/z (M−H)$^-$.

Example 33
Synthesis of Intermediate 8s ($R^6$+$R^7$=OCH$_2$CH$_2$O; Y=NEt)
2-Ethyl-3,4-Dihydro-6,7-ethylenedioxy-2H-1,2-benzothiazine-3-carboxylic acid 1,1-dioxide To a mixture of 272 mg (0.83 mmol) of compound 20 in 1.0 ml of MeOH and 3 ml of H$_2$O was added 1.25 ml (3.0 eq) of 2N NaOH at 0° C. with stirring. After 5 min, the ice bath was removed and the mixture was stirred at room temperature for 2 hours. The mixture was diluted with 5 ml of H$_2$O and the solvent was evaporated. The aqueous solution was extracted with ether, acidified to pH~3 with HCl, and extracted with CH$_2$Cl$_2$. The combined extracts were dried and evaporated to afford 250 mg (96%) of a white solid; NMR (CDCl$_3$) δ 1.09 (t, 3H, J=7.1 Hz), 3.01 (m, 1H) 3.26 (m, 3H), 4.14 (dd, 1H, J=7 Hz), 4.28 (s, 4H), 6.82 (s, 1H), 7.34 (s, 1H). MS: 314 m/z (M+H)$^+$. Condensation with L-phenylalaninol (General Procedure G) revealed that this sample of 8s consists of a 2:1 mixture of enantiomers. Anal. Calc'd for C$_{13}$H$_{15}$NO$_6$.S: Calc'd: C, 49.83; H, 4.73; N, 4.47; Found: C, 49.73; H, 4.69; N, 4.41.

Example 34
Synthesis of Intermediate 8u ($R^6$+$R^7$=OCH$_2$CH$_2$O; Y=N-i-Pr)
3,4-Dihydro-6,7-ethylenedioxy-2-isopropyl-2H-1,2-benzothiazine-3-carboxylic acid 1,1-dioxide A solution of 9u (165 mg, 0.45 mmol) in ethanol (3 ml) was treated with 6N NaOH, refluxed for five hours and allowed to cool to ambient temperature while being stirred overnight. The mixture was acidified to pH 3 with HCl and extracted with ethyl acetate. The organic phase was washed with water and brine, dried over anhydrous magnesium sulfate, filtered and concentrated to give 126 mg (86%) of the title compound as a white solid; NMR (CDCl$_3$) δ 0.58 (d, J=7 Hz, 3H), 1.17 (d, J=7 Hz, 3H), 3.29 (m, 2H), 4.05 (m, 1H), 4.30 (s+m, 5H), 6.84 (s, 1H), 7.35 (s, 1H); MS: 326 m/z (M−H)$^-$. Anal. Calc'd for C$_{14}$H$_{17}$NO$_6$S: C, 51.37; H, 5.25; N, 4.28; S, 9.78; Found: C, 50.92; H, 5.06; N, 4.18; S, 9.94.

Example 35
Synthesis of Intermediate 9l ($R^6$=$R^7$=Cl; Y=NCH$_3$; R CH$_3$)
Methyl 3,4-Dihydro-6,7-dichloro-2-methyl-2H-1,2-benzothiazine-3-carboxylate 1,1-dioxide To a solution of 8l (500 mg, 1.61 mmol) in THF (10 ml) and MeOH (5 ml) was added dropwise over five minutes a solution of (trimethylsilyl)diazomethane (2M in hexanes). After being stirred for one hour at ambient temperature the mixture was quenched with glacial acetic acid (0.5 ml) and extracted with ethyl acetate. The organic phase was washed with saturated sodium bicarbonate, water, brine, dried over anhydrous magnesium sulfate, filtered and concentrated to give the crude product which was recrystallized (ethyl acetate/hexanes) to afford 347 mg (66%) of the title compound as a tan solid; NMR CDCl$_3$) δ 2.81 (s, 3H), 3.15–3.42 (m, 2H), 3.86 (s, 3H), 4.68–4.74 (m, 1H), 7.43 (s, 1H), 7.91 (s, 1H); Anal. Calc'd for C$_{11}$H$_{11}$Cl$_2$NO$_4$S: C, 40.76; H, 3.43; N, 4.32; S, 9.87; Found: C, 41.31; H, 3.47; N, 4.48; S, 9.76.

Example 36
Synthesis of Intermediate 9n ($R^6$=Cl; $R^7$=H; Y=N-i-Bu; R=i-Bu)
Isobutyl 3,4-Dihydro-6-chloro-2-isobutyl-2H-1,2-benzothiazine-3-carboxylate 1,1-dioxide A mixture of 7n (540 mg, 2.06 mmol), potassium carbonate (1.4 g, 10.3 mmol) and isobutyl bromide (0.71 g, 0.56 ml, 5.16 mmol) in DMF (10 ml) was stirred at 70° C. After 18 hours the solvent was evaporated in vacuo and the residue was partitioned between ethyl acetate and water. The organic phase was washed with water and brine, dried over anhydrous magnesium sulfate, filtered and concentrated. The crude product was purified by flash chromatography on silica gel (30% ether/hexanes) to give 270 mg (35%) of the title compound as a white solid; NMR CDCl$_3$) δ 0.82 (d, J=7 Hz, 6H), 0.96 (s, J=7H, 6H), 2.71 (m, 2H), 2.90 (m, 2H), 3.16 (m, 2H), 3.48 (m, 2H), 4.38 (m, 1H), 7.37 (m, 2H), 7.73 (t, J=8 Hz, 1H); MS: 373, 375 m/z (M+H)$^+$ (chloride isotope pattern).

Example 37
Synthesis of Intermediate 9s ($R^6$+$R^7$=OCH$_2$CH$_2$O; R=Et; Y=NEt)
Ethyl 2-Ethyl-3,4-dihydro-6,7-ethylenedioxy-2H-1,2-benzothiazine-3-carboxylate 1,1-dioxide A stirred mixture of compound 7r (220 mg, 0.42 mmol) and anhydrous potassium carbonate (293 mg, 2.12 mmol) in DMF was treated with ethyl iodide (0.07 ml, 0.87 mmol) and warmed to 65° C. After three hours an additional aliquot of ethyl iodide (0.07 ml) was added and stirring was continued for a further three hours. The mixture was filtered, the DMF was stripped in-vacuo, and the residue was partitioned between ethyl acetate and water. The organic phase was washed with saturated aqueous sodium bicarbonate and brine, dried over anhydrous magnesium sulfate, filtered and concentrated. The residue was further purified by flash chromatography on silica gel (dichloromethane) to afford 200 mg (76%) of the title compound; NMR (CDCl$_3$) δ 1.16 (3H, t, J=7 Hz), 1.32 (3H, t, J=7 Hz), 3.08–3.29 (4H, m), 4.24–4.31 (6H, m), 4.45 (1H, dd, J=6 Hz), 6.76 (1H, s), 7.32 (1H, s); MS: 342 m/z (M+H)$^+$, 364 m/z (M+Na)$^+$.

Example 38
Synthesis of Intermediate 9u ($R^6$+$R^7$=OCH$_2$CH$_2$O; Y=N-i-Pr; R=i-Pr)
Isopropyl 3,4-Dihydro-6,7-ethylenedioxy-2-isopropyl-2H-1,2-benzothiazine-3-carboxylate 1,1-dioxide This compound was prepared using the procedure described for 9n. From 7r (200 mg, 0.70 mmol) the title compound (167 mg, 65%) was obtained as a white solid following preparative tlc on silica gel (CH$_2$Cl$_2$); NMR (CDCl$_3$) δ 0.66 (d, J=7 Hz, 3H), 1.15 (d, J=7 Hz, 3H), 1.28 (d, J=6 Hz, 6H), 3.11–3.39 (m, 2H), 3.93–3.99 (m, 1H), 4.18–4.27 (s+m, 5H), 5.07–5.11 (m, 1H), 6.77 (s, 1H), 7.30 (s, 1H); MS: 370 m/z (M+H)$^+$.

Example 39

General Procedure G: Amide Formation
Synthesis of Intermediate 10a ($R^6$=$R^7$=OCH$_3$; $R^1$=i-Bu; Y=O) N-(3,4-Dihydro-6,7-dimethoxy-2,1-benzoxathiin-3-carbonyl)-L-leucinal 1,1-dioxide diethyl acetal A solution of compound 3a (180 mg, 0.63 mmol), HOBt (93 mg, 0.69 mmol) and N-methylmorpholine (NMM) (202 mg, 2.0 mmol) in DMF (2 ml) was cooled in an ice-water bath and treated with BOP (304 mg, 0.69 mmol). After being stirred an additional 15 minutes the mixture was treated with a solution of (L)-leucinal diethyl acetal (130 mg, 0.69 mmol) in DMF (1 ml). The resulting mixture was allowed to stir overnight while slowly warming to ambient temperature. The DMF was removed under reduced pressure and the residue was partitioned between ethyl acetate and 5% aqueous citric acid. The organic phase was washed with saturated aqueous sodium bicarbonate, water and brine, dried over anhydrous magnesium sulfate, filtered and concentrated. The residue was further purified by flash chromatography on silica gel (25–50% ethyl acetate/hexane) to afford 126 mg (44%) of the title compound as an amorphous solid; MS: 482 m/z (M+Na)$^+$; Anal. Calc'd for $C_{21}H_{33}NO_8S$: C, 54.88; H, 7.25; N, 3.05; Found: C, 55.05; H, 7.25; N, 3.26.

Example 40
Synthesis of Intermediate 10v ($R^6+R^7=OCH_2CH_2O$; $R^1$=i-Bu; Y=NEt)

N-(3,4-Dihydro-6,7-ethylenedioxy-2-ethyl-2H-1,2-benzothiazine-3-carbonyl)-L-leucinal 1,1-dioxide diethyl acetal This compound was prepared according to General Procedure G. From 8v (350 mg, 1.12 mmol) and (L)-leucinal diethyl acetal (275 mg, 1.45 mmol) crude title compound (574 mg) was obtained. Separation of diastereomers was achieved by flash chromatography on silica gel (50% ethyl acetate/hexanes):

Isomer 1: 162 mg (30%); MS: 507 m/z (M+Na)$^+$;
Isomer 2: 160 mg (29%); MS: 507 m/z (M+Na)$^+$.

Example 41
Synthesis of Intermediate 11b ($R^6=R^7=OCH_3$; $R^1$=Bn; Y=O; Q=H)

N-(3,4-Dihydro-6,7-dimethoxy-2,1-benzoxathiin-3-carbonyl)-L-phenylalaninol 1,1-dioxide This compound was prepared according to General Procedure G. From compound 3a (61 mg, 0.21 mmol) and L-phenylalaninol (42 mg, 0.28 mmol) the title compound (64 mg, 72%) was obtained as a mixture of diastereomers; MS: 422 m/z (M+H)$^+$, 444 m/z (M+H)$^+$.

Example 42
Synthesis of Intermediate 11c ($R^6=R^7=OCH_3$; $R^1$=Bn; Y=NH; Q=H)

N-(3,4-Dihydro-6,7-dimethoxy-2H-1,2-benzothiazine-3-carbonyl)-L-phenylalaninol 1,1-dioxide This compound was prepared according to General Procedure G. From compound 7c (100 mg, 0.35 mmol) the crude title compound (176 mg) was obtained as a mixture of diastereomers which were separated by flash chromatography on silica gel (EtOAc:hexane, 1:1 to 3:1).

Isomer 1: 40 mg (27%); MS: 421 m/z (M+H)$^+$;
Isomer 2: 54 mg (37%); MS: 421 m/z (M+H)$^+$.

Intermediate fractions gave a small amount of the product as a mixture of diasteromers. Anal. Calc'd for $C_{20}H_{24}N_2O_6S \cdot 0.5H_2O$: C, 55.93; H, 5.88; N, 6.52; S, 7.45; Found: C, 55.55; H, 5.83; N, 6.32; S, 7.76.

Example 43
Synthesis of Intermediate 11e ($R^6=R^7=OCH_3$; $R^1$=Bn; Y=NCH$_3$; Q=H)

N-(3,4-Dihydro-6,7-dimethoxy-2-methyl-2H-1,2-benzothiazine-3-carbonyl)-L-phenylalaninol 1,1-dioxide This compound was prepared according to General Procedure G. From compound 8e (250 mg, 0.83 mmol) the crude title compound (343 mg) was obtained as a mixture of diastereomers which were separated by flash chromatography on silica gel (EtOAc:hexane, 1:3 to 1:1).

Isomer 1: 123 mg (34%); MS: 435 m/z (M+H)$^+$;
Isomer 2: 118 mg (33%); MS: 435 m/z (M+H)$^+$.

Example 44
Synthesis of Intermediate 11g ($R^6=R^7=OCH_3$; $R^1$=Bn; Y=NBn; Q=H)

N-(2-Benzyl-3,4-dihydro-6,7-dimethoxy-2H-1,2-benzothiazine-3-carbonyl)-L-phenylalaninol 1,1-dioxide This compound was prepared according to General Procedure G. From compound 8g (155 mg, 0.41 mmol) the crude title compound (220 mg) was obtained as a mixture of diastereomers, partial separation being achieved by flash chromatography on silica gel (ether to 10% ethyl acetate/ether):

Isomer 1: 27 mg (13%); MS: 511 m/z (M+H)$^+$, 533 m/z (M+Na)$^+$;
Isomer 2: 30 mg (14%); MS: 511 m/z (M+H)$^+$, 533 m/z (M+Na)$^+$;

Intermediate fractions gave an additional 105 mg (50%) of the diastereomeric mixture.

Example 45
Synthesis of Intermediate 11i ($R^6$=H; $R^7$=H; $R^1$=Bn; Y=NCH$_3$; Q=H)

N-(3,4-Dihydro-2-methyl-2H-1,2-enzothiazine-3-carbonyl)-L-phenylalaninol 1,1-dioxide This compound was prepared according to General Procedure G. From 8i (200 mg, 0.83) the crude title compound was obtained as a mixture of diastereomers which were separated by preparative thin layer chromatography on silica gel using ethyl acetate as eluent:

Isomer 1 ($R_f$ 0.6): 120 mg (39%); MS: 37S m/z (M+H)$^+$;
Isomer 2 ($R_f$ 0.7): 81 mg (26%); MS: 375 m/z (M+H)$^+$.

Example 46
Synthesis of Intermediate 11k ($R^6$=F; $R^7$=H; $R^1$=Bn; Y=NCH$_3$; Q=H)

N-(3,4-Dihydro-2-methyl-6-fluoro-2H -1,2-benzothiazine-3-carbonyl)-L-phenylalaninol 1,1-dioxide This compound was prepared according to General Procedure G. From 8k (200 mg, 0.83) the crude title compound was obtained as a mixture of diastereomers. Attempted separation of these isomers by preparative tlc on silica gel (10% methanol/$CH_2Cl_2$) gave only one characterizable isomer of $R_f$ 0.7; 78 mg (26%); MS: 393 m/z (M+H)$^+$.

Example 47
Synthesis of Intermediate 11-l ($R^6=R^7$=Cl; $R^1$=Bn; Y=NCH$_3$; Q=H)

N-(3,4-Dihydro-6,7-dichloro-2-methy-2H-1,2-benzothiazine-3-carbonyl)-L-phenylalaninol 1,1-dioxide This compound was prepared according to General Procedure G. From 8 1 (200 mg, 0.65 mmol) the crude title compound was obtained as a mixture of diastereomers which were separated by flash chromatography on silica gel using ethyl acetate as eluent:

Isomer 1: 60 mg (21%); MS: 465, 467, 469 m/z (M+H)$^+$. (Cl$_2$ pattern);
Isomer 2: 100 mg (35%); MS: 465, 467, 469 m/z (M+H)$^+$ (Cl$_2$ pattern);

Example 48
Synthesis of Intermediate 11n ($R^6$=Cl; $R^7$=H; $R^1$=Bn; Y=N-i-Bu; Q=H)

N-(3,4-Dihydro-6-chloro-2-isobutyl-2H-1,2-benzothiazine-3-carbonyl)-L-phenylalaninol 1,1-dioxide This compound was prepared according to General Procedure G. From 8n (146 mg, 0.46 mmol) the crude title compound was obtained as a mixture of diastereomers which were separated by preparative tlc on silica gel using 50% ethyl acetate/hexanes as eluent:

Isomer 1 ($R_f$ = 0.5): 76 mg (37%); MS: 450, 452 m/z (M+H)$^+$ (Cl$_2$ pattern);

Isomer 2 ($R_f$ =0.6): 81 mg (39%); MS: 450, 452 m/z (M+H)$^+$ ($Cl_2$ pattern).

Example 49

Synthesis of Intermediate 11p ($R^6$=Cl; $R^7$=H; $R^1$=Bn; Y=NCH$_3$; Q=H)

N-(6-Chloro-3,4-dihydro-2-methyl-2H-1,2-benzothiazine-3-carbonyl)-L-phenylalaninol 1,1-dioxide This compound was prepared according to General Procedure G. From compound 8p (420 mg, 1.52 mmol) crude product (690 mg) was obtained as a mixture of diastereomers. Separation was achieved by flash chromatography on silica gel (30% ethyl acetate/hexane to 50% ethyl acetate/hexane) to give two isomers of the title compound:

Isomer 1: 78 mg (13%); MS: 409, 411 m/z (M+H)$^+$, 431, 433 m/z (M+Na)$^+$;

Isomer 2: 71 mg (11%); MS: 409, 411 m/z (M+H)$^+$, 431, 433 m/z (M+Na)$^+$.

Example 50

Synthesis of Intermediate 11r ($R^6$ +$R^7$=OCH$_2$CH$_2$O; R$_1$=Bn; Y=NCH$_3$; Q=H)

N-(3,4-Dihydro-6,7-ethylenedioxy-2-methyl-2H-1,2-benzothiazine-3-carbonyl)-L-pheniylalaninol 1,1-dioxide This compound was prepared according to General Procedure G. From compound 8r (404 mg, 1.35 mmol) the title compound (475 mg, 81%) was obtained as a mixture of diastereomers following purification on silica gel (30% ethyl acetate/hexane). This product was used in the subsequent step without further purification; MS: 433 m/z (M+H)$^+$, 455 m/z (M+Na)$^+$.

Example 51

Synthesis of Intermediate 11s ($R^6$+$R^7$=OCH$_2$CH$_2$O; R$_1$=Bn; Y=NEt; Q=H)

N-(3,4-Dihydro-6,7-ethylenedioxy-2-ethyl-2H-1,2-benzothiazine-3-carbonyl)-L-phenylalaninol 1,1-dioxide This compound was prepared according to General Procedure G. From compound 8s (134 mg, 0.43 mmol) crude product (203 mg) was obtained as a mixture of diastereomers. Separation was achieved by flash chromatography on silica gel (50% ethyl acetate/hexane) to give two isomers of the title compound:

Isomer 1: 75 mg (39%); MS: 447 m/z (M+H)$^+$, 469 m/z (M+Na)$^+$;

Isomer 2: 82 mg (43%); MS: 447 m/z (M+H)$^+$, 469 m/z (M+Na)$^+$.

Example 52

Synthesis of Intermediate 11u ($R^6$+$R^7$=OCH$_2$CH$_2$O; $R^1$=Bn; Y=N-i-Pr; Q=H)

N-(3,4-Dihydro-6,7-ethylenedioxy-2-isopropyl-2H-1,2-benzothiazine-3-carbonyl)-L-phenylalaninol 1,1-dioxide This compound was prepared according to General Procedure G. From 8u (120 mg, 0.37) crude title compound (183 mg) was obtained. Attempted separation of diastereomers on silica gel (either flash chromatography or preparative tlc using 3% MeOH/CH$_2$Cl$_2$) was unsuccessful, giving 85 mg of the diastereomeric mixture; MS: 461 m/z (M+H)$^+$.

Example 53

Synthesis of Intermediate 11x ($R^6$+$R^7$=OCH$_2$CH$_2$O; $R^1$= (CH$_2$)$_4$NHSO$_2$Ph; Y=NEt; Q=H)

N-(3,4-Dihydro-6,7-ethylenedioxy-2-methyl-2H-1,2-benzothiazine-3-carbonyl)-L-N$_\epsilon$-(benzenesulfonyl)lysinol 1,1-dioxide This compound was prepared according to General Procedure G. From 8s (70 mg, 0.23 mmol) and L-N$_\epsilon$-(benzenesulfonyl)lysinol trifluoroacetic acid salt (117 mg, 0.30 mmol) crude product (144 mg) was obtained as a mixture of diastereomers. Separation was effected by preparative tlc on silica gel (5% MesH/CH$_2$Cl$_2$):

Isomer 1: 31 mg (25%); MS: 554 m/z (M+H)$^+$;

Isomer 2: 31 mg (25%); MS: 554 m/z (M+H)$^+$.

Example 54

Synthesis of Intermediate 11z ($R^6$+$R^7$=OCH$_2$CH$_2$O; $R^1$=Bn; Y=NCH$_3$; Q=H)

N-(3,4-Dihydro-6-(4-morpholino)-2-methyl-2H-1,2-benzothiazine-3-carbonyl)-L-phenylalaninol-1,1-dioxide This compound was prepared according to General Procedure G. From 8z (200 mg, 0.61 mmol) crude product (357 mg) was obtained as a mixture of diastereomers which were separated by flash chromatography on silica gel (75% ethyl acetate/hexanes):

Isomer 1: 116 mg (41%); MS: 460 m/z (M+H)$^+$;

Isomer 2: 113 mg (40%); MS: 460 m/z (M+H)$^+$.

Example 55

Synthesis of Intermediate 11A ($R^6$=Cl; $R^7$=H; $R^1$=Bn; Y=NCH$_3$; Q=CONHEt)

N-Ethyl-3-(6-chloro-3,4-dihydro-2-methyl-2H-1,2-benzothiazine- 3-carboxamido)-2-(R,S)-hydroxy-3-(S)-benzylpropanamide 1,1-dioxide This compound was prepared according to General Procedure G. From compound 8p (110 mg, 0.40 mmol) and N-ethyl-2-(R,S)-hydroxy-3-(S)-benzyl-3-aminopropanamide, trifluoroacetic acid salt (167 mg, 0.50 mmol) (Harbeson, S. L., et al.; *J. Med. Chem.*, 1994, 37, 2918–2929, incorporated by reference herein in its entirety) the title compound (60 mg, 31%) was obtained following purification by preparative tlc on silica gel (CH$_2$Cl$_2$:CH$_3$OH:conc. NH$_4$OH; 90:9:1; $R_f$ 0.5); MS: 480 m/z (M+H)$^+$; 502 m/z (M+Na)$^+$.

Example 56

General Procedure K: Reaction of Aldehydes with Butyl Isocyanide

Synthesis of Intermediate 11B ($R^6$+$R^7$=OCH$_2$CH$_2$O; $R^1$=i-Bu; Y=NEt; Q=CONHBu)

3-((3,4-Dihydro-6,7-ethylenedioxy-2-ethyl-2H-1,2-benzothiazine-3-carbonyl)amino)-3-(S)-isobutyl-2-(R,S)-hydroxy-N-butylpropanamide 1,1-dioxide A solution of butyl isocyanide (22 mg, 0.27 mmol) in dichloromethane (3 ml) was cooled in an ice-water bath and treated with TiCl$_4$ (0.28 ml, 1M in CH$_2$Cl$_2$). The mixture was stirred for three hours, cooled to −78° C. and treated with a solution of 12v (114 mg, 0.26 mmol) in CH$_2$Cl$_2$ (2 ml). The mixture was allowed to slowly warm to ambient temperature while being stirred overnight. The mixture was stirred with 1N HCl (5 ml) for 30 minutes, ethyl acetate (35 ml) was added and 1N NaOH was added to pH 9. The organic phase was washed with water and brine, dried over anhydrous sodium sulfate, filtered and concentrated to give 125 mg crude product which was triturated with ether to give 38 mg of the title compound as a white solid; MS: 512 m/z (M+H)$^+$.

Example 57

Synthesis of Intermediate 11C ($R^6$+$R^7$=OCH$_2$CH$_2$O; $R^1$=i-Bu; Y=NEt; Q=CONHBu)

3-((3,4-Dihydro-6,7-ethylenedioxy-2-ethyl-2H-1,2-benzothiazine-3-carbonyl)amino)-3-(S)-isobutyl-2-(R,S)-hydroxy-N-butylpropanamide 1,1-dioxide

Example 58
Synthesis of Intermediate 11E ($R^6+R^7=OCH_2CH_2O$; $R^1$=Bn; Y=NEt; Q=CONHBu)

3-((3,4-Dihydro-6,7-ethylenedioxy-2-ethyl-2H-1,2-benzothiazine-3-carbonyl)amino)-3-(S)-benzyl-2-(R,S)-hydroxy-N-butylpropanamide 1,1-dioxide This compound was prepared according to General Procedure K. From 12s (250 mg, 0.56 mmol) the title compound (200 mg, 65% yield) was obtained as a white solid; MS: 512 m/z (M+H)$^+$; MS: 546 m/z (M+H)$^+$; Anal. Calc'd for $C_{27}H_{35}N_3O_7S.0.5H_2O$: C, 58.46; H, 6.56; S, 5.77; Found: C, 58.73; H, 6.42; S, 5.83.

Example 59
Synthesis of Intermediate 11F ($R^6+R^7=OCH_2CH_2O$; $R^1$=Bn; Y=NEt; Q=CONHBu)

3-((3,4-Dihydro-6,7-ethylenedioxy-2-ethyl-2H-1,2-benzothiazine-3-carbonyl)amino)-3-(S)-benzyl-2-(R,S)-hydroxy-N-butylpropanamide 1,1-dioxide This compound was prepared according to General Procedure K. From 12t (250 mg, 0.56 mmol) crude title compound (200 mg) was obtained as a yellow oil which could not be made to crystallize from ether. Purification was effected by flash chromatography on silica gel (50% ethyl acetate/hexanes) to give 68 mg (22%) of the pure product; MS: 546 m/z (M+H)$^+$.

Example 60
Synthesis of Intermediate 11S ($R^6+R^7=OCH_2CH_2O$; $R^1$=Bn; Y=NEt; Q=CONHCH$_2$CH$_2$NHSO$_2$CH$_3$)

N-(2-(Methanesulfonylamino)ethyl)-3-(3,4-Dihydro-6,7-ethylenedioxy-2H-1,2-benzothiazine-3-carboxamido)-2-(R,S)-hydroxy-3-(S)-benzylpropanamide 1,1-dioxide This compound was prepared according to General Procedure G. From compound 8s (31.0 mg, 0.1 mmol, prepared from L-DOPA) and N-(2-(methanesulfonylamino)ethyl)-2-(R,S)-hydroxy-3-(S)-benzyl-3-aminopropanamide, HCl salt (42 mg, 1.20 eq) the title compound (45.0 mg, 74%) was obtained; MS: 611 (M+H)$^+$.

N-(2-(methanesulfonylamino)ethyl)-2-(R,S)-hydroxy-3-(S)-benzyl-3-aminopropanamide, HCl salt was prepared by coupling of N-(methanesulfonyl)aminoethyleneamine to N-3-(t-butoxycarbonyl)amino-2-(R,S)-hydroxy-3-(S)-benzylpropionic acid according to Harbeson's procedure (*J. Med. Chem.*, 1994, 37, 2918–2929). N-(methanesulfonyl) aminoethanamine was prepared from (N-(t-butoxycarbonyl) amino)ethanamine and methanesulfonyl chloride according to the procudure of Essien, H. et al., *J. Med. Chem.*, 1988, 31, 898–901, incorporated by reference herein in its entirety.

Example 61
Synthesis of Intermediate 11T ($R^6+R^7=OCH_2CH_2O$; $R^1$=Bn; Y=NEt; Q=CONHCH$_2$CH$_2$NHSO$_2$(4-NO$_2$-Ph))

3-((3,4-Dihydro-6,7-ethylenedioxy-2-ethyl-2H-1,2-benzothiazine-3-carbonyl)amino)-3-(S)-benzyl-2-(R,S)-hydroxy-N-(2-(4-nitrobenzenesulfonylamino)ethyl) propanamide 1,1-dioxide This compound was prepared according to General Procedure G. From 8s (prepared from L-DOPA, 30 mg, 0.10 mmol) and 3-amino-3-(S)-benzyl-2-(R,S)-hydroxy-N-(2-(4-nitrobenzenesulfonylamino)ethyl)propanamide hydrochloride (57 mg, 0.12 mmol) the title compound (52 mg, 91%) was obtained following flash chromatography on silica gel (75% ethyl acetate/hexanes); MS: 718 m/z (M+H)$^+$.

Example 62
Synthesis of Intermediate 11U ($R^6+R^7=OCH_2CH_2O$; $R^1$=Bn; Y=NEt; Q=CONH(CH$_2$)$_3$NHSO$_2$(4-NO$_2$-Ph))

3-((3,4-Dihydro-6,7-ethylenedioxy-2-ethyl-2H-1,2-benzothiazine-3-carbonyl)amino)-3-(S)-benzyl-2-(R,S)-hydroxy-N-(3-(4-nitrobenzenesulfonylamino)propyl) propanamide 1,1-dioxide This compound was prepared according to General Procedure G. From 8s (prepared from L-DOPA, 30 mg, 0.10 mmol) and 3-amino-3-(S)-benzyl-2-(R,S)-hydroxy-N-(3-(4-nitrobenzenesulfonylamino)propyl)propanamide hydrochloride (59 mg, 0.12 mmol) the title compound (32 mg, 55%) was obtained following flash chromatography on silica gel (75% ethyl acetate/hexanes); MS: 732 m/z (M+H)$^+$.

Example 63
Synthesis of Intermediate 11V ($R^6+R^7=OCH_2CH_2O$; $R^1$=Bn; Y=NEt; Q=CONHCH$_2$CH$_2$NHSO$_2$(3,4-Cl$_2$-Ph))

3-((3,4-Dihydro-6,7-ethylenedioxy-2-ethyl-2H-1,2-benzothiazine-3-carbonyl)amino)-3-(S)-benzyl-2-(R,S)-hydroxy-N-(2-(3,4-dichlorobenzenesulfonylamino)ethyl) propan-amide 1,1-dioxide This compound was prepared according to General Procedure G. From 8s (prepared from L-DOPA, 30 mg, 0.10 mmol) and 3-amino-3-(S)-benzyl-2-(R,S)-hydroxy-N-(2-(3,4-dichlorobenzenesulfonylamino)ethyl)propanamide hydrochloride (60 mg, 0.12 mmol) the title compound (58 mg, 97%) was obtained following flash chromatography on silica gel (75% ethyl acetate/hexanes); MS: 741, 743, 745 m/z (M+H)$^+$.

Example 64
Synthesis of Intermediate 11W ($R^6+R^7=OCH_2CH_2O$; $R^1$=Bn; Y=NEt; Q=CONH(CH$_2$)$_3$NHSO$_2$(3,4-Cl$_2$-Ph))

3-((3,4-Dihydro-6,7-ethylenedioxy-2-ethyl-2H-1,2-benzothiazine-3-carbonyl)amino)-3-(S)-benzyl-2-(R,S)-hydroxy-N-(3-(3,4-dichlorobenzenesulfonylamino)propyl) propanamide 1,1-dioxide This compound was prepared according to General Procedure G. From 8s (prepared from L-DOPA, 30 mg, 0.10 mmol) and 3-amino-3-(S)-benzyl-2-(R,S)-hydroxy-N-(3-(3,4-dichlorobenzenesulfonyl)propyl)propanamide hydrochloride (62 mg, 0.12 mmol) the title compound (58 mg, 97%) was obtained following flash chromatography on silica gel (75% ethyl acetate/hexanes); MS: 755, 757, 759 m/z (M+H)$^+$.

Example 65
Synthesis of Intermediate 11X ($R^6+R^7=OCH_2CH_2O$; $R^1$=Bn; Y=NEt; Q=CONHCH$_2$CH$_2$NHSO$_2$Ph)

3-((3,4-Dihydro-6,7-ethylenedioxy-2-ethyl-2H-1,2-benzothiazine-3-carbonyl)amino)-3-(S)-benzyl-2-(R,S)-hydroxy-N-(2-(benzenesulfonylamino)ethyl) propanamide 1,1-dioxide This compound was prepared according to General Procedure G. From 8s (prepared from L-DOPA, 35 mg, 0.11 mmol) and 3-amino-3-(S)-benzyl-2-(R,S)-hydroxy-N-(2-(benzenesulfonylamino)ethyl)propanamide hydrochloride (60 mg, 0.15 mmol) the title compound (62 mg, 83%) was obtained following trituration with ether; MS: 673 m/z (M+H)$^+$.

Example 66
Synthesis of Intermediate 11Y ($R^6+R^7=OCH_2CH_2O$; $R^1$=Bn; Y=NEt; Q=CONHCH$_2$CH$_2$SO$_2$ (5-(2-pyridinyl) thiophen-2-yl))

N-(2-((5-(Pyridin-2-yl)thiophen-2-yl)sulfonylamino) ethyl)-3-(3,4-Dihydro-6,7-ethylenedior-2H-1,2- benzothiazine-3-carboxamido)-2-(R,S)-hydroxy-3-(S)-benzylpropanamide 1,1-dioxide This compound was prepared according to the procedure used to synthesize 11s. From compound 8s (62.0 mg, 0.2 mmol, prepared from L-DOPA) and N-(2-((5-(pyridin-2-yl) thiophen-2-yl)sulfonylamino)ethyl)-2-(R,S)-hydroxy-3-(S)-benzyl-3-aminopropanamide, HCl salt (100 mg, 1.20 eq) the title compound (81.0 mg, 54%) was obtained; MS: 756 $(M+H)^+$.

Example 67

Synthesis of Intermediate 11Z ($R^6+R^7=OCH_2CH_2O$; $R^1$=Bn; Y=NEt; Q=CONH($CH_2$)$_3$NHSO$_2$ (4-F-Ph) )

3-((3,4-Dihydro-6,7-ethylenedioxy-2-ethyl-2H-1,2-benzothiazine-3-carbonyl)amino)-3-(S)-benzyl-2-(R,S)-hydroxy-N-(3-(4-fluorobenzenesulfonylamino)propyl) propanamide 1,1-dioxide This compound was prepared according to General Procedure G. From 8s (prepared from L-DOPA, 30 mg, 0.10 mmol) and 3-amino-3-(S)-benzyl-2-(R,S)-hydroxy-N-(3-(4-fluorobenzenesulfonylamino)propyl)propanamide hydrochloride (43 mg, 0.12 mmol) the title compound (40 mg, 59%) was obtained following preparative tlc on silica gel (ethyl acetate); MS: 705 m/z $(M+H)^+$.

Example 68

Synthesis of Intermediate 11AA ($R^6+R^7=OCH_2CH_2O$; $R^1$=Bn; Y=NEt; Q=CONH($CH_2$)$_3$NHSO$_2$Ph)

3-((3,4-Dihydro-6,7-ethylenedioxy-2-ethyl-2H-1,2-benzothiazine-3-carbonyl)amino)-3-(S)-benzyl-2-(R,S)-hydroxy-N-(3-(benzenesulfonylamino)propyl) propanamide 1,1-dioxide This compound was prepared according to General Procedure G. From 8s (prepared from L-DOPA, 30 mg, 0.10 mmol) and 3-amino-3-(S)-benzyl-2-(R,S)-hydroxy-N-(3-(benzenesulfonylamino)propyl)propanamide hydrochloride (41 mg, 0.12 mmol) the title compound (38 mg, 58%) was obtained following preparative tlc on silica gel (ethyl acetate); MS: 687 m/z $(M+H)^+$.

Example 69

Synthesis of Intermediate 11AC ($R^6+R^7=OCH_2CH_2O$; $R^1$=Bn; Y=NEt; Q=CONHCH$_2$CH$_2$NHSO$_2$(4-F-Ph))

3-((3,4-Dihydro-6,7-ethylenedioxy-2-ethyl-2H-1,2-benzothiazine-3-carbonyl)amino)-3-(S)-benzyl-2-(R,S)-hydroxy-N-(2-(4-fluorobenzenesulfonylamino)ethyl) propanamide 1,1-dioxide This compound was prepared according to General Procedure G. From 8s (prepared from L-DOPA, 30 mg, 0.10 mmol) and 3-amino-3-(S)-benzyl-2-(R,S)-hydroxy-N-(2-(4-fluorobenzenesulfonylamino)ethyl)propanamide hydrochloride (54 mg, 0.12 mmol) the title compound (48 mg, 77%) was obtained following preparative tlc on silica gel (ethyl acetate); MS: 691 m/z $(M+H)^+$.

Example 70

Synthesis of Intermediate 11AD ($R^6+R^7=OCH_2CH_2O$; $R^1$=Bn; Y=NH; Q=CONHBu)

N-Butyl-3-(3,4-Dihydro-6,7-ethylenedioxy-2H-1,2-benzothiazine-3-carboxamido)-2-(R,S)-hydroxy-3-(S)-benzylpropanamide 1,1-dioxide Compound 7r was prepared from compound 19 according to the procedure described for synthesis of 8s. Compound 11AD was prepared according to General Procedure G. From compound 7r (22 mg, 0.077 mmol) and N-butyl 2-(R,S)-hydroxy-3-(S)-benzyl-3-aminopropanamide, HCl salt (27.6 mg, 1.25 eq) (Harbeson, S. L., et al.; *J. Med. Chem.*, 1994, 37, 2918–2929) the title compound (20.0 mg, 50%) was obtained; MS: 518 $(M+H)^+$.

Example 71

Synthesis of Intermediate 11AE ($R^6+R^7=OCH_2CH_2O$; $R^1$=Bn; Y=NH; Q=CONHCH$_2$CH$_2$NHSO$_2$Ph)

N-(2-(Benzenesulfonylamino)ethyl)-3-(3,4-Dihydro-6,7-ethylenedioxy-2H-1,2-benzothiazine-3-carboxamido)-2-(R,S)-hydroxy-3-(S)-benzylpropanamide 1,1-dioxide Compound 11AE was prepared according to the procedure used to synthesize 11S. From compound 7r (28.5 mg, 0.1 mmol) and N-(2-(benzenesulfonylamino)ethyl)-2-(R,S)-hydroxy-3-(S)-benzyl-3-aminopropanamide, HCl salt (51.68 mg, 1.25 eq) the title compound (47.0 mg, 73%) was obtained; MS: 645 $(M+H)^+$.

Example 72

General Procedure H: Acetal Hydrolysis
Synthesis of Aldehyde 12a ($R^6=R^7=OCH_3$; $R^1$=i-Bu; Y=O; Q=H)

N-(3,4-Dihydro-6,7-dimethoxy-2,1-benzoxathiin-3-carbonyl)-L-leucinal 1,1-dioxide A solution of compound 10a (16 mg, 0.035 mmol) in a mixture of acetone/water (0.5 ml/0.75 ml) was treated with p-TsOH-H$_2$O (7 mg, 0.037 mmol). After being stirred overnight at ambient temperature the mixture was brought to reflux for one hour, cooled to ambient temperature and extracted into ethyl acetate. The organic phase was washed with saturated aqueous sodium bicarbonate, water, brine, dried (MgSO$_4$), filtered and concentrated to afford 10 mg (77%) of the title compound as a mixture of diastereomers; MS: 386 m/z $(M+H)^+$, 408 m/z $(M+Na)^+$.

Example 73

General Procedure I: Dess-Martin Oxidation
Synthesis of Aldehyde 12b ($R^6=R^7=OCH_3$; $R^1$=Bn; Y=O; Q=H)

N-(3,4-Dihydro-6,7-dimethoxy-2,1-benzoxathiin-3-carbonyl)-L-phenylalaninal 1,1-dioxide A solution of compound 11b (30 mg, 0.071 mmol) in dichloromethane (10 ml) chilled in an ice-water bath was treated with 1,1,1-triacetoxy-1,1-dihydro-1,2-benziodoxol-3 (1H)-one (Dess-Martin periodinane, DMP; 60 mg, 0.14 mmol). After one hour tlc analysis indicated complete consumption of starting material. The mixture was stirred for five minutes with 10% aqueous sodium thiosulfate solution and poured into a separatory funnel. The organic phase was washed once more with 10% sodium thiosulfate followed by saturated aqueous sodium bicarbonate (2×), water, brine, dried (MgSO$_4$), filtered and concentrated to afford 30 mg (99%) of the title compound as an off-white amorphous solid; MS: 420 m/z $(M+H)^+$.

Example 74

Synthesis of Aldehyde 12c ($R^6=R^7=OCH_3$; $R^1$=Bn; Y=NH; Q=H)

N-(3,4-Dihydro-6,7-dimethoxy-2H-1,2-benzothiazine-3-carbonyl)-L-phenylalaninal 1,1-dioxide This compound was prepared according to General Procedure I. From compound 11c (isomer 1; 20 mg, 0.048 mmol) the title compound (18 mg, 90%) was obtained as a pale yellow solid; MS: 417 m/z (M–H)$^-$.

Example 75

Synthesis of Aldehyde 12d ($R^6=R^7=OCH_3$; $R^1$=Bn; Y=NH; Q=H)

N-(3,4-Dihydro-6,7-dimethoxy-2H-1,2-benzothiazine-3-carbonyl)-L-phenylalaninal 1,1-dioxide This compound was prepared according to General Procedure I. From compound 11c (isomer 2; 35 mg, 0.083

Example 76
Synthesis of Aldehyde 12e ($R^6=R^7=OCH_3$; $R^1=Bn$; $Y=NCH_3$; Q=H)

N-(3,4-Dihydro-6,7-dimethoxy-2-methyl-2H-1,2-benzothiazine-3-carbonyl)-L-phenylalaninal 1,1-dioxide This compound was prepared according to General Procedure I. From compound 11e (isomer 1; 50 mg, 0.12 mmol) the title compound (48 mg, 96%) was obtained as a white solid; MS: 433 m/z $(M+H)^+$, 455 m/z $(M+Na)^+$.

Example 77
Synthesis of Aldehyde 12f ($R_6=R_7=OCH_3$; $R_1=Bn$; $Y=NCH_3$; Q=H)

N-(3,4-Dihydro-6,7-dimethoxy-2-methyl-2H-1,2-benzothiazine-3-carbonyl)-L-phenylalaninal 1,1-dioxide This compound was prepared according to General Procedure I. From compound 11e (isomer 2; 50 mg, 0.12 mmol) the title compound (47 mg, 94%) was obtained as a white solid; MS: 433 m/z $(M+H)^+$, 455 m/z $(M+Na)^+$.

Example 78
Synthesis of Aldehyde 12g ($R^6=R^7=OCH_3$; $R^1=Bn$; $Y=NBn$; Q=H)

N-(2-Benzyl-3,4-dihydro-6,7-dimnethoxy-2H-1,2-benzothiazine-3-carbonyl)-L-phenylalaninal 1,1-dioxide This compound was prepared according to General Procedure I. From compound 11g (isomer 1; 25 mg, 0.05 mmol) the title compound (23 mg, 82%) was obtained; MS: 509 m/z $(M+H)^+$, 531 m/z $(M+Na)^+$.

Example 79
Synthesis of Aldehyde 12h ($R^6=R^7=OCH_3$; $R^1=Bn$; $Y=NBn$; Q=H)

N-(2-Benzyl-3,4-dihydro-6,7-dimethoxy-2H-1,2-benzothiazine-3-carbonyl)-L-phenylalaninal 1,1-dioxide This compound was prepared according to General Procedure I. From compound 11g (isomer 2; 28 mg, 0.06 mmol) the title compound (20 mg, 71%) was obtained; MS: 509 m/z $(M+H)^+$, 531 m/z $(M+Na)^+$.

Example 80
Synthesis of Aldehyde 12i ($R^6=H$; $R^7=H$; $R^1=Bn$; $Y=NCH_3$; Q=H)

N-(3,4-Dihydro-2-methyl-2H-1,2-benzothiazine-3-carbonyl)-L-phenylalaninal 1,1-dioxide This compound was prepared according to General Procedure I. From 11i (isomer 1; 107 mg, 0.29 mmol) the title compound (84 mg, 79%) was obtained; MS: 373 m/z $(M+H)^+$.

Example 81
Synthesis of Aldehyde 12j ($R^6=H$; $R^7=H$; $R^1=Bn$; $Y=NCH_3$; Q=H)

N-(3,4-Dihydro-2-methyl-2H-1,2-benzothiazine-3-carbonyl)-L-phenylalaninal 1,1-dioxide This compound was prepared according to General Procedure I. From 11i (isomer 2; 76 mg, 0.20 mmol) the title compound (64 mg, 84%) was obtained; MS: 373 m/z $(M+H)^+$.

Example 82
Synthesis of Aldehyde 12k ($R^6=F$; $R^7=H$; $R^1=Bn$; $Y=NCH_3$; Q=H)

N-(3,4-Dihydro-2-methyl-6-fluoro-2H-1,2-benzothiazine-3-carbonyl)-L-phenylalaninal 1,1-dioxide mmol) the title compound (32 mg, 91%) was obtained as a pale yellow solid; MS: 417 m/z $(M-H)^-$.

This compound was prepared according to General Procedure I. From 11k (41 mg, 0.10 mmol) the title compound (33 mg, 83%) was obtained as a white solid; MS: 391 m/z $(M+H)^+$.

Example 83
Synthesis of Aldehyde 12-l ($R^6=R^7=Cl$; $R^1=Bn$; $Y=NCH_3$; Q=H)

N-(3,4-Dihydro-6,7-dichloro-2-methyl-2H-1,2-benzothiazine-3-carbonyl)-L-phenylalaninal 1,1-dioxide This compound was prepared according to General Procedure I. From 11-l (isomer 1; 32 mg, 0.07 mmol) the title compound (27 mg, 84%) was obtained; MS: 441, 443, 445 m/z $(M+H)^+$ ($Cl_2$ pattern).

Example 84
Synthesis of Aldehyde 12m ($R^6=R^7=Cl$; $R^1=Bn$; $Y=NCH_3$; Q=H)

N-(3,4-Dihydro-6,7-dichloro-2-methyl-2H-1,2-benzothiazine-3-carbonyl)-L-phenylalaninal 1,1-dioxide This compound was prepared according to General Procedure I. From 11-l (isomer 2; 50 mg, 0.11 mmol) the title compound (45 mg; 90%) was obtained; MS: 441, 443, 445 m/z $(M+H)^+$ ($Cl_{12}$ pattern).

Example 85
Synthesis of Aldehyde 12n ($R^6=Cl$; $R^7=H$; $R^1=Bn$; $Y=N$-i-Bu; Q=H)

N-(3,4-Dihydro-6-chloro-2-isobutyl-2H-1,2-benzothiazine-3-carbonyl)-L-phenylalaninal 1,1-dioxide This compound was prepared according to General Procedure I. From 11n (isomer 1; 41 mg, 0.09 mmol) the title compound (36 mg; 88%) was obtained; MS: 449, 451 m/z $(M+H)^+$ (chloride isotope pattern).

Example 86
Synthesis of Aldehyde 12o ($R^6=Cl$; $R^7=H$; $R^1=Bn$; $Y=N$-i-Bu; Q=H)

N-(3,4-Dihydro-6-chloro-2-isobutyl-2H-1,2-benzothiazine-3-carbonyl)-L-phenylalaninal 1,1-dioxide This compound was prepared according to General Procedure I. From 11n (isomer 2; 41 mg, 0.09 mmol) the title compound (37 mg, 90%) was obtained; MS: 449, 451 m/z $(M+H)^+$. (chloride isotope pattern).

Example 87
Synthesis of Aldehyde 12p ($R^6=Cl$; $R^7=H$; $R^1=Bn$; $Y=NCH_3$; Q=H)

N-(6-Chloro-3,4-dihydro-2-methyl-2H-1,2-benzothiazine-3-carbonyl)-L-phenylalaninal 1,1-dioxide This compound was prepared according to General Procedure I. From compound 11p (isomer 1; 25 mg, 0.06 mmol) the title compound (21 mg, 84%) was obtained as an off-white solid; MS: 405, 407 m/z $(M+H)^+$.

Example 88
Synthesis of Aldehyde 12q ($R^6=Cl$; $R^7=H$; $R^1=Bn$; $Y=NCH_3$; Q=H)

N-(6-Chloro-3,4-dihydro-2-methyl-2H-1,2-benzothiazine-3-carbonyl)-L-phenylalaninal 1,1-dioxide This compound was prepared according to General Procedure I. From compound 11p (isomer 2; 25 mg, 0.06 mmol) the title compound (19 mg, 76%) was obtained as an off-white solid; MS: 405, 407 m/z $(M+H)^+$.

Example 89
Synthesis of Aldehyde 12r ($R^6+R^7=OCH_2CH_2O$; $R^1=Bn$; $Y=NCH_3$; Q=H)

N-(3,4-Dihydro-6,7-ethylenedioxy-2-methyl-2H-1,2-benzothiazine-3-carbonyl)-L-phenylalaninal 1,1-dioxide This compound was prepared according to General Procedure I. From compound 10r (100 mg, 0.23 mmol) the title compound (67 mg, 67%) was obtained as a buff-white solid; MS: 431 m/z (M+H)$^+$, 453 m/z (M+Na)$^+$.

Example 90

Synthesis of Aldehyde 12s (R$^6$+R$^7$=OCH$_2$CH$_2$O; R$^1$=Bn; Y=NEt; Q=H)

N-(3,4-Dihydro-6,7-ethylenedioxy-2-ethyl-2H-1,2-benzothiazine-3-carbonyl)-L-phenylalaninal 1,1-dioxide This compound was prepared according to General Procedure I. From compound 11s (isomer 1; 30 mg, 0.07 mmol) the title compound (25 mg, 83%) was obtained as a white amorphous solid; MS: 445 m/z (M+H)$^+$, 467 m/z (M+Na)$^+$.

Example 91

Synthesis of Aldehyde 12t (R$^6$+R$^7$=OCH$_2$CH$_2$O; R$^1$=Bn; Y=NEt; Q=H)

N-(3,4-Dihydro-6,7-ethylenedioxy-2-ethyl-2H-1,2-benzothiazine-3-carbonyl)-L-phenylalaninal 1,1-dioxide This compound was prepared according to General Procedure I. From compound 11s (isomer 2; 30 mg, 0.07 mmol) the title compound (27 mg, 90%) was obtained as a white amorphous solid; MS: 445 m/z (M+H)$^+$, 467 m/z (M+Na)$^+$.

Example 92

Synthesis of Aldehyde 12u (R$^6$+R$^7$=OCH$_2$CH$_2$O; R$^1$=Bn; Y=N-i-Pr; Q=H)

N-(3,4-Dihydro-6,7-ethylenedioxy-2-isopropyl-2H-1,2-benzothiazine-3-carbonyl)-L-phenylalaninal 1,1-dioxide This compound was prepared according to General Procedure I. From 11u (78 mg, 0.17 mmol) the title compound (63 mg, 81%) was obtained as a white solid; MS: 459 m/z (M+H)$^+$.

Example 93

Synthesis of Aldehyde 12v (R$^6$+R$^7$=OCH$_2$CH$_2$O; R$^1$=i-Bu; Y=NEt; Q=H)

N-(3,4-Dihydro-6,7-ethylenediowcy-2-ethyl-2H-1,2-benzothiazine-3-carbonyl)-L-leucinal 1,1-dioxide This compound was prepared according to General Procedure H. From 10v (isomer 1; 158 mg, 0.32 mmol) the title compound (119 mg, 89%) was obtained as a white solid; NMR (CDCl$_3$) δ 0.96 (t, J=7 Hz, 6H), 1.07 (t, J=7 Hz, 3H) 1.22 (m, 1H), 1.74 (m, 2H), 2.95 (m, 1H), 3.25–3.35 (m, 3H), 3.95 (m, 1H), 4.29 (br, 4H), 4.46 (m, 1H), 6.83 (s, 1H), 7.25 (br, 1H), 7.34 (s, 1H), 9.55 (s, 1H); MS: 411 m/z (M+H)$^+$.

Example 94

Synthesis of Aldehyde 12w (R$^6$+R$^7$=OCH$_2$CH$_2$O; R$_1$=i-Bu; Y=NEt; Q=H)

N-(3,4-Dihydro-6,7-ethylenedioxy-2-ethyl-2H-1,2-benzothiazine-3-carbonyl)-L-leucinal 1,1-dioxide This compound was prepared according to General Procedure H. From 10v (isomer 2; 155 mg, 0.32 mmol) the title compound (118 mg, 89%) was obtained as a white solid; NMR (CDCl$_3$) δ 0.95 (t, J=7 Hz, 6H), 1.07 (t, J=7 Hz, 3H), 1.20 (m, 1H), 1.73 (m, 2H), 2.99 (m, 1H), 3.16–3.45 (m, 3H), 3.83 (m, 1H), 4.29 (br, 4H), 4.57 (m, 1H), 6.83 (s, 1H) 7.25 (br, 1H), 7.34 (s, 1H), 9.57 (s, 1H); MS: 411 m/z (M+H)$^+$.

Example 95

Synthesis of Aldehyde 12x (R$^6$+R$^7$=OCH$_2$CH$_2$O; R$^1$=(CH$_2$)$_4$ NHSO$_2$Ph; Y=NEt; Q=H)

N$_\alpha$-(3,4-Dihydro-6,7-ethylenedioxy-2-methyl-2H-1,2-benzothiazine-3-carbonyl)-L-N$_\epsilon$-(benzenesulfonyl)lysinal 1,1-dioxide This compound was prepared according to General Procedure I. From 11x (isomer 1; 30 mg, 0.05 mmol) the title compound (27 mg, 90%) was obtained as a white solid; MS: 552 m/z (M+H)$^+$.

Example 96

Synthesis of Aldehyde 12y (R$^6$+R$^7$=OCH$_2$CH$_2$O; R$^1$=(CH$_2$)$_4$ NHSO$_2$Ph; Y=NEt; Q=H)

N$_\alpha$-(3,4-Dihydro-6,7-ethylenedioxy-2-methyl-2H-1,2-benzothiazine-3-carbonyl)-L-N$_\epsilon$-(benzenesulfonyl)lysinal 1,1-dioxide This compound was prepared according to General Procedure I. From 11x (isomer 1; 30 mg, 0.05 mmol) the title compound (28 mg, 93%) was obtained as a white solid; MS: 552 m/z (M+H)$^+$.

Example 97

Synthesis of Aldehyde 12z (R$^6$+R$^7$=OCH$_2$CH$_2$O; R$^1$=Bn; Y=NCH$_3$; Q=H)

N-(3,4-Dihydro-6-(4-morpholino)-2-methyl-2H-1,2-benzothiazine-3-carbonyl)-L-phenylalaninal 1,1-dioxide This compound was prepared according to General Procedure I. From 11z (isomer 1; 63 mg, 0.14 mmol) the title compound (56 mg, 89%) was obtained; MS: 458 m/z (M+H)$^+$.

Example 98

Synthesis of Aldehyde 12aa (R$^6$+R$^7$=OCH$_2$CH$_2$O; R$^1$=Bn; Y=NCH$_3$; Q=H)

N-(3,4-Dihydro-6-(4-morpholino)-2-methyl-2H-1,2-benzothiazine-3-carbonyl)-L-phenylalaninal 1,1-dioxide This compound was prepared according to General Procedure I. From 11z (isomer 2; 102 mg, 0.22 mmol) the title compound (91 mg, 89%) was obtained; MS: 458 m/z (M+H)$^+$.

Example 99

Synthesis of Ester 13 (R$^6$+R$^7$=OCH$_2$CH$_2$O; R$^1$=Bn; Y=NEt; Q=CO$_2$Me)

Methyl 3-(3,4-Dihydro-6,7-ethylenedioxy-2-ethyl-2H-1,2-benzothiazine-3-carboxamido)-2-oxo-3-(S)-benzylpropionic acid 1,1-dioxide To a solution of 283 mg (0.9 mmol) of compound 8s (from L-DOPA) in 10.0 ml of DMF at 0° C. was added 298 ul (3.0 eq) of NMM, 277.5 mg (1.25 eq) of methyl 2-(R,S)-hydro-3-(S)-benzyl-3-aminopropionic acid hydrochloride salt, 122.1 mg (1.0 eq) of HOBt and 399.1 mg (1.2 eq) of BOP. After 5 min, the ice bath was removed and the reaction was stirred at room temperature for 3 hours. The DMF was removed under reduced pressure and the residue was diluted with CH$_2$Cl$_2$ (40 ml). The CH$_2$Cl$_2$ solution was washed with water, 3% of citric acid, 5% of NaHCO$_3$, brine and dried. Purification by flash chromatography (20% hexane in EtOAc) gave 428 mg (94%) of methyl 3-(3,4-Dihydro-6,7-ethylenedioxy-2-ethyl-2H-1,2-benzothiazine-3-carboxamido)-2(R,S)-hydroxy-3-(S)-benzylpropionic acid 1,1-dioxide (11; R$^6$+R$^7$=OCH$_2$CH$_2$O; R$^1$=Bn; Y=NEt; Q=CO$_2$Me): MS: 505 m/z (M+H)$^+$.

To a solution of 428 mg (0.85 mmol) of this intermediate in 40 ml of CH$_2$Cl$_2$ at 0° C. was added 720 mg (1.7 mmol) of 1,1,1-triacetoxy-1,1-dihydro-1,2-benziodoxol-3(1H)-one (Dess-Martin reagent). After 5 min, the ice-bath was removed and the reaction was stirred at room temperature for 2 hours. More CH$_2$Cl$_2$ (30 ml) was added to the reaction, and the product was washed with 10% of sodium thiosulfate (3×20 ml), water, brine and dried. Evaporation gave 404 mg (95%) of the product; MS: 405 m/z (M+H)$^+$.

Example 100

Synthesis of Ketoamide 14A ($R^6$=Cl; $R^7$=H; $R^1$=Bn; Y=NCH$_3$; Q=CONHEt)

N-Ethyl-3-(6-chloro-3,4-dihydro-2-methyl-2H-1,2-benzothiazine-3-carboxamido)-2-oxo-3-(S)-benzylpropanamide 1,1-dioxide This compound was prepared according to General Procedure I. From compound 11A (Q=CONHEt) (58 mg, 0.12 mmol) the title compound (35 mg, 61%) was obtained as a mixture of diastereomers; MS: 478 m/z (M+H)$^+$; 500 m/z (M+Na)$^+$.

Example 101

Synthesis of Ketoamide 14B ($R^6$+$R^7$=OCH$_2$CH$_2$O; $R^1$=i-Bu; Y=NEt; Q=CONHBu)

3-((3,4-Dihydro-6,7-ethylenedioxy-2-ethyl-2H-1,2-benzothiazine-3-carbonyl)amino)-3-(S)-isobutyl-2-oxo-N-butylpropanamide 1,1-dioxide This compound was prepared according to General Procedure I. From 11B ($R^6$+$R^7$=OCH$_2$CH$_2$O; $R^1$=i-Bu; Y=NEt; Q=CONHBu; 38 mg, 0.07 mmol) the title compound (26 mg, 68%) was obtained; MS: 510 m/z (M+H)$^+$.

Example 102

Synthesis of Ketoamide 14C ($R^6$+$R^7$=OCH$_2$CH$_2$O; $R^1$=i-Bu; Y=NEt; Q=CONHBu)

3-((3,4-Dihydro-6,7-ethylenedioxy-2-ethyl-2H-1,2-benzothiazine-3-carbonyl)amino)-3-(S)-isobutyl-2-oxo-N-butylpropanamide 1,1-dioxide This compound was prepared according to General Procedure I. From 11C ($R^6$+$R^7$=OCH$_2$CH$_2$O; $R^1$=i-Bu; Y=NEt; Q=CONHBu; 76 mg, 0.15 mmol) the title compound (56 mg, 74%) was obtained; MS: 510 m/z (M+H)$^+$.

Example 103

Synthesis of Ketoamide 14D ($R^6$+$R^7$=OCH$_2$CH$_2$O; $R^1$=Bn; Y=NEt; Q=CONHEt)

N-Ethyl-3-(3,4-Dihydro-6,7-ethylenedioxy-2H-1,2-benzothiazine-3-carboxamido)-2-oxo-3-(S)-benzylpropanamide 1,1-dioxide This compound was prepared according to General Procedure G. From 8s (31.3 mg, 0.1 mmol, prepared from L-DOPA) and N-ethyl-2-oxo-3-(S)-benzyl-3-aminopropanamide, HCl salt (31.94 mg, 1.25 eq) the title compound (5.0 mg, 10%) was obtained; MS: 516 (M+H)$^+$. N-Ethyl-2-oxo-3-(S)-benzyl-3-aminopropanamide, HCl salt was prepared according to Rich's procedure (Ocain, T. D.; Rich, D. H. *J. Med. Chem.* 1992, 35, 451–456, incorporated by reference herein in its entirety). However, oxidation to the Boc ketoamide was accomplished with Dess-Martin periodinane (General Procedure I).

Example 104

Synthesis of Ketoamide 14E ($R^6$+$R^7$=OCH$_2$CH$_2$O; $R^1$=Bn; Y=NEt; Q=CONHBu)

3-((3,4-Dihydro-6,7-ethylenedioxy-2-ethyl-2H-1,2-benzothiazine-3-carbonyl)amino)-3-(S)-benzyl-2-oxo-N-butylpropanamide 1,1-dioxide This compound was prepared according to General Procedure I. From 11E ($R^6$+$R^7$=OCH$_2$CH$_2$O; $R^1$=Bn; Y=NEt; Q=CONHBu; 50 mg, 0.09 mmol) the title compound (49 mg, 98%) was obtained; MS: 544 m/z (M+H)$^+$.

Example 105

Synthesis of Ketoamide 14F ($R^6$+$R^7$=OCH$_2$CH$_2$O; $R^1$=Bn; Y=NEt; Q=CONHBu)

3-((3,4-Dihydro-6,7-ethylenedioxy-2-ethyl-2H-1,2-benzothiazine-3-carbonyl)amino)-3-(S)-benzyl-2-oxo-N-butylpropanamide 1,1-dioxide This compound was prepared according to General Procedure I. From 11F ($R^6$+$R^7$=OCH$_2$CH$_2$O; $R^1$=Bn; Y=NEt; Q=CONHBu; 65 mg, 0.12 mmol) the title compound (52 mg, 80%) was obtained; MS: 544 m/z (M+H)$^+$.

Example 106

General Procedure J: Synthesis of α-Ketoamides from α-Ketoesters

Synthesis of Ketoamide 14G ($R^6$+$R^7$=OCH$_2$CH$_2$O; $R^1$=Bn; Y=NEt; Q=CONHBu)

N-Butyl-3-(3,4-Dihydro-6,7-ethylenedioxy-2-ethyl-2H-1,2-benzothiazine-3-carboxamido)-2-oxo-3-benzylpropanamide 1,1-dioxide Compound 13 (23 mg, 0.046 mmol) and 0.2 ml of butylamine were stirred neat at room temperature overnight. LC-MS analysis indicated completion of the reaction. The reaction was diluted with EtOAc (20 ml) and cooled to 0° C. as 5.0 ml of 2N HCl was added to decompose the imine product formed in the reaction. The aqueous mixture was stirred for 30 min and extracted with EtOAc (3×10 ml). The combined organic layers were washed with water, 5% of NaHCO$_3$, brine and dried. Filtration and evaporation afforded 20.5 mg (82%) of the product; MS: 615 m/z (M+H)$^+$.

Example 107

Synthesis of Ketoamide 14H ($R^6$+$R^7$=OCH$_2$CH$_2$O; $R^1$=Bn; Y=NEt; Q=CONHCH$_2$CH$_2$OCH$_3$)

N-(2-Methoxyethyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from 2-methoxyethylamine; 84% yield; MS: 546 m/z (M+H)$^+$.

Example 108

Synthesis of Ketoamide 14I ($R^6$+$R^7$=OCH$_2$CH$_2$O; $R^1$=Bn; Y=NEt; Q=CONH-iPr)

N-Isopropyl-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from isopropylamine; 85% yield; MS: 592 m/z (M+H)$^+$.

Example 109

Synthesis of Ketoamide 14J ($R^6$+$R^7$=OCH$_2$CH$_2$O; $R^1$=Bn; Y=NEt; Q=CONH(CH$_2$)$_4$CH$_3$)

N-Pentyl-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from pentylamine; 93% yield; MS: 558 m/z (M+H)$^+$.

Example 110

Synthesis of Ketoamide 14K ($R^6$+$R^7$=OCH$_2$CH$_2$O; $R^1$=Bn; Y=NEt; Q=CONHCH$_2$Ph)

N-Benzyl-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from benzylamine; 80% yield; MS: 578 m/z (M+H)$^+$.

Example 111
Synthesis of Ketoamide 14L ($R^6+R^7$=OCH$_2$CH$_2$O; $R^1$=Bn; Y=NEt; Q=CONHCH$_2$CH$_2$Ph)

N-Phenethyl-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from phenethylamine; 85% yield; MS: 592 m/z (M+H)$^+$.

Example 112
Synthesis of Ketoamide 14M ($R^6+R^7$=OCH$_2$CH$_2$O; $R^1$=Bn; Y=NEt; Q=CONHCH$_2$CH=CH$_2$)

N-(2-Propenyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from allylamine; 91% yield; MS: 551 m/z (M+H)$^+$.

Example 113
Synthesis of Ketoamide 14N ($R^6+R^7$=OCH$_2$CH$_2$O; $R^1$=Bn; Y=NEt; Q=CONHCH$_2$CH$_2$CH$_2$-(imidazol-1-yl))

N-(3-(Imidazol-1-yl)propyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from 3-imidazolylpropylamine; 11% yield; MS: 596 m/z (M+H)$^+$.

Example 114
Synthesis of Ketoamide 14-O ($R^6+R^7$=OCH$_2$CH$_2$O; $R^1$=Bn; Y=NEt; Q=CONHCH$_2$CH$_2$CH$_2$-(2-ketopyrrolidin-1-yl))

N-(3-(2-Ketopyrrolidin-1-yl)propyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from 3-(2-ketopyrrolidin-1-yl)propylamine; 68% yield; MS: 613 m/z (M+H)$^+$.

Example 115
Synthesis of Ketoamide 14P ($R^6+R^7$=OCH$_2$CH$_2$O; $R^1$=Bn; Y=NEt; Q=CONHCH$_2$CH$_2$CH$_2$(morpholin-4-yl))

N-(3-(Morpholin-4-yl)propyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from 3-(morpholin-4-yl)propylamine; 84% yield; MS: MS: 615 m/z (M+H)$^+$.

Example 116
Synthesis of Ketoamide 14Q ($R^6+R^7$=OCH$_2$CH$_2$O; $R^1$=Bn; Y=NEt; Q=CONHCH$_2$(pyridin-2-yl))

N-(Pyridin-2-ylmethyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from 2-(aminomethyl)pyridine; 82.5% yield; MS: 579 m/z (M+H)$^+$.

Example 117
Synthesis of Ketoamide 14R ($R^6+R^7$=OCH$_2$CH$_2$O; $R^1$=Bn; Y=NEt; Q=CONHCH$_2$cyclopropyl)

N-(Cyclopropylmethyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from aminomethylcyclopropane; 96.6% yield; MS: 542 m/z (M+H)$^+$.

Example 118
Synthesis of Ketoamide 14S ($R^6+R^7$=OCH$_2$CH$_2$O; $R^1$=Bn; Y=NEt; Q=CONHCH$_2$CH$_2$NHSO$_2$CH$_3$)

N-(2-(Methanesulfonylamino)ethyl)-3-(3,4-Dihydro-6,7-ethylenedioxy-2H-1, 2-benzothiazine-3-carboxamido)-2-oxo-3-(S)-benzylpropanamide 1,1-dioxide This compound was prepared according to General Procedure I. From compound 11S (45.0 mg, 0.074 mmol) the title compound (34.0 mg, 75%) was obtained; MS: 609 (M+H)$^+$.

Example 119
Synthesis of Ketoamide 14T ($R^6+R^7$=OCH$_2$CH$_2$O; $R^1$=Bn; Y=NEt; Q=CONHCH$_2$CH$_2$NHSO$_2$(4-NO$_2$-Ph))

3-((3,4-Dihydro-6,7-ethylenedioxy-2-ethyl-2H-1,2-benzothiazine-3-carbonyl)amino)-3-(S)-benzyl-2-oxo-N-(2-(4-nitrobenzenesulfonylamino)ethyl)propanamide 1,1-dioxide This compound was prepared according to General Procedure I. From 11T ($R^6+R^7$=OCH$_2$CH$_2$O; $R^1$=Bn; Y=NEt; Q=CONHCH$_2$CH$_2$NHSO$_2$(4-NO$_2$-Ph); 50 mg, 0.07 mmol) the title compound (31 mg, 62%) was obtained as a pale yellow solid; MS: 716 m/z (M+H)$^+$.

Example 120
Synthesis of Ketoamide 14U ($R^6+R^7$=OCH$_2$CH$_2$O; $R^1$=Bn; Y=NEt; Q=CONH(CH$_2$)$_3$NHSO$_2$(4—NO$_2$-Ph))

3-((3,4-Dihydro-6,7-ethylenedioxy-2-ethyl-2H-1,2-benzothiazine-3-carbonyl)amino)-3-(S)-benzyl-2-oxo-N-(3-(4-nitrobenzenesulfonylamino)propyl)propanamide 1,1-dioxide This compound was prepared according to General Procedure I. From 11U ($R^6+R^7$=OCH$_2$CH$_2$O; $R^1$=Bn; Y=NEt; Q=CONH(CH$_2$)$_3$NHSO$_2$(4-NO$_2$-Ph), 30 mg, 0.04 mmol) the title compound was obtained (24 mg, 80%) as a pale yellow solid; MS: 730 m/z (M+H)$^+$.

Example 121
Synthesis of Ketoamide 14V ($R^6+R^7$=OCH$_2$CH$_2$O; $R^1$=Bn; Y=NEt; Q=CONHCH$_2$CH$_2$NHSO$_2$(3,4-Cl$_2$-Ph))

3-((3,4-Dihydro-6,7-ethylenedioxy-2-ethyl-2H-1,2-benzothiazine-3-carbonyl)amino)-3-(S)-benzyl-2-oxo-N-(2-(3,4-dichlorobenzenesulfonylamino)ethyl)propanamide 1,1-dioxide This compound was prepared according to General Procedure I. From 11V ($R^6+R^7$=OCH$_2$CH$_2$O; $R^1$=Bn; Y=NEt; Q=CONHCH$_2$CH$_2$NHSO$_2$(3,4-Cl$_2$-Ph); 58 mg, 0.08 mmol) the title compound (44 mg, 76%) was obtained as a pale yellow solid; MS: 716 m/z (M+H)$^+$.

Example 122
Synthesis of Ketoamide 14W ($R^6+R^7$=OCH$_2$CH$_2$O; $R^1$=Bn; Y=NEt; Q=CONH(CH$_2$)$_3$NHSO$_2$(3,4-Cl$_2$-Ph))

3-((3,4-Dihydro-6,7-ethylenedioxy-2-ethyl-2H-1,2-benzothiazine-3-carbonyl)amino)-3-(S)-benzyl-2-oxo-N-(3-(3,4-dichlorobenzenesulfonylamino)propyl)propanamide 1,1-dioxide This compound was prepared according to General Procedure I. From 11W ($R^6+R^7$=OCH$_2$CH$_2$O; $R^1$=Bn; Y=NEt; Q=CONH(CH$_2$)$_3$NHSO$_2$(3,4-Cl$_2$-Ph); 56 mg, 0.07 mmol) the title compound (40 mg, 71%) was obtained as a pale yellow solid; MS: 753 m/z (M+H)$^+$.

Example 123
Synthesis of Ketoamide 14X ($R^6+R^7$=OCH$_2$CH$_2$O; $R^1$=Bn; Y=NEt; Q=CONHCH$_2$CH$_2$NHSO$_2$Ph)

3-((3,4-Dihydro-6,7-ethylenedioxy-2-ethyl-2H-1,2-benzothiazine-3-carbonyl)amino)-3-(S)-benzyl-2-oxo-N-(2-(benzenesulfonylamino)ethyl)propanamide 1,1-dioxide

Example 124
Synthesis of Ketoamide 14Y ($R^6+R^7$=OCH$_2$CH$_2$O; $R^1$=Bn; Y=NEt; Q=CONHCH$_2$CH$_2$SO$_2$(5-(2-pyridinyl)thiophen-2-yl))

N-(2-((5-(Pyridin-2-yl)thiophen-2-yl)sulfonylamino)ethyl)-3-(3,4-Dihydro-6,7-ethylenedioxy-2H-1,2-benzothiazine-3-carboxamido)-2-oxo-3-(S)-benzylpropanamide 1,1-dioxide This compound was prepared according to General Procedure I. From 11X ($R^6+R^7$=OCHC$_2$H$_2$O; $R^1$=Bn; Y=NEt; Q=CONHCH$_2$CH$_2$NHSO$_2$Ph; 33 mg, 0.05 mmol) the title compound (28 mg, 85%) was obtained as a pale yellow solid; MS: 671 m/z (M+H)$^+$.

Example 124
Synthesis of Ketoamide 14Y ($R^6+R^7$=OCH$_2$CH$_2$O; $R^1$=Bn; Y=NEt; Q=CONHCH$_2$CH$_2$SO$_2$(5-(2-pyridinyl)thiophen-2-yl))

N-(2-((5-(Pyridin-2-yl)thiophen-2-yl)sulfonylamino)ethyl)-3-(3,4-Dihydro-6,7-ethylenedioxy-2H-1,2-benzothiazine-3-carboxamido)-2-oxo-3-(S)-benzylpropanamide 1,1-dioxide This compound was prepared according to General Procedure I. From compound 11Y (75.5 mg, 0.1 mmol) the title compound (80 mg, 93%) was obtained; MS: 754 (M+H)$^+$.

Example 125
Synthesis of Ketoamide 14Z ($R^6+R^7$=OCH$_2$CH$_2$O; $R^1$=Bn; Y=NEt; Q=CONH(CH$_2$)$_3$NHSO$_2$(4-F-Ph))

3-((3,4-Dihydro-6,7-ethylenedioxy-2-ethyl-2H-1,2-benzothiazine-3-carbonyl)amino)-3-(S)-benzyl-2-oxo-N-(3-(4-fluorobenzenesulfonylamino)propyl)propanamide 1,1-dioxide This compound was prepared according to General Procedure I. From 11Z; (35 mg, 0.05 mmol) the title compound (28 mg, 80%) was obtained as a pale yellow solid; MS: 703 m/z (M+H)$^+$.

Example 126
Synthesis of Ketoamide 14AA ($R^6+R^7$=OCH$_2$CH$_2$O; $R^1$=Bn; Y=NEt; Q=CONH(CH$_2$)$_3$NHSO$_2$Ph)

3-((3,4-Dihydro-6,7-ethylenedioxy-2-ethyl-2H-1,2-benzothiazine-3-carbonyl)amino)-3-(S)-benzyl-2-oxo-N-(3-(benzenesulfonylamino)propyl)propanamide 1,1-dioxide This compound was prepared according to General Procedure I. From 11AA; (34 mg, 0.05 mmol) the title compound (30 mg, 88%) was obtained as a pale yellow solid; MS: 685 m/z (M+H)$^+$.

Example 127
Synthesis of Ketoamide 14AB ($R^6+R^7$=OCH$_2$CH$_2$O; $R^1$=Bn; Y=NEt; Q=CONHCH$_2$-(pyridin-4-yl))

N-(Pyridin-4-ylmethyl)-3-(3,4-Dihydro-6,7-ethylenedioxy-2-ethyl-2H-1,2-benzothiazine-3-carboxamido)-2-oxo-3-benzylpropanamide 1,1-dioxide This compound was prepared according to General Procedure J from 4-pyridylmethylamine; 32% yield; MS: 579 m/z (M+H)$^+$.

Example 128
Synthesis of Ketoamide 14AC ($R^6+R^7$=OCH$_2$CH$_2$O; $R^1$=Bn; Y=NEt; Q=CONHCH$_2$CH$_2$NHSO$_2$(4-F-Ph))

3-((3,4-Dihydro-6,7-ethylenedioxy-2-ethyl-2H-1,2-benzothiazine-3-carbonyl)amino)-3-(S)-benzyl-2-oxo-N-(2-(4-fluorobenzenesulfonylamino)ethyl)propanamide 1,1-dioxide This compound was prepared according to General Procedure I. From 11AC; (45 mg, 0.07 mmol) the title compound (30 mg, 67%) was obtained as a pale yellow solid; MS: 689 m/z (M+H)$^+$.

Example 129
Synthesis of Ketoamide 14AD ($R^6+R^7$=OCH$_2$CH$_2$O; $R^1$=Bn; Y=NH; Q=CONHBu)

N-Butyl-3-(3,4-Dihydro-6,7-ethylenedioxy-2H-1,2-benzothiazine-3-carboxamido)-2-oxo-3-(S)-benzylpropanamide 1,1-dioxide This compound was prepared according to General Procedure I. From compound 11AD (20.0 mg, 0.037 mmol) the title compound (16.0 mg, 84%) was obtained; MS: 516 (M+H)$^+$.

Example 130
Synthesis of Ketoamide 14AE ($R^6+R^7$=OCH$_2$CH$_2$O; $R^1$=Bn; Y=NH; Q=CONHCH$_2$CH$_2$NHSO$_2$Ph)

N-(2-(Benzenesulfonylamino)ethyl)-3-(3,4-Dihydro-6,7-ethylenedioxy-2H-1,2-benzothiazine-3-carboxamido)-2-oxo-3-(S)-benzylpropanamide 1,1-dioxide This compound was prepared according to General Procedure I. From compound 11AE (47.0 mg, 0.073 mmol) the title compound (16.0 mg, 34%) was obtained; MS: 643 (M+H)$^+$.

Example 131
Synthesis of Intermediate 16.

3-(3,4-Dihydroxyphenyl)-L-alanine methyl ester hydrochloride

A solution of 1.97 g (10 mmol) of L-DOPA 15 in 100 ml of MeOH at 0° C. was added 6.57 ml (90 mmol) of thionyl chloride via addition funnel. The mixture was stirred overnight while the temperature was slowly warmed to room temperature. The solvent was evaporated and the thick oil was treated with toluene (3×15 ml) and evaporated. The yield of white solid was 3.26 g (100%); NMR (DMSO-d6) δ 2.90 (m, 2H), 3.38 (bs, 2H), 3.61 (s, 3H), 4.08 (m, 1H), 6.40 (d, 1H, J=7 Hz), 6.59 (s, 1H), 6.65(d, 2H, J=7 Hz), 8.59 (bs, 1H), 8.90 (d, 1H, J=10 Hz). MS: 212 m/z (M+H)$^+$.

Example 132
Synthesis of Intermediate 17.

N-(Benzyloxycarbonyl)-3-(3,4-dihydroxyphenyl)-L-alanine methyl ester

A suspension of 4.94 g (20 mmol) of compound 16 and 4.4 ml (2.0 eq) of N-methyl morpholine in 8 ml of THF and 1 ml of water was stirred at room temperature as 4.98 g (20 mmol) of benzyloxycarbonyloxy-succinimide in 8 ml of 1,4-dioxane was added dropwise. The reaction mixture was stirred overnight. The solvent was evaporated and the residue was diluted with ethyl acetate (100 ml). The ethyl acetate solution was washed with water (20 ml), 5% of NaHCO$_3$ (20 ml), 3% of citric acid (20 ml), brine (20 ml) and dried over MgSO$_4$. Filtration and concentration afforded 5.36 g (78%) of a white solid; NMR (CDCl$_3$) δ 2.99 (m, 2H), 3.65 (s, 3H), 4.59 (m, 1H), 5.04 (s, 2H), 5.39 (m, 1H), 6.38 (bs, 2H), 6.42 (d, 1H, J=7 Hz), 6.60 (s, 1H), 6.67 (d, 1H, J=7 Hz), 7.30 (m, 5H). MS: 346 m/z (M+H)$^+$.

Example 133
Synthesis of Intermediate 18.

N-(Benzyloxycarbonyl)-3-(3,4-ethylenedioxyphenyl)-L-alanine methyl ester

A suspension of 13.40 g (38.8 mmol) of compound 17 and 53.66 g (388 mmol) of K$_2$CO$_3$ in. 200 ml of acetone was refluxed under N$_2$ for 30 minutes. Dibromoethane (13.37 ml, 77.6 mmol) was added in one portion. The suspension was refluxed for 40 hours, the solid was filtered, and the filtrate was evaporated. The residue after evaporation was diluted with 150 ml of water and extracted with CH$_2$Cl$_2$ (3×70 ml). The CH$_2$Cl$_2$ extracts were washed with brine and dried over MgSO$_4$ and concentrated. The crude product was washed with small amount of ether to give 12.26 g (85%) of white solid; NMR (CDCl$_3$) δ 3.01 (d, 2H, J=5.2 Hz), 3.73 (s, 3H), 4.22 (s, 4H), 6.52 (d, 1H, J=7 Hz), 6.60 (s, 1H), 6.75 (d, 1H, J=7 Hz), 7.34 (m, 5H). MS: 372 m/z (M+H)$^+$. Anal. Calc'd for C$_{20}$H$_{21}$NO$_6$.0.2H$_2$O: Calc'd: C, 64.00; H, 5.80; N, 3.73; Found: C, 63.83; H, 5.70; N, 3.63.

Example 134
Synthesis of Intermediate 19.

Methyl 3,4-Dihydro-6,7-ethylenedioxy-2H-1,2-benzothiazine-3-carboxylate 1,1-dioxide A solution of 14.82 g (40 mmol) of compound 18 in 150 ml of dried $CHCl_3$ was stirred with mechanic stirrer at 0° C. as 13.32 ml (5.0 eq) of chlorosulfonic acid in 100 ml of $CHCl_3$ was added dropwise via addition funnel over ~1.0 hour. The solution was first turned to yellow, then some thick oil formed and became suspended in the solution. After addition, the reaction mixture was stirred at room temperature and LC-MS was used to follow the reaction. At 3 hours, no starting material was left in the reaction. The reaction was cooled to ~5° C. and 43 ml (10 eq) of $Et_3N$, 733 mg (0.3 eq) of DMAP in $CHCl_3$ (50 ml) was added. The mixture was stirred overnight (~14 hr) while the temperature was warmed to room temperature and then the reaction mixture was refluxed for 3 hours. After that, the reaction mixture was poured into 500 ml of ice-water and separated. The aqueous layer was extracted with $CH_2Cl_2$ (3×100 ml). The combined organic layers were washed with water, 3% HCl, 5% of $NaHCO_3$, brine and dried. The crude product was dissolved in $CH_2Cl_2$ and filtered through a short silica column eluted with 80% of EtOAc in hexane to remove remaining $Et_3N.HCl$ salt. Evaporation solvent afforded 3.0 g (25%) of a white solid; NMR ($CDCl_3$) δ 3.20 (abd, 2H, J=5.1 Hz, 16 Hz), 3.82 (s, 3H), 4.33 (s, 4H), 4.60 (m, 1H), 4.99 (d, 1H, J=8 Hz), 6.77 (s, 1H), 7.39 (s, 1H). MS: 300 m/z $(M+H)^+$. Anal. Calc'd for $C_{12}H_{13}NO_6.S$: Calc'd: C, 48.16; H, 4.38; N, 4.68; Found: C, 48.09; H, 4.66; N, 5.10.

Example 135
Synthesis of Intermediate 20.

Methyl 3,4-Dihydro-6,7-ethylenedioxy-2-ethyl-2H-1,2-benzothiazine-3-carboxylate 1,1-dioxide A solution of 317 mg (1.06 mmol) of compound 19 and 513 mg (3.5 eq) of $K_2CO_3$ in 2.0 ml of DMF was stirred under $N_2$ as 339 ul (4.0 eq) of EtI was added at room temperature. After 14 hours (overnight) at room temperature, the mixture was diluted with $CH_2Cl_2$ (20 ml). The solid was filtered and washed with $CH_2Cl_2$. The filtrates were washed with water, 3% citric acid, 5% of $NaHCO_3$, brine and dried. Evaporation of the solvent afforded 313 mg (90% yield) of a pure white solid; NMR ($CDCl_3$) δ 1.09 (t, 3H, J=7.1 Hz), 3.01–3.4 (m, 6H), 3.79 (s, 3H), 4.25 (s, 4H), 4.15 (1H, dd, J=6 Hz, 11 Hz), 6.74 (s, 1H), 7.28 (s, 1H). MS: 328 m/z $(M+H)^+$. Anal. Calc'd for $C_{14}H_{17}NO_6.S$: Calc'd: C, 51.37; H, 5.23; N, 4.28; Found: C, 51.26; H, 5.08; N, 4.30.

Example 136
Synthesis of Intermediate 21a ($R^4$=H; $R^6$=$R^7$=Cl; Y=$NCH_3$; R=$CH_3$)

Methyl 6,7-dichloro-2-methyl-2H-1,2-benzothiazine-3-carboxylate 1,1-dioxide

To a solution 9 1 (256 mg, 0.79 mmol) in $CCl_4$—$CH_2Cl_2$ (25 ml–5 ml) was added NBS (155 mg, 0.87 mmol) and dibenzoylperoxide (38 mg, 0.16 mmol). The mixture was refluxed in the dark for one hour, at which time tlc analysis showed complete consumption of starting material. After being cooled to ambient temperature, dichloromethane was added and the mixture was washed with 10% sodium thiosulfate, water, brine, dried over anhydrous magnesium sulfate, filtered and concentrated to give 250 mg of the title compound, subsequently used without further purification; NMR ($CDCl_3$) δ 3.18 (s, 3H), 3.87 (s, 3H), 7.43 (s, 1H), 7.59 (s, 1H), 7.87 (s, 1H).

Example 137
Synthesis of Intermediate 21b ($R^6$+$R^7$=$OCH_2CH_2O$; $R^1$=H; Y=NMe; R=$CH_3$)

Methyl 6,7-ethylenedioxy-2-methyl-2H-1,2-benzothiazine-3-carboxylate 1,1-dioxide This compound was prepared according to the procedure above for 21a. From 9r (R=$CH_3$; 150 mg, 0.48 mmol) the title compound (100 mg, 66%) was obtained following flash chromatography on silica gel (30% ethyl acetate/hexanes); MS: 312 $(M+H)^+$.

Example 138
Synthesis of Intermediate 21d (R=Me; $R^4$=OMe; $R^6$=$R^7$=H; Y=NMe)

Methyl 2-methyl-4-methoxy-2H-1,2-benzothiazine-3-carboxylate

This compound was prepared according to Zinnes et. al., J. Med. Chem., 1973, 16, 44–48. Thus, a solution of methyl 2-methyl-4-hydroxy-2H-1,2-benzothiazine-3-carboxylate (500 mg, 1.86 mmol) (Lombardino, et. al., J. Med. Chem., 1971, 14, 1171–1177, incorporated by reference herein in its entirety) in acetone (10 ml) was treated with anhydrous potassium carbonate (2.6 g, 18.6 mmol) and iodomethane (1.32 g, 9.29 mmol) and refluxed for 40 hours. The mixture was filtered and concentrated and the residue was partitioned between ethyl acetate and water. The organic phase was washed with saturated aqueous sodium bicarbonate and brine, dried over anhydrous magnesium sulfate, filtered and concentrated to afford 285 mg (54%) of the title compound as a yellow viscous oil, used subsequently without need for further purification; NMR ($CDCl_3$) δ 3.03 (s, 3H), 3.83 (s, 3H), 3.91 (s, 3H), 7.67–7.72 (m, 2H), 7.81–7.88 (m, 2H); MS: 284 m/z $(M+H)^+$.

Example 139
Synthesis of Intermediate 23a ($R^4$=H; $R^6$=$R^7$=Cl; Y=$NCH_3$)

6,7-Dichloro-2-methyl-2H-1,2-benzothiazine-3-carboxylic acid 1,1-dioxide

To a solution of 21a (250 mg, 0.77 mmol) in MeOH (10 ml) and DMF (3 ml, to aid solubility) was added 5N NaOH (25 ml). The mixture was warmed to ~50° C. while being stirred for 20 minutes, at which time tlc analysis showed complete consumption of starting material. The mixture was cooled to ambient temperature, the MeOH was stripped on the rotary evaporator, the residue was diluted with water (25 ml) and clarified by filtration. Adjustment to pH 2 gave a precipitate which was collected by suction filtration, washed with water and allowed to air-dried overnight to afford 128 mg (54% overall from 9a) of the title compound; MS: 306, 308, 310 m/z $(M-H)^-$, $Cl_2$ pattern.

Example 140
Synthesis of Intermediate 23d ($R^4$=OMe; $R^6$=$R^7$=H; Y=NMe) 2-Methyl-4-methoxy-2H-1,2-benzothiazine-3-carboxylic acid 1,1-dioxide A solution of 21d (159 mg, 0.56 mmol) in methanol (3 ml) was treated with 5N NaOH (2 ml) and stirred at room temperature for 20 minutes, at which time tlc analysis showed complete consumption of starting material. The methanol was removed on the rotary evaporator and the aqueous residue was adjusted to pH 3 with 4N HCl. The precipitate so formed was collected by suction filtration, washed with water and allowed to air-dry to constant weight to give 94 mg (62%) of the title compound as a white solid; MS: 292 m/z $(M+Na)^+$; Anal. Calc'd for $C_{11}H_{11}NO_5S$: C, 49.07; H, 4.13; N, 5.20; S, 11.89; Found: C, 48.84; H, 3.85; N, 4.98; S, 11.78.

Example 141
Synthesis of Intermediate 25a ($R^4$=H; $R^6$=$R^7$=Cl; $R^1$=Bn; Y=$NCH_3$; Q=H)

N-(6,7-Dichloro-2-methyl-2H-1,2-benzothiazine-3-carbonyl)-L-phenylalaninol 1,1-dioxide This compound was prepared according to General Procedure G. From 23a (100 mg, 0.32 mmol) the title compound (137 mg) was obtained following flash chromatography on silica gel (50% ethyl acetate/hexanes); MS: 441, 443, 445 m/z (M+H)$^+$, Cl$_2$ pattern.

Example 142

Synthesis of Intermediate 25b ($R^4$=H; $R^6$+$R^7$=OCH$_2$CH$_2$O; $R^1$=Bn; Y=NCH$_3$; Q=H)

N-(6,7-Ethylenedioxy-2-methyl-2H-1,2-benzothiazine-3-carbonyl)-L-phenylalaninol 1,1-dioxide This compound was prepared according to General Procedure G. From 23b (80 mg, 0.27 mmol) the title compound (96 mg, 83%) was obtained following flash chromatography on silica gel (50% ethyl acetate/hexanes); MS: 431 m/z (M+H)$^+$.

Example 143

Synthesis of Intermediate 25c ($R^4$=H; $R^6$+$R^7$=OCH$_2$CH$_2$O; $R^1$=Bn; Y=NEt; Q=H)

N-(6,7-Ethylenedioxy-2-ethyl-2H-1,2-benzothiazine-3-carbonyl)-L-phenylalaninol 1,1-dioxide This compound was prepared according to General Procedure G. From 23c (100 mg, 0.32 mmol) the title compound (136 mg, 95%) was obtained following flash chromatography on silica gel (50% ethyl acetate/hexanes); MS: 445 m/z (M+H)$^+$.

Example 144

Synthesis of Intermediate 25d ($R^4$=OMe; $R^6$=$R^7$=H; $R^1$=Bn; Y=NMe; Q=H)

N-(2-Methyl-4-methoxy-2H-1,2-benzothiazine-3-carbonyl)-L-phenylalaninol 1,1-dioxide This compound was prepared according to General Procedure G. From 23d (22 mg, 0.08 mmol) the title compound (32 mg, 99%) was obtained; MS: 403 m/z (M+H)$^+$.

Example 145

Synthesis of Intermediate 25e ($R^4$=H; $R^6$+$R^7$=OCH$_2$CH$_2$O; $R^1$=Bn; Y=NMe; Q=CONHBu)

3-((6,7-Ethylenedioxy-2-methyl-2H-1,2-benzothiazine-3-carbonyl)amino)-3-(S)-benzyl-2-(R,S)-hydroxy-N-butylpropanamide 1,1-dioxide This compound was prepared according to General Procedure K. From 26b (55 mg, 0.13 mmol) the title compound (22 mg, 32%) was obtained following flash chromatography on silica gel (ethyl acetate); MS: 530 m/z (M+H)$^+$.

Example 146

Synthesis of Intermediate 25f ($R^4$=H; $R^6$+$R^7$=OCH$_2$CH$_2$O; $R^1$=Bn; Y=NEt; Q=CONHBu)

3-((6,7-Ethylenedioxy-2-methyl-2H-1,2-benzothiazine-3-carbonyl)amino)-3-(S)-benzyl-2-(R,S)-hydroxy-N-butylpropanamide 1,1-dioxide This compound was prepared according to General Procedure K. From 26c (80 mg, 0.18 mmol) the title compound (30 mg, 31%) was obtained following preparative tlc on silica gel (ethyl acetate); MS: 542 m/z (M–H)$^-$.

Example 147

Synthesis of Intermediate 25g ($R^4$=OMe; $R^6$=$R^7$=H; $R^1$=Bn; Y=NMe; Q=CONHBu)

3-((4-Methoxy-2-methyl-2H-1,2-benzothiazine-3-carbonyl)amino)-3-(S)-benzyl-2-(R,S)-hydroxy-N-butylpropanamide 1,1-dioxide This compound was prepared according to General Procedure G. From 23d (50 mg, 0.18 mmoL) the title compound (80 mg, 83%) was obtained following flash chromatography on silica gel (65% ethyl acetate/hexanes); MS: 502 m/z (M+H)$^+$.

Example 148

Synthesis of Intermediate 25h ($R^4$=OH; $R^6$=$R^7$=H; $R^1$=Bn; Y=NMe; Q=CONHBu)

3-((4-Hydroxy-2-methyl-2H-1,2-benzothiazine-3-carbonyl)amino)-3-(S)-benzyl-2-(R,S)-hydroxy-N-butylpropanamide 1,1-dioxide This compound was prepared according to the method of Lombardino et. al., *J. Med. Chem.*, 1973, 16, 493–496, incorporated by reference herein in its entirety. Thus, a slurry of methyl 2-methyl-4-hydroxy-2H-1,2-benzothiazine-3-carboxylate (54 mg, 0.20 mmol) and 3-amino-3-(S)-benzyl-2-(R,S)-hydroxy-N-butylpropanamide (50 mg, 0.20 mmol) in xylenes (5 ml) was refluxed for 18 hours. The mixture was concentrated on a vacuum line, the residue was partitioned between ethyl acetate and water, the organic phase was washed with 5% aqueous citric acid solution, water and brine, dried over anhydrous magnesium sulfate, filtered and concentrated to give 104 mg crude product, further purified by flash chromatography on silica gel (50% ethyl acetate/hexanes) to give 59 mg (60%) of the title compound as an off-white solid; MS: 488 m/z (M+H)$^+$.

Example 149

Synthesis of Aldehyde 26a ($R^4$=H; $R^6$=$R^7$=Cl; $R^1$=Bn; Y=NCH$_3$; Q=H)

N-(6,7-Dichloro-2-methyl-2H-1,2-benzothiazine-3-carbonyl)-L-phenylalaninal 1,1-dioxide This compound was prepared according to General Procedure I. From 25a (Q=H, 50 mg, 0.11 mmol) the title compound (942 mg, 84%) was obtained as an off-white solid; MS: 437, 439, 441 (M–H)$^-$; Cl$_2$ pattern.

Example 150

Synthesis of Aldehyde 26b ($R^4$=H; $R^6$+$R^7$=OCH$_2$CH$_2$O; $R^1$=Bn; Y=NCH$_3$; Q=H)

N-(6,7-Ethylenedioxy-2-methyl-2H-1,2-benzothiazine-3-carbonyl)-L-phenylalaninal 1,1-dioxide This compound was prepared according to General Procedure I. From 25b (Q=H, 52 mg, 0.12 mmol) the title compound (41 mg, 79%) was obtained as a white solid; MS: 429 (M+H)$^+$.

Example 151

Synthesis of Aldehyde 26c ($R^4$=H; $R^6$+$R^7$=OCH$_2$CH$_2$O; $R^1$=Bn; Y=NEt; Q=H)

N-(6,7-Ethylenedioxy-2-ethyl-2H-1,2-benzothiazine-3-carbonyl)-L-phenylalaninal 1,1-dioxide This compound was prepared according to General Procedure I. From 25c (Q=H, 135 mg, 0.30 mmol) the title compound (109 mg, 81%) was obtained as a pale yellow solid; MS: 441 (M–H)$^-$.

Example 152

Synthesis of Aldehyde 26d ($R^4$=OMe; $R^6$=$R^7$=H; $R^1$=Bn; Y=NMe; Q=H)

N-(2-Methyl-4-methoxy-2H-1,2-benzothiazine-3-carbonyl)-L-phenylalaninal 1,1-dioxide This compound was prepared according to General Procedure I. From 25d (Q=H, 32 mg, 0.08 mmol) the title compound (25 mg, 76%) was obtained; MS: 401 m/z (M+H)$^+$.

Example 153

Synthesis of Ketoamide 27e ($R^4$=H; $R^6$+$R^7$=OCH$_2$CH$_2$O; $R^1$=Bn; Y=NMe; Q=CONHBu)

3-((6,7-Ethylenedioxy-2-methyl-2H-1,2-benzothiazine-3-carbonyl)amino)-3-(S)-benzyl-2-oxo-N-butylpropanamide 1,1-dioxide This compound was prepared according to General Procedure I. From 25e (Q=CONHBu, 20 mg, 0.04 mmol) the title compound (15 mg, 75%) was obtained as a white solid; MS: 528 m/z (M+H)$^+$.

Example 154
Synthesis of Ketoamide 27f (R$^1$=H; R$^6$+R$^7$=OCH$_2$CH$_2$O; R$^1$=Bn; Y=NEt; Q=CONHBu)

3-((6,7-Ethylenedioxy-2-methyl-2H-1,2-benzothiazine-3-carbonyl)amino)-3-(S)-benzyl-2-oxo-N-butylpropanamide 1,1-dioxide This compound was prepared according to General Procedure I. From 25f (Q=CONHBu, 24 mg, 0.04 mmol) the title compound (22 mg, 92%) was obtained as a white solid; MS: 542 m/z (M+H)$^+$.

Example 155
Synthesis of Ketoamide 27g (R$^4$=OMe; R$^6$=R$^7$=H; R$^1$=Bn; Y=NMe; Q=CONHBu)

3-((4-Methoxy-2-methyl-2H-1,2-benzothiazine-3-carbonyl)amino)-3-(S)-benzyl-2-oxo-N-butylpropanamide 1,1-dioxide This compound was prepared according to General Procedure I. From 25g (Q=CONHBu, 60 mg, 0.12 mmol) the title compound (49 mg, 82%) was obtained as a white solid; MS: 500 m/z (M+H)$^+$.

Example 156
Synthesis of Ketoamide 27h (R$^4$=OH; R$^6$=R$^7$=H; R$^1$=Bn; Y=NMe; Q=CONHBu)

3-((4-Hydroxy-2-methyl-2H-1,2-benzothiazine-3-carbonyl)amino)-3-(S)-benzyl-2-oxo-N-butylpropanamide 1,1-dioxide This compound was prepared according to General Procedure I. From 25h (Q=CONHBu, 42 mg, 0.09 mmol) the title compound (18 mg, 43%) was obtained following preparative tlc on silica gel (50% ethyl acetate/hexanes); MS: 486 m/z (M+H)$^+$; Anal. Calc'd for C$_{24}$H$_{27}$N$_3$O$_6$S: C, 59.36; H, 5.62; N, 8.66; S, 6.59; Found: C, 59.56; H, 5.76; N, 7.97; S, 6.71.

Example 157
Synthesis of Intermediate 31a (R$^4$=Pr; R$^6$=R$^7$=H)

3,4-Dihydro-4-propyl-2H-1,2,4-benzothiadiazine-3-carboxylic acid 1,1-dioxide

This compound was prepared according to the method of Close et. al., *J. Org. Chem.*, 1961, 26, 3423–3433, incorporated by reference herein in its entirety. Thus, a solution of methyl dimethoxyacetate (3.6 g, 27.3 mmol) in water (50 l) was refluxed for 2.5 hours. A stillhead was attached and the methanol so generated was allowed to distill off (a total of 10 ml of liquid was collected, of which 5 ml was replenished with water). To the hot solution was added 2-(propylamino) benzenesulfonamide (4.5 g, 21.0 mmol) (prepared according to the procedure of Biressi et. al., *Farmeco. Ed. Sci.* (It.), 1969, 24, 199–220, incorporated by reference herein in its entirety) and 1,4-dioxane (5 ml, to give a homogeneous solution) and reflux was continued for 1.5 hours. The mixture was adjusted to pH 3 (2N NaOH), extracted with ethyl acetate and the organic phase was washed with brine, dried over anhydrous magnesium sulfate, filtered and concentrated to give 4.8 g crude product which was recrystallized (ethyl acetate/hexanes) to give 2.5 g (44%) of the title compound as a white solid; NMR (DMSO-d$_6$) δ 0.85 (t, J=7 Hz, 3H), 1.47–1.57 (m, 2H), 2.94–3.04 (m, 1H), 3.38 (br, 1H), 3.40–3.46 (m, 1H), 5.27 (d, J=6 Hz, 1H), 6.70 (t, J=7 Hz, 1H), 6.84 (d, J=7 Hz, 1H), 7.36 (t, J=7 Hz), 7.43 (d, J=7 Hz, 1H), 8.44 (d, J=7 Hz, 1H), 13.04 (br, 1H); MS: 269 m/z (M–H)$^-$; Anal. Calc'd for C$_{11}$H$_{14}$N$_2$O$_4$S: C, 48.88; H, 5.23; N, 10.37; S, 11.84; Found: C, 49.17; H, 5.21; N, 10.27; S, 11.54.

Example 158
Synthesis of Intermediate 34a (R$^4$=Pr; R$^6$=R$^7$=H; R$^1$=Bn; Y=NEt; Q=H)

N-(3,4-Dihydro-2-ethyl-4-propyl-2H-1,2,4-benzothiadiazine-3-carbonyl)-L-phenylalaninol 1,1-dioxide This compound was prepared according to General Procedure G. From 33a (300 mg, 1.0 mmol) crude product (508 mg) was obtained as a mixture of diastereomers which were partially separated by flash chromatography on silica gel (50% ethyl acetate/hexanes):

Isomer 1: 95 mg (21%); MS: 432 m/z (M+H)$^+$;
Isomer 2: 83 mg (20%); MS: 432 m/z (M+H)$^+$.
Also isolated was 118 mg (27%) of a diastereomeric mixture.

Example 159
Synthesis of Intermediate 34c (R$^4$=Bn; R$^6$=R$^7$=H; R$^1$=Bn; Y=NEt; Q=H)

N-(3,4-Dihydro-2-ethyl-4-benzyl-2H-1,2,4-benzothiadiazine-3-carbonyl)-L-phenylalaninol 1,1-dioxide This compound was prepared according to General Procedure G. From 33c (65 mg, 0.19 mmol) crude product (100 mg) was obtained as a mixture of diastereomers which were separated by preparative tlc on silica gel (50% ethyl acetate/hexanes):

Isomer 1: 24 mg (27%); MS: 480 m/z (M+H)$^+$;
Isomer 2: 40 mg (44%); MS: 480 m/z (M+H)$^+$.

Example 160
Synthesis of Aldehyde 35a (R$^4$=Pr; R$^6$=R$^7$=H; R$^1$=Bn; Y=NEt; Q=H)

N-(3,4-Dihydro-2-ethyl-4-propyl-2H-1,2,4-benzothiadiazine-3-carbonyl)-L-phenylalaninal 1,1-dioxide This compound was prepared according to General Procedure I. From 34a (isomer 1; 95 mg, 0.22 mol) the title compound (94 mg, 99%) was obtained; MS: 430 m/z (M+H)$^+$.

Example 161
Synthesis of Aldehyde 35b (R$^4$=Pr; R$^6$=R$^7$=H; R$^1$=Bn; Y=NEt; Q=H)

N-(3,4-Dihydro-2-ethyl-4-propyl-2H-1,2,4-benzothiadiazine-3-carbonyl)-L-phenylalaninal 1,1-dioxide This compound was prepared according to General Procedure I. From 34a (isomer 2; 83 mg, 0.19 mol) the title compound (42 mg, 51%) was obtained; MS:; 430 m/z (M+H)$^+$.

Example 162
Synthesis of Aldehyde 35c (R$^4$=Bn; R$^6$=R$^7$=H; R$^1$=Bn; Y=NEt; Q=H)

N-(3,4-Dihydro-2-ethyl-4-benzyl-2H-1,2,4-benzothiadiazine-3-carbonyl)-L-phenylalaninal 1,1-dioxide This compound was prepared according to General Procedure I. From 34c (isomer 1; 22 mg, 0.05 mol) the title compound (21 mg, 95%) was obtained; MS: 478 m/z (M–H)$^-$.

Example 163
Synthesis of Aldehyde 35d (R$^4$=Bn; R$^6$=R$^7$=H; R$^1$=Bn; Y=NEt; Q=H)

N-(3,4-Dihydro-2-ethyl-4-benzyl-2H-1,2,4-benzothiadiazine-3-carbonyl)-L-phenylalaninal 1,1-dioxide This compound was prepared according to General Procedure I. From 34c (isomer 2; 35 mg, 0.07 mol) the title compound (33 mg, 94%) was obtained; MS: 478 m/z $(M+H)^+$; Anal. Calc'd for $C_{26}H_{27}N_3O_4S \cdot H_2O$: C, 63.01; H, 5.91; N, 8.48; S, 6.45; Found: C, 63.03; H, 5.52; N, 7.86; S, 5.79.

Example 164

Synthesis of Ketoamide 35e ($R^4$=H; $R^6$=$R^7$=H; $R^1$=Bn; Y=NMe; Q=CONHBu)

3-((3,4-Dihydro-4H-2-methyl-2H-1,2,4-benzothiadiazine-3-carbonyl)amino)-3-(S)-benzyl-2-oxo-N-butylpropanamide 1,1-dioxide This compound was prepared according to General Procedure I in which isobutyl chloroformate was used in place of HOBt/BOP. From 33e (40 mg, 0.17 mmol) and 3-amino-3-(S)-benzyl-2-oxo-N-butylpropanamide hydrochloride (56 mg, 0.20 mmol) the title compound (46 mg, 97%) was obtained as a pale yellow solid; MS: 471 m/z $(M-H)^-$.

Example 165

Synthesis of Intermediate 36b ($R^6$+$R^7$=$OCH_2CH_2O$)

6,7-Ethylenedioxy-2H-1,2,4-benzothiadiazin-3-(4H)-one 1,1-dioxide

This compound was prepared according to the method of Girard et. al., *J. Chem. Soc.*, Perkin I; 1979, 1043–1047, incorporated by reference herein in its entirety. To a solution of chlorosulfonyl isocyanate (5.6 g, 40.0 mmol) in nitroethane (35 ml) at −40° C. was added dropwise over five minutes a solution of 1,4-benzodioxan-6-amine (5.0 g, 33.1 mmol) in nitroethane (5 ml). The mixture was allowed to warm to 0° C. and stirred for one hour at which time anhydrous aluminum chloride was added. The mixture was warmed to 110° C. and stirred for 30 minutes (copious HCl evolution) and allowed to cool to ambient temperature before being added dropwise to a vigorously stirred ice-water (~150 g) mixture. The resulting precipitate was collected by suction filtration, washed with water and air-dried to give 4.4 g (52%) of the title compound as a light gray powder; MS: 255 m/z $(M-H)^-$.

Example 166

Synthesis of Intermediate 37b ($R^6$+$R^7$=$OCH_2CH_2O$)

4,5-Ethylenedioxy-2-sulfanilamide hydrochloride

A mixture of 36b (1.0 g, 3.0 mmol) in concentrated hydrochloric acid (40 ml) was stirred while being refluxed for 18 hours. The mixture was clarified by filtration and concentrated in vacuo. The residue was triturated with ether to give 1.0 g (96%) of the title compound as a tan solid; MS: 231 m/z $(M+H-HCl)^+$.

Example 167

Synthesis of Intermediate 38a ($R^6$=$R^7$=H)

Ethyl 2-(Oxalylamino)benzenesulfonamide

To a solution of o-sulfanilamide (10.5 g, 61 mmol) in THF chilled in an ice-water bath was added triethylamine (8.9 ml, 64 mmol) followed by slow dropwise addition of ethyl oxalylchloride (7.2 ml, 64 mmol) over 5–10 minutes. The mixture was allowed to slowly warm to ambient temperature over five hours. The precipitate was removed by filtration and the concentrated filtrate was recrystallized (ethyl acetate) to give 9.0 g (54%) of the title compound; MS: 273 m/z $(M+H)^+$; Anal. Calc'd for $C_{10}H_{12}N_2O_5S$: C, 44.12; H, 4.45; N, 10.29; S, 11.75; Found: C, 44.21; H, 4.13; N, 10.08; S, 11.75.

Example 168

Synthesis of Intermediate 38b ($R^6$+$R^7$=$OCH_2CH_2O$)

Ethyl 4,5-ethylenedioxy-2-(oxalylamino)benzenesulfonamide

This compound was prepared using the procedure described for compound 38a. From compound 37b (1.0 g, 3.75 mmol) there was obtained 385 mg (31%) of the title compound following recrystallization (EtOAc); MS: 329 m/z $(M-H)^-$.

Example 169

Synthesis of Intermediate 39a ($R^6$=$R^7$=H)

Ethyl 2H-1,2,4-benzothiadiazine-3-carboxylate 1,1-dioxide

To a flask containing anhydrous ethanol (25 ml) was added NaH (60% suspension in mineral oil; 155 mg, 4.0 mmol). The mixture was stirred for 15 minutes and 38a (1.0 g, 3.7 mmol) was added in one portion. The mixture was stirred for two hours at which time tlc analysis showed complete consumption of starting material. Water (50 ml) was added, the pH was adjusted to 3–4 (4N HCl), and the ethanol was removed on the rotary evaporator. The precipitate was collected by suction filtration, washed with water and dried to constant weight to afford 0.66 g (71%) of the title compound; MS: 273 m/z $(M+H)^+$.

Example 170

Synthesis of Intermediate 39b ($R^6$+$R^7$=$OCH_2CH_2O$)

Ethyl 2H-6,7-ethylenedioxy-1,2,4-benzothiadiazine-3-carboxylate 1,1-dioxide

This compound was prepared using the procedure described for compound 39a. From compound 38b (330 mg, 1.0 mmol) there was obtained 173 mg (55%) of the title compound as a tan powder; MS: 311 m/z $(M-H)^-$.

Example 171

Synthesis of Intermediate 40b ($R^6$+$R^7$=$OCH_2CH_2O$)

2H-6,7-Ethylenedioxy-1,2,4-benzothiadiazine-3-carboxylic acid 1,1-dioxide

This compound was prepared using the procedure described for compound 40a. From compound 39b (170 mg, 0.54 mmol) there was obtained 100 mg (65%) of the title compound as an off-white solid; MS: 283 m/z $(M-H)^-$.

Example 172

Synthesis of Intermediate 41b ($R^6$+$R^7$=$OCH_2CH_2O$; $R^1$=Bn; Q=H)

N-(2H-6,7-Ethylenedioxy-1,2,4-benzothiadiazine-3-carbonyl)-L-phenylalaninol 1,1-dioxide This compound was prepared according to General Procedure G. From compound 40b (50 mg, 0.18 mol) there was obtained 23 mg (32%) of the title compound as a pale yellow solid; MS: 440 m/z $(M+Na)^+$.

Example 173

Synthesis of Aldehyde 42a ($R^6$=$R^7$=H; $R^1$=Bn; Y=NH; Q=H)

N-(2H-1,2,4-Benzothiadiazine-3-carbonyl)-L-phenylalaninal 1,1-dioxide

This compound was prepared (following hydrolysis of 39a) according to General Procedures G and I. From 41a (43 mg, 0.12 mol) the title compound (14 mg, 33%) was obtained; MS: 358 m/z $(M+H)^+$.

Example 174

Synthesis of Aldehyde 42b ($R^6$+$R^7$=$OCH_2CH_2O$; $R^1$=Bn; Y=NH; Q=H)

N-(2H-6,7-Ethylenedioxy-1,2,4-benzothiadiazine-3-carbonyl)-L-phenylalaninal 1,1-dioxide This compound was prepared according to General Procedure I. From compound 41b (23 mg, 0.06 mol) there was obtained 22 mg (96%) of the title compound as an off-white solid; MS: 416 m/z (M+H)+.

Example 175
Synthesis of Ketoamide 42c ($R^6=R^7=H$; $R^1=Bn$; Y=NH; Q=CONHBu)

3-((2H-1,2,4-Benzothiadiazine-3-carbonyl)amino)-3-(S)-benzyl-2-oxo-N-butylpropanamide 1,1-dioxide This compound was prepared according to General Procedure I (in this case, isobutyl chloroformate was used in place of HOBt/BOP). From compound 40a (25 mg, 0.11 mmol) and 3-amino-3-(S)-benzyl-2-oxo-N-butylpropanamide hydrochloride (35 mg, 0.12 mmol) the title compound (9 mg, 18%) was obtained as an off-white solid following trituration of the crude (33 mg) product with ether; MS: 455 m/z (M-H)−.

Example 176
Synthesis of Ketoamide 42d ($R^6+R^7=OCH_2CH_2O$; $R^1=Bn$; Y=NH; Q=CONHBu)

3-((2H-6,7-Ethylenedioxy-1,2,4-benzothiadiazine-3-carbonyl)amino)-3-(S)-benzyl-2-oxo-N-butylpropanamide 1,1-dioxide This compound was prepared according to General Procedure I (in which isobutyl chloroformate was used in place of HOBt/BOP. From compound 40b (40 mg, 0.14 mmol) and 3-amino-3-(S)-benzyl-2-oxo-N-butylpropanamide hydrochloride (48 mg, 0.17 mmol) the title compound (9 mg, 13%) was obtained as an off-white solid following recrystallization (ethyl acetate/hexanes); MS: 513 m/z (M-H)−.

Example 177
Synthesis of Intermediate 44 ($R^6=R^7=H$)

N-Benzoyl-1,2,3,4-tetrahydro-3-isoquinolinecarboxylic acid

This compound was prepared according to Hein et. al., *J. Amer. Chem. Soc.*; 1962, 84, 4487–4494, incorporated by reference herein in its entirety. Thus, a slurry of 1,2,3,4-tetrahydro-3-isoquinolinecarboxylic acid hydrochloride (20.3 g, 95 mmol) in 2N NaOH (150 ml) was treated with benzoyl chloride (13.4 ml, 114 mmol) dropwise over 30 minutes. The mixture was stirred a further 1.5 hours, acidified to pH 2–3 (4N HCl), and extracted with ethyl acetate. The organic phase was washed with water and brine, dried over anhydrous magnesium sulfate, filtered and concentrated to afford 16.4 g (61) of the title compound following recrystallization (acetone/water); MS: 280 m/z (M-H)−.

Example 178
Synthesis of Intermediate 45 ($R^6=R^7=H$)

N-Benzoyl-2-carboxyphenylalanine

This compound was prepared according to Maeda et. al., *Chem. Pharm. Bull.*; 1988, 36, 190–201, incorporated by reference herein in its entirety. A solution of compound 44 (15.4 g, 54.7 mmol) and potassium carbonate (7.6 g, 54.7 mmol) in water (450 ml) was treated portionwise with potassium permanganate (17.3 g, 109.5 mmol) over 10 minutes. The mixture was stirred for two hours, quenched with sodium bisulfite (6.5 g) and stirred for 5–10 minutes, and filtered through a bed of Celite®. The filtrate was acidified to pH 2–3 and the resulting gummy precipitate was extracted with ethyl acetate. The organic phase was washed with water and brine, dried over anhydrous magnesium sulfate, filtered and concentrated to afford 10.0 g (58%) of the title compound as a white solid; MS: 312 m/z (M-H)−.

Example 179
Synthesis of Intermediate 46 ($R^6=R^7=H$)

1-oxo-1,2,3,4-tetrahydroisoquinoline-3-carboxylic acid

A slurry of compound 45 (6.4 g, 20.4 mmol) in 6N HCl (250 ml) was stirred while being refluxed for 18 hours. The resulting homogeneous solution was allowed to cool to ambient temperature to give a precipitate which was collected by suction filtration, washed with water and air-dried to afford 3.05 (78%) of the title compound; NMR (CDCl$_3$—CD$_3$OD) δ 3.01–3.31 (m, 2H), 4.29 (m, 1H), 7.18–7.41 (m, 3H) 7.94 (t, J=8 Hz, 1H); MS: 190 m/z (M-H)−.

Example 180
Synthesis of Intermediate 47 ($R^6=R^7=H$)

2-Methyl-1-oxo-1,2,3,4-tetrahydroisoquinoline-3-carboxylic acid

A solution of compound 46 (1.5 g, 7.8 mmol) in DMF (70 ml) was treated with iodomethane (9.7 ml, 157 mmol) and silver(I) oxide (5.5 g, 23.5 mmol) and stirred in the dark for seven days. The mixture was filtered through Celite®, the DMF was removed in vacuo and the residue was partitioned between ethyl acetate and water. The organic phase was washed with 10% aqueous sodium thiosulfate, water and brine, dried over anhydrous magnesium sulfate, filtered and concentrated to give 0.96 g (56%) of methyl 2-methyl-1-oxo-1,2,3,4-tetrahydroisoquinoline-3-carboxylate following flash chromatography on silica gel (30% ethyl acetate/hexanes); NMR (CDCl$_3$) δ 3.17 (s, 3H), 3.23–3.50 (m, 2H), 3.61 (s, 3H), 4.21 (m, 1H), 7.12 (d, J=7 Hz, 1H), 7.32–7.38 (m, 2H), 8.06 (d, J=7 Hz, 1H).

This compound was saponified according to the procedure for 23a. From methyl 2-methyl-1-oxo-1,2,3,4-tetrahydroisoquinoline-3-carboxylate (0.95 g, 4.3 mmol) the title compound (0.66 g, 74%) was obtained; MS: 204 m/z (M-H)−.

Example 181
Synthesis of Intermediate 48 ($R^6=R^7=H$; $R^1=Bn$; Y=NH)

N-(1-Oxo-1,2,3,4-tetrahydroisoquinoline-3-carbonyl)-L-phenylalaninol

This compound was prepared according to General Procedure G. From compound 46 (200 mg, 1.05 mmol) crude product (353 mg) was obtained as a mixture of diastereomers which were partially separated by preparative tlc on silica gel (10% MeOH/CH$_2$Cl$_2$):

Isomer 1: 30 mg (9%); MS: 325 m/z (M+H)+; 50:50 mix by HPLC

Isomer 2: 41 mg (13%); MS: 325 m/z (M+H)+; 92:8 mix by HPLC

Example 182
Synthesis of Intermediate 49c ($R^6=R^7=H$; $R^1=Bn$; Y=NCH$_3$)

N-(1-Oxo-2-methyl-1,2,3,4-tetrahydroisoquinoline-3-carbonyl)-L-phenylalaninol

This compound was prepared according to General Procedure G. From compound 47 (250 mg, 1.22 mmol) crude product (486 mg) was obtained as a mixture of diastereomers which were separated by preparative tlc on silica gel (5% MeOH/CH$_2$Cl$_2$):

Isomer 1: 114 mg (28%); MS: 339 m/z (M+H)+;
Isomer 2: 107 mg (26%); MS: 339 m/z (M+H)+.

Example 183
Synthesis of Aldehyde 50a ($R^6=R^7=H$; $R^1=Bn$; Y=NH)

N-(1-Oxo-1,2,3,4-tetrahydroisoquinoline-3-carbonyl)-L-phenylalaninal

This compound was prepared according to General Procedure I. From compound 48 (isomer 1; 28 mg, 0.09 mol) the title compound (13 mg, 46%) was obtained; MS: 323 m/z (M+H)+.

Example 184
Synthesis of Aldehyde 50b ($R^6=R^7=H$; $R^1=Bn$; Y=NH)

N-(1-Oxo-1,2,3,4-tetrahydroisoquinoline-3-carbonyl)-L-phenylalaninal

This compound was prepared according to General Procedure I. From compound 48 (isomer 2; 37 mg, 0.11 mol) the title compound (22 mg, 59%) was obtained; MS: 323 m/z $(M+H)^+$.

Example 185
Synthesis of Aldehyde 50c ($R^6=R^7=H$; $R^1=Bn$; $Y=NCH_3$)

N-(1-Oxo-2-methyl-1,2,3,4-tetrahydroisoquinoline-3-carbonyl)-L-phenylalaninal

This compound was prepared according to General Procedure I. From compound 49c (isomer 1; 43 mg, 0.13 mol) the title compound (22 mg, 51%) was obtained; MS: 337 m/z $(M+H)^+$.

Example 186
Synthesis of Aldehyde 50d ($R^6=R^7=H$; $R^1=Bn$; $Y=NCH_3$)

N-(1-Oxo-2-methyl-1,2,3,4-tetrahydroisoquinoline-3-carbonyl)-L-phenylalaninal

This compound was prepared according to General Procedure I. From compound 49c (isomer 2; 39 mg, 0.12 mol) the title compound (30 mg, 77%) was obtained; MS: 337 m/z $(M+H)^+$.

Example 187
Synthesis of Bisulfite Addition Product of Aldehyde 12s

N-(3,4-Dihydro-6,7-ethylenedioxy-2-ethyl-2H-1,2-benzothiazine-3-carbonyl)-L-phenylalaninal 1,1-dioxide, bisulfite addition compound To a solution of aldehyde 12s (Example 90) (200 mg, 0.45 mmol) in ethyl acetate (2 ml) was added water (1 ml) and sodium bisulfite (52 mg, 0.49 mmol). The mixture was stirred vigorously for 1.5 hours at ambient temperature. The phases were separated and the organic phase was stirred for several minutes with water (1 ml). The combined aqueous phases were lyophilized to afford 214 mg (87%) of the title compound as a white solid; MS: 525 m/z $(M-Na)^-$. $IC_{50}$ (calpain), 8 nM.

Example 188

Inhibition of Cysteine Protease Activity

To evaluate inhibitory activity, stock solutions (40 times concentrated) of each compound to be tested were prepared in 100% anhydrous DMSO and 5 mL of each inhibitor preparation were aliquoted into each of three wells of a 96-well plate. Calpain I, prepared by a modification of the method of W. J. Lee et al. (*Biochem. Internatl.* 22: 163–171 (1990), incorporated by reference herein in its entirety), was diluted into assay buffer (i.e., 50 mM Tris, 50 mM NaCl, 1 mM EDTA, 1 mM EGTA, and 5 mM-mercaptoethanol, pH 7.5 including 0.2 mM Succ-Leu-Tyr-MNA (Enzyme Systems Products, Dublin, Calif.) and 175 mL aliquoted into the same wells containing the independent inhibitor stocks as well as to positive control wells containing 5 mL DMSO, but no compound. To start the reaction, 20 mL of 50 mM $CaCl_2$ in assay buffer was added to each of the wells of the plate, excepting three, which were used as background signal baseline controls. Substrate hydrolysis was monitored every 5 minutes for a total of 30 minutes using a Fluoroskan II fluorescence plate reader. Substrate hydrolysis in the absence of inhibitor was linear for up to 15 minutes.

Inhibition of calpain I activity was calculated as the percent decrease in the rate of substrate hydrolysis in the presence of inhibitor relative to the rate in its absence. Comparison between the inhibited and control rates was made within the linear range for substrate hydrolysis. For screening, compounds were tested at 10 mM. Compounds having 50% inhibition at 10 mM were considered active. The IC50s of inhibitors (concentration yielding 50% inhibition) were determined from the percent decrease in the rates of substrate hydrolysis in the presence of five to seven different concentrations of the test compound. The results were plotted as percent inhibition versus log inhibitor concentration, and the IC50 was calculated from linear regression of the data. Results are presented in Tables II–VII and in Example 187.

TABLE II

| Cpd # | $R^6$ | $R^7$ | $R^1$ | Y | Q | IC50 (nM) |
|---|---|---|---|---|---|---|
| 12a | $OCH_3$ | $OCH_3$ | I—Bu | O | H | 130* |
| 12b | $OCH_3$ | $OCH_3$ | Bn | O | H | 51* |
| 12c | $OCH_3$ | $OCH_3$ | Bn | NH | H | ~800[a] |
| 12d | $OCH_3$ | $OCH_3$ | Bn | NH | H | ~700[b] |
| 12e | $OCH_3$ | $OCH_3$ | Bn | $NCH_3$ | H | 200[a] |
| 12f | $OCH_3$ | $OCH_3$ | Bn | $NCH_3$ | H | 38[b] |
| 12g | $OCH_3$ | $OCH_3$ | Bn | NBn | H | ~1000[a] |
| 12h | $OCH_3$ | $OCH_3$ | Bn | NBn | H | 150[b] |
| 12i | H | H | Bn | $NCH_3$ | H | 28[a] |
| 12j | H | H | Bn | $NCH_3$ | H | 110[b] |
| 12k | F | H | Bn | $NCH_3$ | H | 28[a] |
| 12l | Cl | Cl | Bn | $NCH_3$ | H | 21[a] |
| 12m | Cl | Cl | Bn | $NCH_3$ | H | 7[b] |
| 12n | Cl | H | Bn | NiBu | H | ~200[a] |

TABLE II-continued

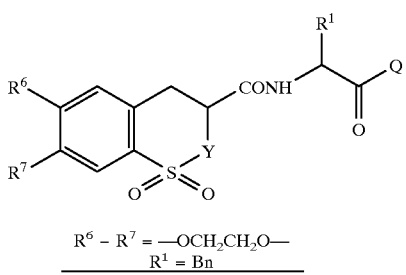

| Cpd # | R⁶ | R⁷ | R¹ | Y | Q | IC50 (nM) |
|---|---|---|---|---|---|---|
| 12o | Cl | H | Bn | NiBu | H | ~200[b] |
| 12p | Cl | H | Bn | NCH₃ | H | 5[a] |
| 12q | Cl | H | Bn | NCH₃ | H | 15[b] |
| 12r | OCH₂CH₂O | | Bn | NCH₃ | H | 24* |
| 12s | OCH₂CH₂O | | Bn | NEt | H | 7[a] |
| 12t | OCH₂CH₂O | | Bn | NEt | H | 33[b] |
| 12u | OCH₂CH₂O | | Bn | NiPr | H | 30* |
| 12v | OCH₂CH₂O | | iBu | NEt | H | ~300[a] |
| 12w | OCH₂CH₂O | | iBu | NEt | H | 37[b] |
| 12x | OCH₂CH₂O | | (CH₂)₄NHSO₂Ph | NCH₃ | H | 36[a] |
| 12y | OCH₂CH₂O | | (CH₂)₄NHSO₂Ph | NCH₃ | H | 107[b] |
| 12z | Morpholin-4-yl | H | Bn | NCH₃ | H | ~500[a] |
| 12aa | Morpholin-4-yl | H | Bn | NCH₃ | H | 30[b] |
| 13 | OCH₂CH₂O | | Bn | NEt | CO₂CH₃ | ~1000* |
| 14A | Cl | H | Bn | NCH₃ | CONHEt | ~1000* |
| 14B | OCH₂CH₂O | | iBu | NEt | CONHBu | ~1000[a] |
| 14C | OCH₂CH₂O | | iBu | NEt | CONHBu | ~500[b] |

*Mixture of diastereomers;
[a,b]Single diastereomers

TABLE III

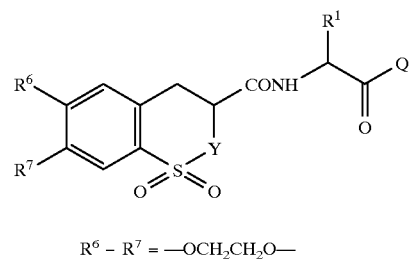

R⁶ – R⁷ = —OCH₂CH₂O—
R¹ = Bn

| Cpd # | Y | Q | IC50 (nM) |
|---|---|---|---|
| 14D | NEt | CONHEt | 340* |
| 14E | NEt | CONHBu | 50[a] |
| 14F | NEt | CONHBu | ~300[b] |
| 14G | NEt | CONHBu | 189* |
| 14H | NEt | CONHCH₂CH₂OCH₃ | ~200* |
| 14I | NEt | CONHCH(CH₃)₂ | 205* |
| 14J | NEt | CONH(CH₂)₄CH₃ | ~150* |
| 14K | NEt | CONHCH₂Ph | 81* |
| 14L | NEt | CONCHCH₂CH₂Ph | 63* |
| 14M | NEt | CONHCH₂CH=CH₂ | ~200* |
| 14N | NEt | CONH(CH₂)₃-(imidazol-1-yl) | ~5000* |
| 14O | NEt | CONH(CH₂)₃-(2-ketopyrrolidin-1-yl) | ~500* |
| 14P | NEt | CONH(CH₂)₃(morpholin-4-yl) | 195* |
| 14Q | NEt | CONHCH₂(pyridin-2-yl) | 170* |
| 14R | NEt | CONHCH₂-cyclopropane | 286* |
| 14S | NEt | CONHCH₂CH₂NHSO₂CH₃ | 89* |
| 14T | NEt | CONHCH₂CH₂NHSO₂(4-NO₂—Ph) | 47* |
| 14U | NEt | CONH(CH₂)₃NHSO₂(4-NO₂—Ph) | 50* |
| 14V | NEt | CONHCH₂CH₂NHSO₂(3,4-Cl₂—Ph) | 56* |
| 14W | NEt | CONH(CH₂)₃NHSO₂(3,4-Cl₂—Ph) | 56* |
| 14X | NEt | CONHCH₂CH₂NHSO₂Ph | 40* |
| 14Y | NEt | CONHCH₂CH₂NHSO₂(5-(2-pyridinyl)-thiophen-2-yl) | 20* |
| 14Z | NEt | CONH(CH₂)₃NHSO₂(4-F—Ph) | 50* |
| 14AA | NEt | CONH(CH₂)₃NHSO₂Ph | 35* |
| 14AB | NEt | CONHCH₂-(pyridin-4-yl) | 240* |
| 14AC | NEt | CONHCH₂CH₂NHSO₂(4-F—Ph) | 29* |
| 14AD | NH | CONHBu | ~200* |
| 14AE | NH | CONHCH₂CH₂NHSO₂Ph | 76* |

*Mixture of diastereomers;
[a,b]Single diastereomers

TABLE IV

[Structure: benzothiazine with R⁴, R⁶, R⁷ substituents, CONH-CHR¹-C(=O)-Q group, Y and S(=O)₂]

| Cpd # | R⁴ | R⁶ | R⁷ | R¹ | Y | Q | IC50 (nM) |
|---|---|---|---|---|---|---|---|
| 26a | H | Cl | Cl | Bn | NCH₃ | H | 15 |
| 26b | H | OCH₂CH₂O | | Bn | NCH₃ | H | 6 |
| 26c | H | OCH₂CH₂O | | Bn | NEt | H | 8 |
| 26d | OCH₃ | H | H | Bn | NCH₃ | H | 37 |
| 27e | H | OCH₂CH₂O | | Bn | NCH₃ | CONHBu | 210 |
| 27f | H | OCH₂CH₂O | | Bn | NEt | OCNHBu | 155 |
| 27g | OCH₃ | H | H | Bn | NCH₃ | CONHBu | 900 |
| 27h | OH | H | H | Bn | NCH₃ | CONHBu | ~10,000 |

TABLE V

[Structure with R⁴, R⁶, R⁷, N-R⁹, S(=O)₂, CONH-CHR¹-C(=O)-Q]

R¹ = Bn; R⁶ = H; R⁷ = H

| Cpd # | R⁹ | R⁴ | Q | IC50 (nM) |
|---|---|---|---|---|
| 35a | Et | Pr | H | ~1,000ᵃ |
| 35b | Et | Pr | H | ~3,000ᵇ |
| 35c | Et | Bn | H | ~10,000ᵃ |
| 35d | Et | Bn | H | ~1,000ᵇ |
| 35e | CH₃ | H | CONHBu | ~2,000* |

*Mixture of diastereomers;
ᵃ,ᵇSingle diastereomers

TABLE VI

[Structure with R⁶, R⁷, N, NH, S(=O)₂, CONH-CHR¹-C(=O)-Q]

R¹ = Bn

| Cpd # | R⁶ | R⁷ | Q | IC50 (nM) |
|---|---|---|---|---|
| 42a | H | H | H | 83 |
| 42b | OCH₂CH₂O | | H | 28 |
| 42c | H | H | CONHBu | ~5,000 |
| 42d | OCH₂CH₂O | | CONHBu | ~10,000 |

TABLE VII

[Structure: tetrahydroisoquinoline with R⁶, R⁷, N-R⁹, C=O, CONH-CHR¹-C(=O)-Q]

R¹ = Bn; R⁶ = H; R⁷ = H

| Cpd # | R⁹ | Q | IC50 (nM) |
|---|---|---|---|
| 50a | H | H | ~5000ᵃ |
| 50b | H | H | ~5000ᵇ |
| 50c | CH₃ | H | ~1000ᵃ |
| 50d | CH₃ | H | 85ᵇ |

ᵃ,ᵇSingle diastereomers

Example 189
Synthesis of 2,3-dihydrobenzothiazole Derivatives 2,3-Dihydrobenzothiazole derivatives (compounds of Formula I, where j=0) can be prepared from 2,3-dihydrobenzothiazole-3-carboxylates according to the methods specified in Scheme I and Examples 1–44. These intermediates can be formed by reduction of 3-hydroxy-2,3-dihydrobenzothiazole-3-carboxylates, described by J. Wrobel and A. Dietrich [Heterocycles 38, 1823 –1838 (1994), incorporated by reference herein in its entirety] with reagents including sodium cyanoborohydride, sodium borohydride, zinc-acetic acid, or catalytic hydrogenation by methods known to those skilled in the art. Alternatively, 2,3-dihydrobenzothiazole-3-carboxylates may be prepared by treating N-alkylbenzenesulfonamides with a strong base such as butyllithium followed by glyoxylic ester by a modification of the method of Wrobel and Dietrich.

Example 190
Synthesis of 4,5-dihydrobenzothiazepine Derivatives 4,5-Dihydrobenzothiazepine derivatives (compounds of Formula I, where j=2) can be prepared from 4,5-dihydrobenzothiazepine-3-carboxylates according to the methods specified in Scheme I and Examples 1–44. These intermediates can be synthesized by modification of previously reported methods. For example, 3-(m-chlorophenyl)propionaldehyde (prepared according to the method of H. Hashizume et al., Chem. Pharm. Bull. 42, 512–520 (1994), incorporated by reference herein in its entirety), can be transformed into m-chlorohomophenylalanine by reaction with sodium cyanide and ammonium carbonate followed by hydrolysis. Treatment of m-chlorohomophenylalanine with chlorosulfonic acid by a modification of the procedure described by H. Zenno and T. Mizutani (Japanese patent application No. 7004990, 1966; Chem. Abstr. 72, 111525, incorporated by reference herein in its entirety) affords 7-chloro-4,5-dihydrobenzothiazepine-3-carboxylate. Alternatively, 2-(aminosulfonyl)phenyl-propanoic acid, described by P. Catsoulacos and C. Camoutsis (J. Heterocycl. Chem. 13, 1309–1314 (1976), incorporated by reference herein in its entirety), may be reduced to the corresponding aldehyde, treated with cyanide, hydrolyzed with acid or base, and cyclized by the procedure of Catsoulacos and Camoutsis to give 4,5-dihydrobenzothiazepine-3-carboxylate.

It is intended that each of the patents, applications, printed publications, and other published documents mentioned or referred to in this specification be herein incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound having the formula:

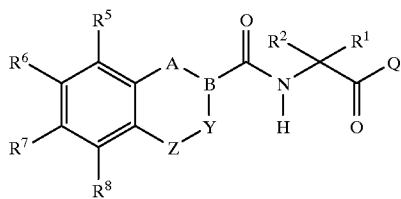

wherein:
- A—B represents one, two, or three carbon atoms or nitrogen atoms, optionally connected by single bonds or one double bond, optionally substituted with one or more groups selected from the group consisting of $R^3$, $R^4$, $OR^3$, $OR^4$, $R^{4a}$, and $OR^{4a}$, with the proviso that the number of nitrogen atoms is 0, 1 or 2;
- $R^1$ and $R^2$ are each independently hydrogen, alkyl having from one to 14 carbons, cycloalkyl having from 3 to 10 carbons, aryl having from 6 to about 14 carbons, heteroaryl having from 6 to about 14 ring atoms, aralkyl having from 7 to 15 carbons, heteroaralkyl, or an optionally protected natural or unnatural side chain of an amino acid, said alkyl, cycloalkyl, aryl, and heteroaryl groups being optionally substituted with one or more K groups;
- $R^3$, $R^4$ and $R^{4a}$ are each independently hydrogen, lower alkyl, or a natural or unnatural side chain of an optionally protected amino acid, said alkyl groups being optionally substituted with an aryl or heteroaryl group;
- $R^5$, $R^6$, $R^7$ and $R^8$ are each independently hydrogen, alkyl having from one to 14 carbons wherein said alkyl groups are optionally substituted with one or more K groups, alkoxy having from one to 10 carbons, halogen, alkoxycarbonyl, carboxyl, hydroxyl, heterocyclic, or amino optionally substituted with 1 to 3 aryl or lower alkyl groups;
- or any two adjacent $R^5$, $R^6$, $R^7$ and $R^8$ groups taken together with any intervening atoms of the benzene ring to which they are attached form an alicyclic, aromatic, heterocyclic, or heteroaryl ring having 5 to 8 ring atoms;
- K is halogen, lower alkyl, lower alkenyl, aryl, heterocyclic, guanidino, nitro, alkoxycarbonyl, alkoxy, hydroxyl, carboxyl, arylaminosulfonyl, heteroarylaminosulfonyl, alkylaminosulfonyl, or amino optionally substituted with an alkylsulfonyl, arylsulfonyl, or heteroarylsulfenyl group, or with 1 to 3 aryl or lower alkyl groups, said alkyl, aryl, and heteroaryl groups being optionally substituted with one or more G groups;
- G is the same as K;
- Y is O, NH, $NR^9$ or $CHR^9$;
- Z is $S(=O))_2$, $S(=O)$, S, or $C(=O)$;
- j is 0, 1 or 2;
- Q is hydrogen, $C(=O)NHR^9$, $C(=O)OR^9$, $CH=N_2$, or $CH_2R^{10}$;
- $R^9$ is hydrogen, alkyl having from one to 10 carbons, said alkyl groups being optionally substituted with one or more K groups, aryl having from 6 to 14 carbons, or aralkyl having from 7 to 15 carbons;
- $R^{10}$ is aryloxy, heteroaryloxy, L, halogen, or has the formula O—M, wherein M has the structure:

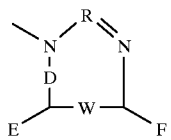

wherein:
- R is N or $CR^{11}$;
- W is a double bond or a single bond;
- D is C=O or a single bond;
- E and F are independently $R^{12}$, $R^{13}$, or J;
- or E and F taken together comprise a joined moiety, said joined moiety being an aliphatic carbocyclic ring optionally substituted with J and having from 5 to 7 carbons, an aromatic carbocyclic ring optionally substituted with J and having from 5 to 7 carbons, an aliphatic heterocyclic ring optionally substituted with J and having from 5 to 7 atoms, or an aromatic heterocyclic ring optionally substituted with J and having from 5 to 7 atoms, said aliphatic heterocyclic ring or said aromatic heterocyclic ring each having from 1 to 4 heteroatoms;
- $R^{11}$, $R^{12}$, and $R^{13}$ are independently H, alkyl having from 1 to 10 carbons, heteroaryl having from 1 to 10 carbons, alkanoyl having from 1 to 10 carbons, or aroyl, wherein said alkyl, heteroaryl, alkanoyl and aroyl groups are optionally substituted with J;
- J is halogen, $C(=O)OR^{14}$, $R^{14}OC(=O)$, $R^{14}OC(=O)NH$, OH, CN, $NO_2$, $NR^{14}R^{15}$, $N=C(R^{14})R^{15}$, $N=C(NR^{14}R^{15})_2$, $SR^{14}$, $OR^{14}$, phenyl, napthy heteroaryl, or a cycloalkyl group having from 3 to 8 carbons;
- $R^{14}$ and $R^{15}$ are independently H, alkyl having from 1 to 10 carbons, aryl, or heteroaryl, wherein said alkyl, aryl and heteroaryl groups are optionally substituted with K;
- L is a phosphorus-containing enzyme reactive group having the formula:

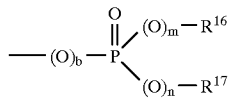

wherein:
- m, n, and b are each independently 0 or 1;
- $R^{16}$ and $R^{17}$ are each independently hydrogen, lower alkyl optionally substituted with K, aryl optionally substituted with K, or heteroaryl optionally substituted with K;
- or $R^{16}$ and $R^{17}$ taken together with $—(O)_n—P(=O)—(O)_m—$ can form a 5–8 membered ring containing up to 3 hetero atoms;
- or $R^{16}$ and $R^{17}$ taken together with $—(O)_n—P(=O)—(O)_m$- can form a 5–8 membered ring optionally substituted with K;

or a pharmaceutically acceptable salt or bisulfite addition product thereof.

2. The compound of claim 1 wherein A—B is —[CH($R^4$)]$_j$—C($R^3$)—, —C($R^4$)=C—, —CH(O$R^4$)—C($R^3$)—, —C(O$R^4$)=C—, —N($R^4$)—C($R^3$)—, —N=C—, —C($R^{4a}$)=C($R^4$)—C($R^3$)—, or —CH($R^{4a}$)—C($R^4$)=C— where j is 0, 1, or 2.

3. The compound of claim 2 wherein A—B is —[CH($R^4$)]$_j$—C($R^3$)— where j is 1, —C($R^4$)=C—, —N($R^4$)—C($R^3$)—, or —N=C—.

4. The compound of claim 3 wherein $R^3$ and $R^4$ are each H.

5. The compound of claim 1 wherein Z is $SO_2$ or C(=O).

6. The compound of claim 5 wherein Z is $SO_2$.

7. The compound of claim 1 wherein $R^2$, $R^5$ and $R^8$ are each H.

8. The compound of claim 1 wherein $R^1$ is alkyl or aralkyl.

9. The compound of claim 8 wherein $R^1$ is i-butyl or benzyl.

10. The compound of claim 1 wherein $R^6$ and $R^7$ are independently H, alkoxy, halogen, or heterocyclic, or $R^6$ and $R^7$ taken together form —O—$CH_2$—$CH_2$—O—.

11. The compound of claim 10 wherein $R^6$ and $R^7$ are independently H, —$OCH_3$, F, Cl, or morpholin-4-yl, or $R^6$ and $R^7$ taken together form —O—$CH_2$—$CH_2$O—.

12. The compound of claim 1 wherein Q is H, C(=O)NH$R^9$, or C(=O)O$R^9$, where $R^9$ is alkyl or alkyl substituted with K.

13. The compound of claim 1 wherein Y is O, NH, N$R^9$ or CH$R^9$, where $R^9$ is alkyl or aralkyl.

14. The compound of claim 13 wherein Y is N$R^9$ or CH$R^9$, where $R^9$ is methyl ethyl, propyl, i-butyl or benzyl.

15. The compound of claim 2 wherein A—B is —[CH($R^4$)]$_j$—C($R^3$)—, —C($R^4$)=C—, —N($R^4$)—C($R^3$)—, or —N=C—; Z is $SO_2$ or C(=O); $R^2$, $R^5$ and $R^8$ are each H; $R^1$ is alkyl or aralkyl; $R^6$ and $R^7$ are independently H, alkoxy, halogen, or heterocyclic, or R6 and R7 taken together form —O—$CH_2$—$CH_2$O—; Q is H, C(=O)NH$R^9$, or C(=O)O$R^9$, where $R^9$ is alkyl or alkyl substituted with K; Y is O, NH, N$R^9$ or CH$R^9$, where $R^9$ is alkyl or aralkyl.

16. The compound of claim 15 wherein Z is $SO_2$.

17. The compound of claim 15 wherein $R^1$ is i-butyl or benzyl.

18. The compound of claim 15 wherein $R^6$ and $R^7$ are independently H, —$OCH_3$, F, Cl, or morpholin-4-yl, or $R^6$ and $R^7$ taken together form —O—$CH_2$—$CH_2$O—.

19. The compound of claim 15 wherein Y is N$R^9$ or CH$R^9$, where $R^9$ is methyl ethyl, propyl, i-butyl or benzyl.

20. The compound of claim 15 wherein A—B is —$CH_2$—CH—.

21. The compound of claim 1 having the formula:

wherein:
$R^1$ is alkyl, alkyl substituted with K, or aralkyl;
$R^6$ and $R^7$ are independently H, alkoxy, halogen, or heterocyclic, or $R^6$ and $R^7$ taken together form —O—$CH_2$—$CH_2$—O—;
Q is H, C(=O)NH$R^9$, or C(=O)O$R^9$, where $R^9$ is alkyl; and
Y is O, NH or N$R^9$ where $R^9$ is alkyl or aralkyl.

22. The compound of claim 21 wherein $R^1$ is i-butyl, benzyl, or alkyl substituted with phenylsulfonyl-amino.

23. The compound of claim 21 wherein $R^6$ and $R^7$ are independently H, $OCH_3$, F, Cl, or morpholin-4-yl, or $R^6$ and $R^7$ taken together form —O—$CH_2$—$CH_2$O—.

24. The compound of claim 21 wherein Q is C(=O)NH$R^9$, or C(=O)O$R^9$, where $R^9$ is methyl, ethyl, or butyl.

25. The compound of claim 21 wherein Y is O, NH or N$R^9$, wherein $R^9$ is methyl, ethyl, i-propyl, i-butyl or benzyl.

26. The compound of claim 21 wherein $R^1$, $R^6$, $R^7$, Y and Q have the values shown in the horizontal rows of the following table:

| $R^6$ | $R^7$ | $R^1$ | Y | Q |
|---|---|---|---|---|
| $OCH_3$ | $OCH_3$ | i-Bu | O | H |
| $OCH_3$ | $OCH_3$ | Bn | O | H |
| $OCH_3$ | $OCH_3$ | Bn | NH | H |
| $OCH_3$ | $OCH_3$ | Bn | $NCH_3$ | H |
| $OCH_3$ | $OCH_3$ | Bn | NBn | H |
| H | H | Bn | $NCH_3$ | H |
| F | H | Bn | $NCH_3$ | H |
| Cl | Cl | Bn | $NCH_3$ | H |
| Cl | H | Bn | NiBu | H |
| Cl | H | Bn | $NCH_3$ | H |
| $OCH_2CH_2O$ | | Bn | $NCH_3$ | H |
| $OCH_2CH_2O$ | | Bn | NEt | H |
| $OCH_2CH_2O$ | | Bn | NiPr | H |
| $OCH_2CH_2O$ | | iBu | NEt | H |
| $OCH_2CH_2O$ | | $(CH_2)_4NHSO_2Ph$ | $NCH_3$ | H |
| Morpholin-4-yl | H | Bn | $NCH_3$ | H |
| $OCH_2CH_2O$ | | Bn | NEt | $CO_2CH_3$ |
| Cl | H | Bn | $NCH_3$ | CONHEt |
| $OCH_2CH_2O$ | | iBu | NEt | CONHBu |

27. The compound of claim 1 having the formula:

wherein:
$R^1$ is benzyl;
$R^6$ and $R^7$ taken together form —O—$CH_2$—$CH_2$O—;
Y is N-H or N$R^9$ wherein $R^9$ is ethyl; and
Q is C(=O)NH$R^9$ where $R^9$ is alkyl or alkyl substituted with K.

28. The compound of claim 27 wherein Q is CONHEt, CONHBu, CONH$CH_2CH_2OCH_3$, CONHCH($CH_3$)$_2$, CONH($CH_2$)$_4CH_3$, CONH$CH_2$Ph, CONH$CH_2CH_2$Ph, CONH$CH_2$CH=$CH_2$, CONH($CH_2$)$_3$-(imidazol-1-yl), CONH ($CH_2$)$_3$-(2-ketopyrrolidin-1-yl), CONH($CH_2$)$_3$ (morpholin-4-yl), CONH$CH_2$(pyridin-2-yl), CONH$CH_2$-cyclopropane, CONH$CH_2CH_2NHSO_2CH_3$, CONH$CH_2CH_2NHSO_2$(4—$NO_2$-Ph), CONH($CH_2$)$_3$ NH$SO_2$(4—$NO_2$-Ph), CONH$CH_2CH_2NHSO_2$(3,4—$Cl_2$-Ph), CONH($CH_2$)$_3NHSO_2$ (3,4—$Cl_2$-Ph), CONH$CH_2CH_2NHSO_2$Ph, CONH$CH_2CH_2NHSO_2$ (5-(2-pyridinyl)-thiophen-2-yl), CONH ($CH_2$)$_3NHSO_2$ (4-F-Ph), CONH($CH_2$)$_3NHSO_2$Ph, CONH$CH_2$-(pyridin-4-yl), or CONH$CH_2CH_2NHSO_2$ (4-F-Ph).

29. The compound of claim 27 wherein Y and Q have the values shown in the horizontal rows of the following table:

| Y | Q |
|---|---|
| NEt | CONHEt |
| NEt | CONHBu |
| NEt | CONHCH$_2$CH$_2$OCH$_3$ |
| NEt | CONHCH(CH$_3$)$_2$ |
| NEt | CONH(CH$_2$)$_4$CH$_3$ |
| NEt | CONHCH$_2$Ph |
| NEt | CONHCH$_2$CH$_2$Ph |
| NEt | CONHCH$_2$CH=CH$_2$ |
| NEt | CONH(CH$_2$)$_3$-(imidazol-1-yl) |
| NEt | CONH(CH$_2$)$_3$-(2-ketopyrrolidin-1-yl) |
| NEt | CONH(CH$_2$)$_3$(morpholin-4-yl) |
| NEt | CONHCH$_2$(pyridin-2-yl) |
| NEt | CONHCH$_2$-cyclopropane |
| NEt | CONHCH$_2$CH$_2$NHSO$_2$CH$_3$ |
| NEt | CONHCH$_2$CH$_2$NHSO$_2$(4-NO$_2$-Ph) |
| NEt | CONH(CH$_2$)$_3$NHSO$_2$(4-NO$_2$-Ph) |
| NEt | CONHCH$_2$CH$_2$NHSO$_2$(3,4-Cl$_2$-Ph) |
| NEt | CONH(CH$_2$)$_3$NHSO$_2$(3,4-Cl$_2$-Ph) |
| NEt | CONHCH$_2$CH$_2$NHSO$_2$Ph |
| NEt | CONHCH$_2$CH$_2$NHSO$_2$(5-(2-pyridinyl)-thiophen-2-yl) |
| NEt | CONH(CH$_2$)$_3$NHSO$_2$(4-F-Ph) |
| NEt | CONH(CH$_2$)$_3$NHSO$_2$Ph |
| NEt | CONHCH$_2$-(pyridin-4-yl) |
| NEt | CONHCH$_2$CH$_2$NHSO$_2$(4-F-Ph) |
| NH | CONHBu |
| NH | CONHCH$_2$CH$_2$NHSO$_2$Ph |

30. The compound of claim 1 having the formula:

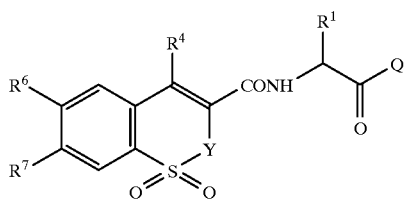

wherein:

$R^1$ is benzyl;

$R^6$ and $R^7$ are independently H or halogen, or $R^6$ and $R^7$ taken together form —O—CH$_2$—CH$_2$—O—;

$R^4$ is H, alkoxy, or hydroxy;

Y is NR$^9$ wherein $R^9$ is alkyl; and

Q is H or C(=O)NHR$^9$ where $R^9$ is alkyl.

31. The compound of claim 30 wherein Q is H or CONHBu.

32. The compound of claim 30 wherein $R^6$ and $R^7$ are independently H or Cl, or $R^6$ and $R^7$ taken together form —O—CH$_2$—CH$_2$—O—.

33. The compound of claim 30 wherein $R^4$ is H, methoxy, or hydroxy.

34. The compound of claim 30 wherein Y is NR$^9$ wherein $R^9$ is methyl or ethyl.

35. The compound of claim 30 wherein Y, Q, $R^1$, $R^4$, $R^6$ and $R^7$ have the values shown in the horizontal rows of the following table:

| $R^4$ | $R^6$ | $R^7$ | $R^1$ | Y | Q |
|---|---|---|---|---|---|
| H | Cl | Cl | Bn | NCH$_3$ | H |
| H | OCH$_2$CH$_2$O | | Bn | NCH$_3$ | H |
| H | OCH$_2$CH$_2$O | | Bn | NEt | H |
| OCH$_3$ | H | H | Bn | NCH$_3$ | H |

-continued

| $R^4$ | $R^6$ | $R^7$ | $R^1$ | Y | Q |
|---|---|---|---|---|---|
| H | OCH$_2$CH$_2$O | | Bn | NCH$_3$ | CONHBu |
| H | OCH$_2$CH$_2$O | | Bn | NEt | CONHBu |
| OCH$_3$ | H | H | Bn | NCH$_3$ | CONHBu |
| OH | H | H | Bn | NCH$_3$ | CONHBu |

36. The compound of claim 1 having the formula:

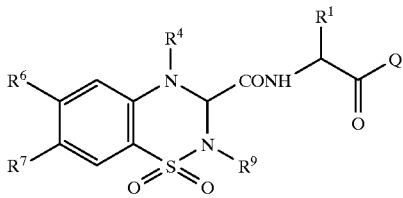

wherein:

$R^1$ is benzyl;

$R^6$ and $R^7$ are each H;

$R^4$ is H, alkyl, or aralkyl;

$R^9$ is alkyl; and

Q is H or C(=O)NHR$^9$ where $R^9$ is alkyl.

37. The compound of claim 36 wherein $R^4$ is H, propyl, or benzyl.

38. The compound of claim 36 wherein Q is H or CONHBu.

39. The compound of claim 36 wherein $R^9$ is ethyl or ethyl.

40. The compound of claim 36 wherein $R^4$, $R^9$ and Q have the values shown in the horizontal rows of the following table:

| $R^9$ | $R^4$ | Q |
|---|---|---|
| Et | Pr | H |
| Et | Bn | H |
| CH$_3$ | H | CONHBu |

41. The compound of claim 1 having the formula:

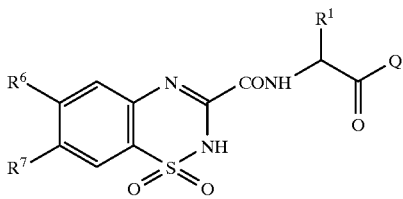

wherein:

$R^1$ is benzyl;

$R^6$ and $R^7$ are each H, or $R^6$ and $R^7$ taken together form —O—CH$_2$—CH$_2$—O—; and Q is H or C(=O)NHR$^9$ where $R^9$ is alkyl.

42. The compound of claim 41 wherein Q is H or CONHBu.

43. The compound of claim 41 wherein $R^6$, $R^7$ and Q have the values shown in the horizontal rows of the following table:

| R[6] | R[7] | Q |
| --- | --- | --- |
| H | H | H |
| OCH$_2$CH$_2$O | | H |
| H | H | CONHBu |
| OCH$_2$CH$_2$O | | CONHBu |

44. The compound of claim 1 having the formula:

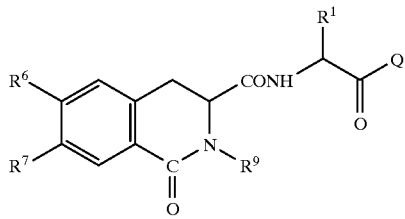

wherein:
R$^1$ is benzyl;
R$^6$ and R$^7$ are each H;
Q is H; and
R$^9$ is H or alkyl.

45. The compound of claim 44 wherein R$^9$ is H or CH$_3$.

46. The compound of claim 1 having the formula:

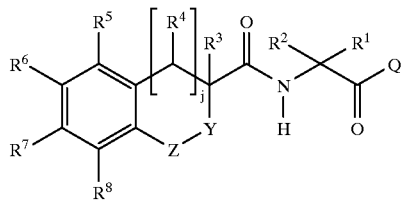

wherein:
R$^1$ and R$^2$ are each independently hydrogen, alkyl having from one to about 14 carbons, cycloalkyl having from 3 to about 10 carbons, aryl having from about 6 to about 14 carbons, heteroaryl having from about 6 to about 14 ring atoms, aralkyl having from about 7 to about 15 carbons, heteroaralkyl, or an optionally protected natural or unnatural side chain of an amino acid, said alkyl, cycloalkyl, aryl, and heteroaryl groups being optionally substituted with one or more K groups;
R$^3$ and R$^4$ are each independently hydrogen, lower alkyl, or a natural or unnatural side chain of an optionally protected amino acid, said alkyl groups being optionally substituted with an aryl or heteroaryl group;
R$^5$, R$^6$, R$^7$ and R$^8$ are each independently hydrogen, alkyl having from one to about 14 carbons wherein said alkyl groups are optionally substituted with one or more K groups, alkoxy having from one to about 10 carbons, halogen, alkoxycarbonyl, carboxyl, hydroxyl, or amino optionally substituted with 1 to 3 aryl or lower alkyl groups;
or any two adjacent R$^5$, R$^6$, R$^7$ and R$^8$ groups taken together with any intervening atoms of the benzene ring to which they are attached form an alicyclic, aromatic, heterocyclic, or heteroaryl ring having 5 to 8 ring atoms;
K is halogen, lower alkyl, aryl, heteroaryl, guanidino, alkoxycarbonyl, alkoxy, hydroxyl, carboxyl, or amino optionally substituted with 1 to 3 aryl or lower alkyl groups;
Y is O, NH, NHR$^9$ or CHR$^9$;
Z is S(=O)$_2$, S(=O), S, or C(=O)
j is 0, 1 or 2;
Q is H, C(=O)NHR$^9$, C(=O)OR$^9$, CH=N$_2$, or CH$_2$R$^{10}$;
R$^9$ is hydrogen, alkyl having from one to about 10 carbons, said alkyl groups being optionally substituted with one or more K groups, aryl having from about 6 to about 14 carbons, or aralkyl having from about 7 to about 15 carbons;
R$^{10}$ is aryloxy, heteroaryloxy, L, halogen, or has the formula O—M, wherein M has the structure:

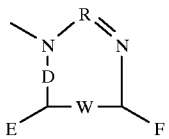

wherein:
R is N or CR$^{11}$;
W is a double bond or a single bond;
D is C=O or a single bond;
E and F are independently R$^{12}$, R$^{13}$, or J;
or E and F taken together comprise a joined moiety, said joined moiety being an aliphatic carbocyclic ring optionally substituted with J and having from 5 to 7 carbons, an aromatic carbocyclic ring optionally substituted with J and having from 5 to 7 carbons, an aliphatic heterocyclic ring optionally substituted with J and having from 5 to 7 atoms, or an aromatic heterocyclic ring optionally substituted with J and having from 5 to 7 atoms, said aliphatic heterocyclic ring or said aromatic heterocyclic ring each having from 1 to 4 heteroatoms;
R$^{11}$, R$^{12}$, and R$^{13}$ are independently H, alkyl having from 1 to 10 carbons, heteroaryl having from 1 to 10 carbons, alkanoyl having from 1 to 10 carbons, or aroyl, wherein said alkyl, heteroaryl, alkanoyl and aroyl groups are optionally substituted with J;
J is halogen, C(=O)OR$^{14}$, R$^{14}$OC(=O), R$^{14}$OC(=O)NH, OH, CN, NO$_2$, NR$^{14}$R$^{15}$, N=C (R$^{14}$) R$^{15}$, N=C (NR$^{14}$R$^{15}$)$_2$, SR$^{14}$, OR$^{14}$, phenyl, naphthyl, heteroaryl, or a cycloalkyl group having from 3 to 8 carbons;
R$^{14}$ and R15 are independently H, alkyl having from 1 to 10 carbons, aryl, or heteroaryl, wherein said alkyl, aryl and heteroaryl groups are optionally substituted with K;
L is a phosphorus-containing enzyme reactive group having the formula:

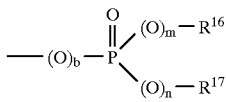

wherein:
m, n, and b are each independently 0 or 1;
R$^{16}$ and R$^{17}$ are each independently hydrogen, lower alkyl optionally substituted with K, aryl optionally substituted with K, or heteroaryl optionally substituted with K;

or $R^{16}$ and $R^{17}$ taken together with $-(O)_N-P(=O)-(O)_m-$ can form a 5–8 membered ring containing up to 3 hetero atoms;

or $R^6$ and $R^{17}$ taken together with $-(O)_n-P(=O)-(O)_m-$ can form a 5–8 membered ring optionally substituted with K.

47. The compound of claim 1 wherein Z is SO.
48. The compound of claim 1 wherein Z is S.
49. The compound of claim I wherein Q is $CH_2R^{10}$.
50. The compound of claim 49 wherein $R^{10}$ is $-O-M$.
51. The compound of claim 49 wherein $R^{10}$ is -L.
52. The compound of claim 1 wherein Q is H.
53. The bisulfite addition product of the compound of claim 52.

* * * * *

UNITED STATES PATENT AND TRADEMARK OFFICE
CERTIFICATE OF CORRECTION

PATENT NO. : 5,952,328  
DATED : September 14, 1999  
INVENTOR(S) : Bihovsky et al.

Page 1 of 7

It is certified that error appears in the above-identified patent and that said Letters Patent is hereby corrected as shown below:

Title page,
Under OTHER PUBLICATIONS,
At "Close, W.J. et al.", lines 3-4 thereof, please delete "bendothiadiazine" and insert -- benzothiadiazine -- therefor.
At "Short, J.H. et al.", second line thereof, please delete "Benzothiadizine" and insert -- Benzothiadiazine -- therefor.
At "Swett, L. et al.", second line thereof, please delete "Dreivaties" and insert -- Derivatives -- therefor.
At "Lombardino, J.G. et al.", second line thereof, please delete "Caboxamides" and insert -- Carboxamides -- therefor.

Column 3,
Line 15, please delete "S(=O)$_3$" and insert -- S(=O)$_2$ -- therefor.
Line 58, please delete "R$^4$OC(=O)" and insert -- R$^{14}$OC(=O) -- therefor.
Line 59, please delete "N=C(R$^4$)R$^{15}$" and insert -- N=C(R$^{14}$)R$^{15}$ -- therefor.

Column 15,
Please delete

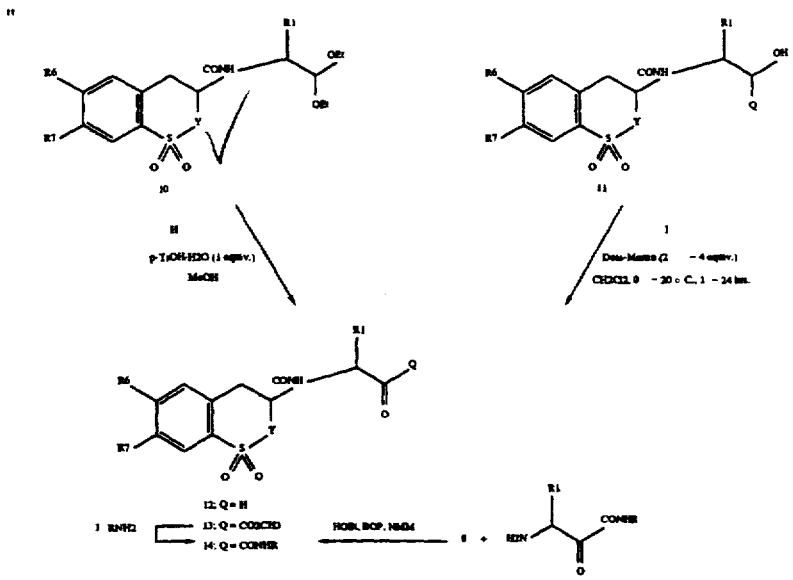

UNITED STATES PATENT AND TRADEMARK OFFICE
CERTIFICATE OF CORRECTION

PATENT NO. : 5,952,328
DATED : September 14, 1999
INVENTOR(S) : Bihovsky et al.

It is certified that error appears in the above-identified patent and that said Letters Patent is hereby corrected as shown below:

and insert

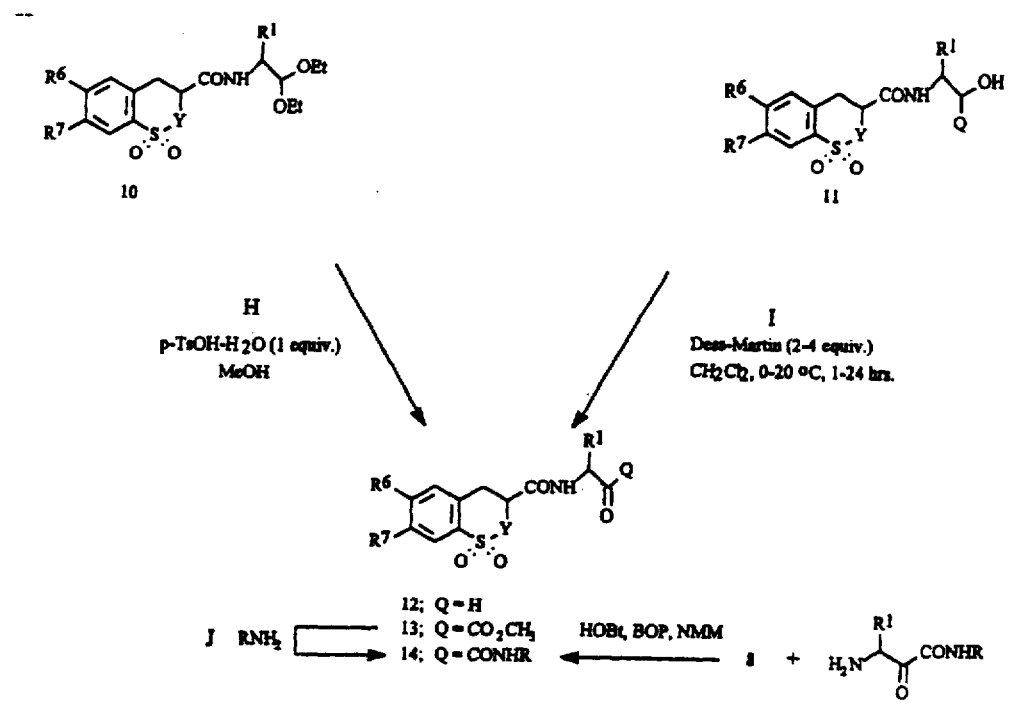

-- therefor.

UNITED STATES PATENT AND TRADEMARK OFFICE
CERTIFICATE OF CORRECTION

PATENT NO. : 5,952,328
DATED : September 14, 1999
INVENTOR(S) : Bihovsky et al.

It is certified that error appears in the above-identified patent and that said Letters Patent is hereby corrected as shown below:

Column 22,
Please delete

"
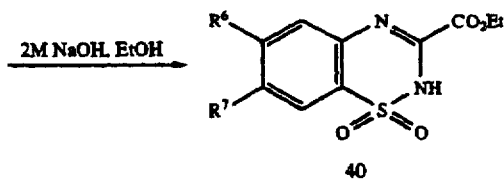
" therefor.

and insert

--
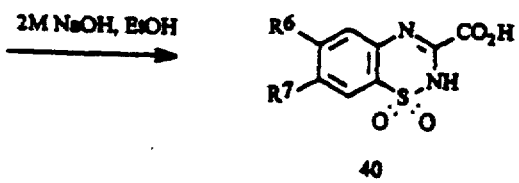
-- therefor.

UNITED STATES PATENT AND TRADEMARK OFFICE
CERTIFICATE OF CORRECTION

PATENT NO. : 5,952,328
DATED : September 14, 1999
INVENTOR(S) : Bihovsky et al.

It is certified that error appears in the above-identified patent and that said Letters Patent is hereby corrected as shown below:

Column 25,
Line 31, please delete "NaoAc" and insert -- NaOAc -- therefor.

Column 26,
Lines 1-12, please delete

"
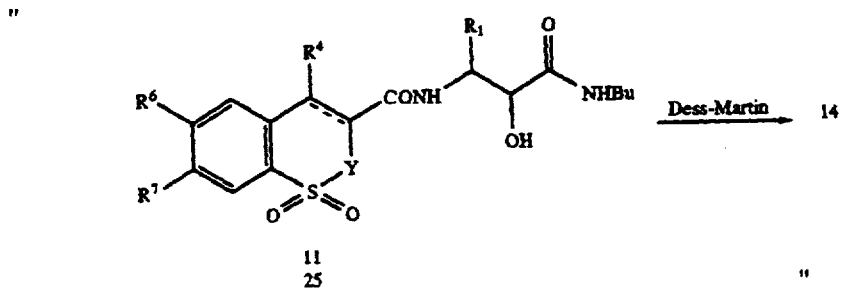
"

and insert

--
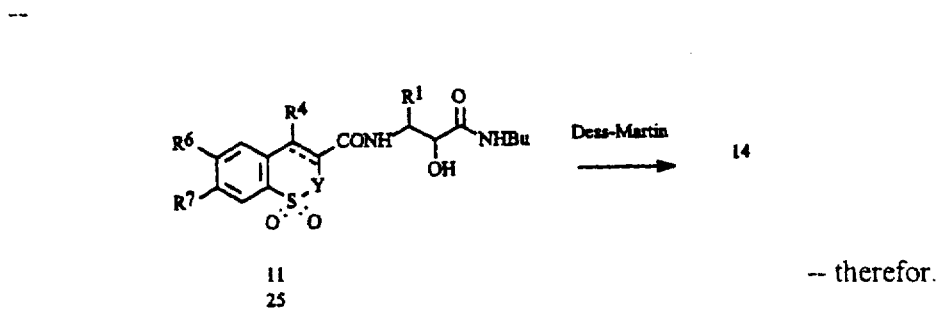
-- therefor.

UNITED STATES PATENT AND TRADEMARK OFFICE
CERTIFICATE OF CORRECTION

PATENT NO. : 5,952,328
DATED : September 14, 1999
INVENTOR(S) : Bihovsky et al.

It is certified that error appears in the above-identified patent and that said Letters Patent is hereby corrected as shown below:

Column 27,
Line 23, please delete "($R^6=R^7=$OCH3)" and insert -- ($R^6=R^7=OCH_3$) -- therefor.

Column 30,
Line 4, please delete "From 4" and insert -- From 41 -- therefor.

Column 32,
Line 53, please delete "($DMSO_{-6}$)" and insert -- ($DMSO-d_6$) -- therefor.

Column 33,
Line 47, please delete "R $CH_3$)" and insert -- R=$CH_3$) -- therefor.

Column 36,
Line 19, please delete "1,2-enzothiazine-3-" and insert
-- 1,2-benzothiazine-3- -- therefor.
Line 44, please delete "methy" and insert -- methyl -- therefor.

Column 37,
Line 24, please delete "pheniylalaninol" and insert -- phenylalaninol -- therefor.
Line 57, please delete "tic" and insert -- tic -- therefor.
Line 63, please delete "N-(3,4-Dihydro" and insert -- $N_\alpha$-(3,4-Dihydro -- therefor.

Column 38,
Line 4, please delete "MesH/$CH_2Cl_2$)" and insert -- MeOH/$CH_2Cl_2$) -- therefor.

Column 39,
Line 49, please delete "aminoethanamine" and insert -- amino)ethanamine -- therefor.

Column 40,
Line 67, please delete "ethylenedior" and insert -- ethylenedioxy -- therefor.

Column 43,
Line 27, please delete "dimnethoxy" and insert -- dimethoxy -- therefor.

Column 44,
Line 24, please delete "($Cl_{12}$ pattern)" and insert -- ($Cl_2$ pattern) -- therefor.

UNITED STATES PATENT AND TRADEMARK OFFICE
CERTIFICATE OF CORRECTION

PATENT NO. : 5,952,328
DATED : September 14, 1999
INVENTOR(S) : Bihovsky et al.

It is certified that error appears in the above-identified patent and that said Letters Patent is hereby corrected as shown below:

Column 45,
Line 40, please delete "ethylenediowcy" and insert -- ethylenedioxy -- therefor.

Column 51,
Line 2, please delete "($R^6+R^7$= $OCHC_2H_2O$" and insert -- ($R^6+R^7$=$OCH_2CH_2O$ -- therefor.

Column 52,
Line 26, please delete "(DMSQ-d6)" and insert -- (DMSO-d6) -- therefor.

Column 59,
Line 23, please delete "1,2,4–benzothiadiazin" and insert -- 1,2,4–benzothiadiazine -- therefor.

Column 61,
Line 45, please delete "(61)" and insert -- (61%) -- therefor.

Column 65,
Table III, line 57, at 14L, please delete "$CONCHCH_2CH_2Ph$" and insert -- $CONHCH_2CH_2Ph$ -- therefor.

Column 67,
Table IV, line 21, at 27f, please delete "OCNHBu" and insert -- CONHBu -- therefor.

Column 69, claim 1,
Line 60, please delete to "heteroarylsulfcnyl" and insert -- heteroarylsulfonyl -- therefor.
Line 66, please delete "S(=O))$_2$" and insert -- S(=O)$_2$ -- therefor.

Column 70, claim 1,
Line 57, please delete "$R^{16\ and\ R17}$" and insert -- $R^{16}$ and $R^{17}$ -- therefor.

Column 71, claim 3,
Line 9, please delete " –[CH($R^4$]$_j$ " and insert -- –[CH($R^4$)]$_j$ -- therefor.

Column 71, claim 15,
Line 39, please delete " –O–$CH_2$–$CH_2O$–" and insert -- –O–$CH_2$–$CH_2$–0– -- therefor.

UNITED STATES PATENT AND TRADEMARK OFFICE
CERTIFICATE OF CORRECTION

PATENT NO. : 5,952,328
DATED : September 14, 1999
INVENTOR(S) : Bihovsky et al.

It is certified that error appears in the above-identified patent and that said Letters Patent is hereby corrected as shown below:

Column 71, claim 18,
Line 47, please delete " $-O-CH_2-CH_2O-$ " and insert
-- $-O-CH_2-CH_2-0-$ -- therefor.

Column 72, claim 23,
Line 9, please delete " $-O-CH_2-CH_2O-$ " and insert
-- $-O-CH_2-CH_2-0-$ -- therefor. U Column 72, claim 27,
Line 50, please delete " $-O-CH_2-CH_2O-$ " and insert -- $-O-CH_2-CH_2-0-$ -- therefor.

Column 74, claim 39,
Line 33, please delete "ethyl" and insert -- methyl -- therefor.

Column 77, claim 46,
Line 1, please delete " $-(O)_N-P(=O)-$ " and insert
-- $-(O)_n-P(=O)-$ -- therefor.

Column 78, claim 49,
Line 1, please delete "claim I" and insert -- claim 1 -- therefor.

Signed and Sealed this

Eighth Day of January, 2002

*Attest:*

JAMES E. ROGAN
*Director of the United States Patent and Trademark Office*

*Attesting Officer*